US008129353B2

(12) United States Patent
Allikmets et al.

(10) Patent No.: US 8,129,353 B2
(45) **Date of Patent: *Mar. 6, 2012**

(54) METHODS OF GENE THERAPY USING NUCLEIC ACID SEQUENCES FOR ATP-BINDING CASSETTE TRANSPORTER

(75) Inventors: Rando Allikmets, Frederick, MD (US); Kent L. Anderson, Houston, TX (US); Michael Dean, Frederick, MD (US); Mark Leppert, Salt Lake City, UT (US); Richard A. Lewis, Houston, TX (US); Yixin Li, Houston, TX (US); James R. Lupski, Houston, TX (US); Jeremy Nathans, Baltimore, MD (US); Amir Rattner, Baltimore, MD (US); Noah F. Shroyer, Houston, TX (US); Nanda Singh, Salt Lake City, UT (US); Philip Smallwood, Woodbine, MD (US); Hui Sun, Baltimore, MD (US)

(73) Assignees: Baylor College of Medicine, Houston, TX (US); John Hopkins University, Baltimore, MD (US); The United States of America as represented by the Secretary, Department of Health and Human Services, Washington, DC (US); University of Utah Research Foundation, Salt Lake City, UT (US)

( * ) Notice: Subject to any disclaimer, the term of this patent is extended or adjusted under 35 U.S.C. 154(b) by 1416 days.

This patent is subject to a terminal disclaimer.

(21) Appl. No.: 11/636,909

(22) Filed: Dec. 11, 2006

(65) Prior Publication Data

US 2009/0029930 A1 Jan. 29, 2009

Related U.S. Application Data

(60) Continuation of application No. 10/336,219, filed on Jan. 3, 2003, now Pat. No. 7,192,579, which is a division of application No. 09/032,438, filed on Feb. 27, 1998, now Pat. No. 6,713,300.

(60) Provisional application No. 60/039,388, filed on Feb. 27, 1997.

(51) Int. Cl.

| | |
|---|---|
| *A61K 48/00* | (2006.01) |
| *A61K 38/43* | (2006.01) |
| *C07H 21/02* | (2006.01) |

(52) U.S. Cl. ..................... 514/44 R; 536/23.1; 424/94.1

(58) Field of Classification Search ........................ None
See application file for complete search history.

(56) References Cited

U.S. PATENT DOCUMENTS

| | | | | |
|---|---|---|---|---|
| 4,683,195 | A | 7/1987 | Mullis et al. | 435/6 |
| 4,683,202 | A | 7/1987 | Mullis | 435/91 |
| 4,800,159 | A | 1/1989 | Mullis et al. | 435/172.3 |
| 4,883,750 | A | 11/1989 | Whiteley et al. | 435/6 |
| 6,713,300 | B1 * | 3/2004 | Allikmets et al. | 435/325 |
| 7,141,420 | B2 | 11/2006 | Allikmets et al. | 435/325 |
| 7,192,579 | B2 * | 3/2007 | Allikmets et al. | 424/93.1 |

FOREIGN PATENT DOCUMENTS

| | | |
|---|---|---|
| EP | 0 329 822 | 8/1989 |
| GB | 2 202 328 | 9/1988 |
| WO | WO 87/06270 | 11/1987 |
| WO | WO 88/10315 | 12/1988 |
| WO | WO 89/06700 | 7/1989 |
| WO | WO89/09284 | 10/1989 |

OTHER PUBLICATIONS

Allikmets, R., et al., "A photoreceptor cell-specific ATP-binding transporter gene (ABCR) is mutated in recessive Stargardt macular dystrophy," Nature Genetics, 1997, 15, 236-246.

Allikmets, R., et al., "Mutation of the Stargardt Disease Gene (ABCR) in Age-Related Macular Degeneration," Science, 1997, 277, 1805-1807.

Allikmets, R., et al., "Characterization of the human ABC superfamily: isolation an dmapping of 21 new genes using the expressed sequence tags database," Hum. Mol. Genet., 1996, 5, 1649-1655.

Allikmets, R., et al., "Characterization and mapping of three new mammalian ATP-binding transporter genes from an EST database," Mam. Genome, 1995, 6, 114-117.

Allikmets, R., et al., "Cloning and organization of the abc and mdl genes of *Escherichia coli*: relationship to eukaryotic multidrug resistance," Gene, 1993, 136, 231-236.

Anderson, K. L., "Towards the Isolation of Genes for Recessively Inherited Ocular Disorders; Bardet-Biedl Syndrome, Leber Congenital Amaurosis, Primary Congenital Glaucoma, and Stargardt Disease," Ph.D. Thesis, Baylor College of Medicine, Jul. 30, 1996 (abstract).

Anderson, R. E., et al., "Lipids of Ocular Tissues," Arch. Biochem. Biophys., 1971, 151, 270-276.

Anderson, K.L., et al., Am. J. Hum. Genet., 1995, 57, 1351-1363.

Azarian, S. M., et al., "The photoreceptor rim protein is an ABC transporter encoded by the gene for recessive stargardt's disease (ABCR)," FEBS Letts., 1997, 409, 247-252.

Birnbach, C. D., et al., "Histopathology and Immunocytochemistry of the Neurosensory retina in Fundus Flavimaculatus," Ophthalmology, 1994, 101, 1211-1219.

Blacharski, D. A., "Fundus flavimaculatus. In Retinal Dystrophies and Degenerations," D.A. Newsome (Ed.), Raven Press, New York, 1988, Chapter 9, 135-159.

(Continued)

*Primary Examiner* — Robert M Kelly
(74) *Attorney, Agent, or Firm* — Fulbright & Jaworski L.L.P.

(57) ABSTRACT

The present invention provides nucleic acid and amino acid sequences of an ATP binding cassette transporter and mutated sequences thereof associated with macular degeneration. Methods of detecting agents that modify ATP-binding cassette transporter comprising combining purified ATP binding cassette transporter and at least one agent suspected of modifying the ATP binding cassette transporter an observing a change in at least one characteristic associated with ATP binding cassette transporter. Methods of detecting macular degeneration is also embodied by the present invention.

6 Claims, 19 Drawing Sheets

OTHER PUBLICATIONS

Chen, Z-Y., et al., "Norrie Disease Gene: Characterization of Deletions and Possible Function," Genomics, 1993, 16, 533-535.
Childs, S., et al., "The MDR Superfamily of Genes and Its Biological Implications," Important Advances in Oncology, 1994, DeVita, V. T, et al. (Eds.), Lippincott Company, Philadelphia, PA, 21-36.
Chiu, M. I., et al., "Murine and Bovine Blue Cone Pigment Genes: Cloning and Characterization of Two New Members of the S Family of Visual Pigments," Genomics, 1994, 21, 440-443.
Cline, M. J., "Perspectives for Gene Therapy: Inserting New Genetic Information into Mammalian Cells by Physical Techniques and Viral Vectors," Pharmac. Thera., 1985, 29, 69-92.
Daemen, F. J. M., "Vertebrate Rod Outer Segment Membranes," Biochem. Biophys. Acta, 1973, 300, 255-288.
De la Salle, H., et al., "Homozygous human TAP peptide transporter mutation in HLA class I deficiency," Science, 1994, 265, 237-241.
Dean, M., et al., "Evolution of ATP-binding cassette transporter genes," Curr. Opin. Genet. & Dev., 1995, 5, 779-785.
Dean, M., et al., "Mapping and Sequencing of Two Yeast Genes Belonging to the ATP-Binding Cassette Superfamily," Yeast, 1994, 377-383.
Devereaux, J., et al., "A comprehensive set of sequence analysis programs for the VAX," Nucleic Acids Res., 1984, 12, 387-395.
Dowling, J. E., "Chemistry of Visual Adaptation in the Rat," Nature, 1960, 188, 114-118.
Dryja, T. P., et al., "Molecular genetics of retinitis pigmentosa," Hum. Mol. Genet., 4, 1995, 1739-1743.
Eagle, R. C. Jr., et al., "Retinal Pigment Epithelial Abnormalities in Fundus Flavimaculatus," Ophthalmology, 1980, 87, 1189-1200.
Feeney, L., "Lipofuscin and melanin of human retinal pigment epithelium," Invest. Ophthalmol. Vis. Sci., 1978, 17, 583-600.
Fishman, G. A., "Fundus Flavimaculatus," Arch. Ophthalmol , 1976, 94, 2061-2067.
Fong, S.-L., et al., "Purification and Characterization of a Retinol-binding Glycoprotein Synthesized and Secreted by Bovine Neural Retina," J. Biol. Chem., 1984, 259, 6534-6542.
Gass, J. D. M., "Stargardt's disease (Fundus Flavimaculatus)," Stereoscopic Atlas of Macular Diseases: Diagnosis and Treatment, 1987, vol. 1, 3rd edition, C. V. Mosby Company, St. Louis, MO, 256-261.
Gerber, S., et al., "A Gene for Late-Onset Fundus Flavimaculatus with Macular Dystrophy Maps to Chromosome 1p13," Am. J. Hum. Genet., 1995, 56, 396-399.
Gerber, S., et al., "Complete Exon-Intron structure of the retina-specific ATP binding transporter gene (ABCR) allows the identification of novel mutations underlying stargardt disease," Genomics, 1998, 48, 139-142.
Glavač, D., et al., "Optimization of the Single-Strand Conformation Polymorphism (SSCP) Technique for Detection of Point Mutations," Hum. Mutat., 1993, 2, 404-414.
Hayes, K. C., "Retinal degeneration in monkeys induced by deficiencies of vitamin E or A," Invest. Ophthalmology, 1974, 13, 499-510.
Hettema, E. H., et al., "The ABC transporter proteins Pat1 and Pat2 are required for import of long-chain fatty acids into peroxisomes of *Saccharomces cerevisiae*," EMBO J., 1996, 15, 3813-3822.
Hillier, L., et al., "ys81h09.r1 soares retina N2B4HR *Homo sapiens* cDNA clone IMAGE: 221249 5' similar to SP:C48B4.5 CE00488 ATP-binding transport protein; mRNA sequence," Database EMBL [Online] entry HS947245, Acc. No. H91947, Dec. 1, 1995, XP002191077, 1 page.
Hoyng, C. B., et al., "Genetic fine mapping of the gene for recessive Stargardt disease," Hum. Genet., 1996, 98, 500-504.
Hyde, S. C., et al., "Structural model of ATP-binding proteins associated with cystic fibrosis, multidrug resistance and bacterial transport," Nature, 1990, 346, 362-365.
Illing, M., et al., the 220-kDa rim protein of retinal rod outer segments is a member of the ABC transporter superfamily, J. of Biological Chem, 1997, 272(15), 10303-10310.
Klein, B. A., et al., "Fundus Flavimaculatus: Clinical, Functional and Histopathic Observations," Am. J. Ophthalmol., 1967, 64, 3-23.
Klugbauer, N., et al., "Primary structure of a novel ABC transporter with a chromosomal localization on the band encoding the multidrug resistance-associated protein," FEBS Letts., 1996, 391, 61-65.
Kuwano, Y., et al., "Molecular Cloning and Nucleotide Sequence of DNA Complementary to Rat Ribosomal Protein S26 Messenger RNA," J. Biochem., 1985, 97, 983-992.
Kwoh, D. Y.., et al., "Transcription-based amplification system and detection of amplified human immunodeficiency virus type 1 with a bead-based sandwich hybridization format," Proc. Natl. Acad. Sci. (U.S.A.), 1989, 86, 1173-1177.
Lopez, P. F., et al., "Autosomal-dominant Fundus Flavimaculatus: Clinicopathologic Correlation," Ophthalmology, 1990, 97, 798-809.
Luciani, M.-F., et al., "Cloning of Two Novel ABC Transporters Mapping of Human Chromosome 9," Genomics, 1994, 21, 150-159.
Luciani, M.-F., et al., The ATP binding cassette transporter ABC1, is required for the engulfment of corpses generated by apoptotic cell death, EMBO J., 1996, 15, 226-235.
McDonnell, P. J., et al., "Fundus Flavimaculatus without Maculopathy: A Clinicopathologic Study," Ophthalmology, 1986, 93, 116-119.
Meindl, A., et al., "Norrie disease is caused by mutations in an extracellular protein resembling C-terminal globular domain of mucins," Nature Genetics, 1992, 2, 139-143.
Meindl, A., et al., "A gene (RPGR) with homology to the RCC1 guanine nucleotide exchange factor is mutated in X-linked retinitis pigmentosa (RP3)," Nature Genetics, 1996, 13, 35-42.
Mosser, J., et al., "Putative X-linked adrenoleukodystrophy gene shares unexpected homology with transporters," Nature, 1993, 361, 726-730.
Nathans, J., et al., "Molecular Genetics of Human Color Vision: The Genes Enxoding Blue, Green and Red Pigments," Science, 1986, 232, 193-202.
Nasonkin, I., et al., "Mapping of the rod photoreceptor ABC transporter (ABCR) to 1p21-p22.1 and identification of novel mutations in Stargardt's disease," Hum. Genet, 1998, 102, 21-26, XP-002191075.
Nickells, R. W., et al., "Cloning and Characterization of Rod Opsin cDNA From the Old World Monkey, *Macaca fascicularis*," Investigative Ophthalmology and Visual Science, 1995, 36, 72-82.
Noble, K. G., et al., "Stargardt's Disease and Fundus Flavimaculatus," Arch Ophthalmol., 1979, 97, 1281-1285.
Rando, R. R., "The Chemistry of Vitamin and Vision" Angew. Chem. Int. Ed. Engl., 1990, 29, 461-480.
Riordan, J. R., et al., "Identification of the Cystic Fibrosis Gene: Cloning and characterization of Complementary DNA," Science, 1989, 245, 1066-1073.
Roa, B. B., et al., "Charcot-Marie-Tooth Disease Type 1A: Association with a Spontaneous Point Mutation in the PMP22 Gene," New Eng. J. Med., 1993, 329, 96-101.
Roa, B. B., et al., "Myelin Protein Zero (MPZ) Gene Mutations in Nonduplication Type 1 Charcot-Marie-Tooth Disease," Hum. Mut., 1996, 7, 36-45.
Rowe, L. B., et al., "Maps from two interspecific backcross DNA panels available as a community genetic mapping resource," Mammalian Genome, 1994, 5, 253-274.
Seabra, M. C., et al., "Retinal Degeneration in Choroideremia: Deficiency of Rab Geranylgeranyl Transferase," Science 1993, 259, 377-381.
Shani, N., et al., "A *Saccharaomyces cerevisiae* homolog of the human adrenoleukodystrophy transporter is a heterodimer of two half ATP-binding cassette transporters," Proc. Natl. Acad. Sci. (U.S.A.), 1996, 93, 11901-11906.
Shimozawa, N., et al., "A Human Gene Responsible for Zellweger Syndrome That Affects Peroxosome Assembly," Science, 1992, 255, 1132-1134.
Smit, J. J. M., et al., "Homozygous Disruption of the Murine mdr2 P-Glycoprotein Gene Leads to a Complete Absence of Phospholipid from Bile and to Liver Disease," Cell, 1993, 75, 451-462.
Steinmetz, R. L., et al., "Histopathology of Incipient Fundus Flavimaculatus," Ophthalmology, 1991, 98, 953-956.
Stone, E. M., et al., "Clinical Features of a Stagardt-Like Dominant Progressive Macular Dystrophy With Genetic Linkage to Chromosome 6q," Arch Ophthalmol., 1994, 112, 765-772.
Sun, H. et al., "Stargardt's ABCR is localized to the disc membrane of retinal rod outer segments," Nature Genetics, 1997, 17, 15-16.

Thomas, P. M., et al., "Mutations in the Sulfonylurea Receptor Gene in Familial Persistent Hyperindulinemic Hypoglycemia of Infancy," Science, 1995, 268, 426-429.
Valle, D., et al., "The Hyperomithinemias," The Metabolic and Molecular Basis of Inherited Disease, Scriver, C. R. et al., eds., 1995, New York: McGraw Hill, Chapter 31, 1147-1185.
van Helvoort, A., et al., "MDR1 P-Glycoprotein Is a Lipid Translocase of Broad Specificity, While MDR3 P-Glycoprotein Specifically Translocates Phosphatidylcholine," Cell, 1996, 87, 507-517.
Wang, Y., et al., "A Large Family of Putative Transmembrane Receptors Homologous to the Product of the Drosophila Tissue Polarity Gene frizzled," J. Biol. Chem., 1996, 271, 4468-4476.
Warner, L. E., et al., "Clinical Phenotypes of Different Mpz ($P_0$) Mutations May Include Charcot-Marie-Tooth Type 1B, Dejerine-Sottas, and Congenital Hypomyelination," Neuron, 1996, 17, 451-460.
Weber, B. H. F., et al., "Mutations in the tissue inhibitor of metalloproteinases-3 (TIMP3) in patients with Sorsby's fundus dystrophy," Nat. Genet., 1994, 8, 352-356.
Weiter, J. J et al., "Retinal Pigment Epithelial Lipofuscin and Melanin and Choroidal Melanin in human eyes," Invest. Ophthalmol. & Vis. Sci., 1986, 27, 145-152.
Wing, G. L., et al., "The topography and age relationship of lipofuscin concentration in the retinal pigment epithelium," Invest. Ophthalmol & Vis. Sci., 1978, 17, 601-607.
Zhang, K., et al., "A Dominant Stargardt's Macular Dystrophy Locus Maps to Chromosome 13q34," Arch. Ophthalmol., 1994, 112, 759-764.
Zhou, H., et al., "Retina-Derived POU-Domain Factor-1: A Complex POU-Domain Gene Implicated in the Development of Retinal Ganglion and Amacrine Cells," J. Neurosci., 1996, 16, 2261-2274.
Zinn, K.M., et al., *The Retinal Pigment Epithelium*, Harvard University Press, Cambridge, MA, 1979, p. 521.
Acland, G., et al., "Gene therapy restores vision in canine model of childhood blindness," Nat. Genet., 2001, 28, 92-95.
Borrá, T., "Recent developments in ocular gene therapy," Experimental Eye Res., 2003, 76, 643-652.
Brown, B.D., et al., "Dangerous liaisons: the role of "danger" signals in the immune response to gene therapy," Blood, 2002, 100(4), 133-1140.
Creamers, F.P.M., et al., "Autosomal recessive retinitis pigmentosa and cone-rod dystrophy caused by splice site mutations in the stargardt's disease ABCR," Human Molecular Genetics, 1998, 7(3), 355-362.
Dejneka, N., et al., "In utero gene therapy rescues vision in a murine model of congenital blindness," Mol. Ther., 2004, 9(2), 182-188.
Dean, M., et al., "The human ATP-binding cassettes (ABC) transporter superfamily," Genome Res., 2001, 11, 1156-1166.
Hamdi, K.H., et al., "Age-related macular degeneration: a new viewpoint," Frontiers in Bioscience, 2003, 8(e), e305-e314.
Hsu, S., et al., "glyceraldehydes-3 phosphate dehydrogenase in a major protein associated with the plasma membrane of retinal photoreceptor outer segments," The Journal of Biological Chemistry, 1990, 265, 13308-13313.
Jaakson, K., et al., "Genotyping microarray (gene chip) for the ABCR (ABCA4) gene," Human Mutation, 2003, 22, 395-403.
Juengst, B.M.J., "What next for human gene therapy?," Dept. of Biothics, School of Medicine, 2003, 326, 1410-1411.
Kong, J., et al., "Correction of the disease phenotype in the mouse model of stargardt disease by lentiviral gene therapy," (Abstract, 1 page) (published online at http://www.arvo.org/eweb/as 2005 Annual Meeting abstract).
Liggett, T.E., et al., "Production of a plasmid for the stable transfection of the human ABCA-4 gene into mammalian cell line," 2005 © 2005, Association for Research in Vision and Opthalmology, Inc., (Abstract, 1 page).
Mallam, J.N., et al., "In vitro adenovirus-mediated delivery of the large ABCA4 transgene is enhanced in a simulated ocular environment," 2004 © 2004, Association for Research in Vision and Opthalmology, Inc., (Abstract, 1 page).
Molday, L.L., et al., "ABCR expression in foveal cone photoreceptors and its role in stargardt macular dystrophy," Nat. Genet, 2000, 25(3), 257-258.
New England Biolabs product #1230, Catalog 1988-1998, 1 page.
Ngo, J.T., et al., "Computational complexity, protein structure prediction, and the levinthal paradox," *The Protein Folding Problem and Tertiary Structure Prediction*, Merz, K., et al. (Eds.), Birkhauser Boston, Boston, MA, 1994, 433, 492-495.
Remers, F.P.M., et al., "Autosomal recessive retinitis pigmentosa and cone-rod dystrophy caused by splice site mutations in the stargardt's disease gene ABCR," Human Molecular Genetics, 1998, 7(3), 355-362.
Roller, A.B., et al., "Gene therapy for the abcr-mouse-model of stargardt's macular degeneration using recombinant adeno-and adeno-associated viral vectors," 2004 ©2004, Association for Research in Vision and Opthalmology, Inc. (Abstract, 1 page).
Rosenberg, L.E., et al., "Gene therapist, heal thyself," Science, 2000, 287, p. 1751.
Rozet, J.M., et al., "Spectrum of ABCR gene mutations in autosomal recessive macular dystrophies," Eur. J. Hum. Genet, 1998, 6(3), 291-295.
Rudinger, J., "Characteristics of the amino acids as components of a peptide hormone sequence," Peptide Hormones, Parsons, J.A. (Ed.), University Park Press, Baltimore, MD, 1976, 1-7.
Touchette, N., "Gene therapy: not ready for prime time," Nat. Med., 1996, 2(1) 7-8.
Verma, I.M., et al., "Gene therapy—promises, problems and prospects," Nature, 1997, 389, 239-242.
Weng, J., et al., "Insights into the function of rim protein in photoreceptors and etiology of stargardt's disease from the phenotype in abrc knockout mice," Cell, 1999, 98, 13-23.
Zack, D.J., et al., "What can we learn about AMD from other retinal diseases?," Mol. Vision, 1999, 5, 30-38.
Atlschul, S. F., et al., "Basic Local Alignment Search Tool," *J. Mol. Biol.*, 1990, 215, 403-410.
Bellanne-Chantelot, C., et al., "Mapping the Whole Human Genome by Fingerprinting Yeast Artificial Chromosomes," *Cell*, 1992, 70, 1059-1068.
Boguski, M. S., et al., "dbEST—database for 'expressed sequence tags,'" *Nature Genet*, 1993, 4, 332-333.
Bradley, A., "Production and Analysis of Chimeric Mice," *Teratocarcinomas and Embryonic Stem Cells—A Practical Approach*, 1987, Roberson (Ed.), *IRL Press*, 113-151.
Chomczynski, P., et al., "Single-Step method of RNA Isolation by Acid Guanidinium Thiocyanate-Phenol-Chloroform Extraction," *Analyt. Biochem.*, 1987, 162, 156-159.
Dean, M., et al., "The human ATP-binding cassette (ABC) transporter superfamily," Genome Res., 2001, 11(7), 1156-1166.
Feng, D.-F., et al., "Progressive Sequence Alignment as a Prerequisite to Correct Phylognetic Trees," *J. Mol. Evol.*, 1987, 25, 351-360.
Hsu, S-C. et al., "Glyceraldehyde-3-phosphate Dehydrogenase is a Major Protein Associated with the Plasma Membrane of Retinal Photoreceptor Outer Segments," *The Journal of Biological Chemistry*, 1990, 265(22), 13308-13313.
Lennon, G., et al., "The I.M.A.G.E. Consortium: An Integrated Molecular Analysis of Genomes and Their Expression," *Genomics*, 1996, 33, 151-152.
Maxam, et al., *Proc. Natl. Acad. Sci.*, 1977, 74, 560-564.
Orita, M., et al., "Rapid and Sensitive Detection of Point Mutations and DNA Polymorphisms Using the Polymerase Chain Reaction," Genomics, 1989, 5, 874-879.
PTO SEQ search report for AN-HSU88667, 1997.
Rudinger, Peptide Hormones, Parsons (Ed), University park press, Baltimore, MD, 1976, 1-7.

* cited by examiner

```
      -580                    -560                   -540
CCCCTACCCCTCTGCTAAGCTCAGGGATAACCCAACTAGCTGACCATAATGACTTCAGTC
      -520                    -500                   -480
ATTACGGAGCAAGATGAAAGACTAAAAGAGGGAGGGATCACTTCAGATCTGCCGAGTGAG
      -460                    -440                   -420
TCGATTGGACTTAAAGGGCCAGTCAAACCCTGACTGCCGGCTCATGGCAGGCTCTTGCCG
      -400                    -380                   -360
AGGACAAATGCCCAGCCTATATTTATGCAAAGAGATTTTGTTCCAAACTTAAGGTCAAAG
      -340                    -320                   -300
ATACCTAAAGACATCCCCCTCAGGAACCCCTCTCATGGAGGAGAGTGCCTGAGGGTCTTG
      -280                    -260                   -240
GTTTCCCATTGCATCCCCCACCTCAATTTCCCTGGTGCCCAGCCACTTGTGTCTTTAGGG
      -220                    -200                   -180
TTCTCTTTCTCTCCATAAAAGGGAGCCAACACAGTGTCGGCCTCCTCTCCCCAACTAAGG
      -160                    -140                   -120
GCTTATGTGTAATTAAAAGGGATTATGCTTTGAAGGGGAAAAGTAGCCTTTAATCACCAG
      -100                     -80                    -60
GAGAAGGACACAGCGTCCGGAGCCAGAGGCGCTCTTAACGGCGTTTATGTCCTTTGCTGT
       -40                     -20                      0
CCTGAGGGGCCTCAGCTCTGACCAATCTGGTCTTCGTGTGGTCATTAGCATGGGCTTCGT
                                                   M  G  F  V
       20                      40                     60
GAGACAGATACAGCTTTTGCTCTGGAAGAACTGGACCCTGCGGAAAAGGCAAAAGATTCG
 R  Q  I  Q  L  L  L  W  K  N  W  T  L  R  K  R  Q  K  I  R
       80                     100                    120
CTTTGTGGTGGAACTCGTGTGGCCTTTATCTTTATTTCTGGTCTTGATCTGGTTAAGGAA
 F  V  V  E  L  V  W  P  L  S  L  F  L  V  L  -  W  L  R  N
      140                     160                    180
TGCCAACCCGCTCTACAGCCATCATGAAT|GCCATTTCCCCAACAAGGCGATGCCCTCAGC
 A  N  P  L  Y  S  H  H  E  C    H  F  P  N  K  A  M  P  S  A
      200                     220                    240
AGGAATGCTGCCGTGGCTCCAGGGGATCTTCTGCAATGTGAACAATCCCTGTTTTCAAAG
 G  M  L  P  W  L  Q  G  I  F  C  N  V  N  N  P  C  F  Q  S
      260                     280                    300
CCCCACCCCAGGAGAATCTCCTGGAATTGTGTCAAACTATAACAACTCCAT|CTTGGCAAG
 P  T  P  G  E  S  P  G  I  V  S  N  Y  N  N  S  I    L  A  R
      320                     340                    360
GGTATATCGAGATTTTCAAGAACTCCTCATGAATGCACCAGAGAGCCAGCACCTTGGCCG
 V  Y  R  D  F  Q  E  L  L  M  N  A  P  E  S  Q  H  L  G  R
      380                     400                    420
TATTTGGACAGAGCTACACATCTTGTCCCAATTCATGGACACCCTCCGGACTCACCCGGA
 I  W  T  E  L  H  I  L  S  Q  F  M  D  T  L  R  T  H  P  E
      440                     460                    480
GAGAATTGCAG|GAAGAGGAATACGAATAAGGGATATCTTGAAAGATGAAGAAACACTGAC
 R  I  A  G    R  G  I  R  I  R  D  I  L  K  D  E  E  T  L  T
      500                     520                    540
ACTATTTCTCATTAAAAACATCGGCCTGTCTGACTCAGTGGTCTACCTTCTGATCAACTC
 L  F  L  I  K  N  I  G  L  S  D  S  V  V  Y  L  L  I  N  S
```

FIG. 3A

```
       560                          580                            600
TCAAGTCCGTCCAGAGCAG|TTCGCTCATGGAGTCCCGGACCTGGCGCTGAAGGACATCGC
 Q  V  R  P  E  Q   F  A  H  G  V  P  D  L  A  L  K  D  I  A
       620                          640                            660
CTGCAGCGAGGCCCTCCTGGAGCGCTTCATCATCTTCAGCCAGAGACGCGGGGCAAAGAC
 C  S  E  A  L  L  E  R  F  I  I  F  S  Q  R  R  G  A  K  T
       680                          700                            720
GGTGCGCTATGCCCTGTGCTCCCTCTCCCAGGGCACCCTACAGTGGATAGAAGACACTCT
 V  R  Y  A  L  C  S  L  S  Q  G  T  L  Q  W  I  E  D  T  L
       740                          760                            780
GTATGCCAACGTGGACTTCTTCAAGCTCTTCCGTGTG|CTTCCCACACTCCTAGACAGCCG
 Y  A  N  V  D  F  F  K  L  F  R  V   L  P  T  L  L  D  S  R
       800                          820                            840
TTCTCAAGGTATCAATCTGAGATCTTGGGGAGGAATATTATCTGATATGTCACCAAGAAT
 S  Q  G  I  N  L  R  S  W  G  G  I  L  S  D  M  S  P  R  I
       860                          880                            900
TCAAGAG|TTTATCCATCGGCCGAGTATGCAGGACTTGCTGTGGGTGACCAGGCCCCTCAT
 Q  E   F  I  H  R  P  S  M  Q  D  L  L  W  V  T  R  P  L  M
       920                          940                            960
GCAGAATGGTGGTCCAGAGACCTTTACAAAGCTGATGGGCATCCTGTCTGACCTCCTGTG
 Q  N  G  G  P  E  T  F  T  K  L  M  G  I  L  S  D  L  L  C
       980                         1000                           1020
TGGCTACCCCGAGGGAGGTGGCTCTCGGGTGCTCTCCTTCAACTGGTATGAAGACAATAA
 G  Y  P  E  G  G  G  S  R  V  L  S  F  N  W  Y  E  D  N  N
      1040                         1060                           1080
CTATAAGGCCTTTCTGGGGATTGACTCCACAAGGAAGGATCCTATCTATTCTTATGACAG
 Y  K  A  F  L  G  I  D  S  T  R  K  D  P  I  Y  S  Y  D  R
      1100                         1120                           1140
AAGAACAA|CATCCTTTTGTAATGCATTGATCCAGAGCCTGGAGTCAAATCCTTTAACCAA
 R  T  T   S  F  C  N  A  L  I  Q  S  L  E  S  N  P  L  T  K
      1160                         1180                           1200
AATCGCTTGGAGGGCGGCAAAGCCTTTGCTGATGGGAAAAATCCTGTACACTCCTGATTC
 I  A  W  R  A  A  K  P  L  L  M  G  K  I  L  Y  T  P  D  S
      1220                         1240                           1260
ACCTGCAGCACGAAGGATACTGAAGAAT|GCCAACTCAACTTTTGAAGAACTGGAACACGT
 P  A  A  R  R  I  L  K  N   A  N  S  T  F  E  E  L  E  H  V
      1280                         1300                           1320
TAGGAAGTTGGTCAAAGCCTGGGAAGAAGTAGGGCCCCAGATCTGGTACTTCTTTGACAA
 R  K  L  V  K  A  W  E  E  V  G  P  Q  I  W  Y  F  F  D  N
      1340                         1360                           1380
CAGCACACAGATGAACATGATCAGA|GATACCCTGGGGAACCCAACAGTAAAAGACTTTTT
 S  T  Q  M  N  M  I  R   D  T  L  G  N  P  T  V  K  D  F  L
      1400                         1420                           1440
GAATAGGCAGCTTGGTGAAGAAGGTATTACTGCTGAAGCCATCCTAAACTTCCTCTACAA
 N  R  Q  L  G  E  E  G  I  T  A  E  A  I  L  N  F  L  Y  K
      1460                         1480                           1500
GGGCCCTCGGGAAAGCCAGGCTGACGACATGGCCAACTTCGACTGGAGGGACATATTTAA
 G  P  R  E  S  Q  A  D  D  M  A  N  F  D  W  R  D  I  F  N
      1520                         1540                           1560
CATCACTGATCGCACCCTCCGCCTGGTCAATCAATACCTGGAG|TGCTTGGTCCTGGATAA
 I  T  D  R  T  L  R  L  V  N  Q  Y  L  E   C  L  V  L  D  K
```

FIG. 3B

```
     1580                1600                1620
GTTTGAAAGCTACAATGATGAAACTCAGCTCACCCAACGTGCCCTCTCTCTACTGGAGGA
 F  E  S  Y  N  D  E  T  Q  L  T  Q  R  A  L  S  L  L  E  E
     1640                1660                1680
AAACATGTTCTGGGCCGGAGTGGTATTCCCTGACATGTATCCCTGGACCAGCTCTCTACC
 N  M  F  W  A  G  V  V  F  P  D  M  Y  P  W  T  S  S  L  P
     1700                1720                1740
ACCCCACGTGAAGTATAAGATCCGAATGGACATAGACGTGGTGGAGAAAACCAATAAGAT
 P  H  V  K  Y  K  I  R  M  D  I  D  V  V  E  K  T  N  K  I
     1760                1780                1800
TAAAGACAG|GTATTGGGATTCTGGTCCCAGAGCTGATCCCGTGGAAGATTTCCGGTACAT
 K  D  R   Y  W  D  S  G  P  R  A  D  P  V  E  D  F  R  Y  I
     1820                1840                1860
CTGGGGCGGGTTTGCCTATCTGCAGGACATGGTTGAACAGGGGATCACAAGGAGCCAGGT
 W  G  G  F  A  Y  L  Q  D  M  V  E  Q  G  I  T  R  S  Q  V
     1880                1900                1920
GCAGGCGGAGGCTCCAGTTGGAATCTACCTCCAGCAGATGCCCTACCCCTGCTTCGTGGA
 Q  A  E  A  P  V  G  I  Y  L  Q  Q  M  P  Y  P  C  F  V  D
     1940                1960                1980
CGATTC|TTTCATGATCATCCTGAACCGCTGTTTCCCTATCTTCATGGTGCTGGCATGGAT
 D  S   F  M  I  I  L  N  R  C  F  P  I  F  M  V  L  A  W  I
     2000                2020                2040
CTACTCTGTCTCCATGACTGTGAAGAGCATCGTCTTGGAGAAGGAGTTGCGACTGAAGGA
 Y  S  V  S  M  T  V  K  S  I  V  L  E  K  E  L  R  L  K  E
     2060                2080                2100
GACCTTGAAAAATCAGGGTGTCTCCAATGCAGTGATTTGGTGTACCTGGTTCCTGGACAG
 T  L  K  N  Q  G  V  S  N  A  V  I  W  C  T  W  F  L  D  S
     2120                2140                2160
CTTCTCCATCATGTCGATGAGCATCTTCCTCCTGACGATATTCATCATGCATG|GAAGAAT
 F  S  I  M  S  M  S  I  F  L  L  T  I  F  I  M  H  G   R  I
     2180                2200                2220
CCTACATTACAGCGACCCATTCATCCTCTTCCTGTTCTTGTTGGCTTTCTCCACTGCCAC
 L  H  Y  S  D  P  F  I  L  F  L  F  L  L  A  F  S  T  A  T
     2240                2260                2280
CATCATGCTGTGCTTTCTGCTCAGCACCTTCTTCTCCAAGGCCAGTCTGGCAGCAGCCTG
 I  M  L  C  F  L  L  S  T  F  F  S  K  A  S  L  A  A  A  C
     2300                2320                2340
TAGTGGTGTCATCTATTTCACCCTCTACCTGCCACACATCCTGTGCTTCGCCTGGCAGGA
 S  G  V  I  Y  F  T  L  Y  L  P  H  I  L  C  F  A  W  Q  D
     2360                2380                2400
CCGCATGACCGCTGAGCTGAAGAAGGCTGTG|AGCTTACTGTCTCCGGTGGCATTTGGATT
 R  M  T  A  E  L  K  K  A  V   S  L  L  S  P  V  A  F  G  F
     2420                2440                2460
TGGCACTGAGTACCTGGTTCGCTTTGAAGAGCAAGGCCTGGGGCTGCAGTGGAGCAACAT
 G  T  E  Y  L  V  R  F  E  E  Q  G  L  G  L  Q  W  S  N  I
     2480                2500                2520
CGGGAACAGTCCCACGGAAGGGGACGAATTCAGCTTCCTGCTGTCCATGCAGATGATGCT
 G  N  S  P  T  E  G  D  E  F  S  F  L  L  S  M  Q  M  M  L
     2540                2560                2580
CCTTGATGCTGCGTGCTATGGCTTACTCGCTTGGTACCTTGATCAGGTGTTTCCAG|GAGA
 L  D  A  A  C  Y  G  L  L  A  W  Y  L  D  Q  V  F  P  G   D
```

FIG. 3C

```
      2600                      2620                      2640
CTATGGAACCCCACTTCCTTGGTACTTTCTTCTACAAGAGTCGTATTGGCTTAGCGGTGA
 Y  G  T  P  L  P  W  Y  F  L  L  Q  E  S  Y  W  L  S  G  E
      2660                      2680                      2700
AG|GGTGTTCAACCAGAGAAGAAAGAGCCCTGGAAAAGACCGAGCCCCTAACAGAGGAAAC
 G  C  S  T  R  E  E  R  A  L  E  K  T  E  P  L  T  E  E  T
      2720                      2740                      2760
GGAGGATCCAGAGCACCCAGAAGGAATACACG|ACTCCTTCTTTGAACGTGAGCATCCAGG
 E  D  P  E  H  P  E  G  I  H  D  S  F  F  E  R  E  H  P  G
      2780                      2800                      2820
GTGGGTTCCTGGGGTATGCGTGAAGAATCTGGTAAAGATTTTTGAGCCCTGTGGCCGGCC
 W  V  P  G  V  C  V  K  N  L  V  K  I  F  E  P  C  G  R  P
      2840                      2860                      2880
AGCTGTGGACCGTCTGAACATCACCTTCTACGAGAACCAGATCACCGCATTCCTGGGCCA
 A  V  D  R  L  N  I  T  F  Y  E  N  Q  I  T  A  F  L  G  H
      2900                      2920                      2940
CAATGGAGCTGGGAAAACCACCACCTT|GTCCATCCTGACGGGTCTGTTGCCACCAACCTC
 N  G  A  G  K  T  T  T  L  S  I  L  T  G  L  L  P  P  T  S
      2960                      2980                      3000
TGGGACTGTGCTCGTTGGGGGAAGGGACATTGAAACCAGCCTGGATGCAGTCCGGCAGAG
 G  T  V  L  V  G  G  R  D  I  E  T  S  L  D  A  V  R  Q  S
      3020                      3040                      3060
CCTTGGCATGTGTCCACAGCACAACATCCTGTTCCACCA|CCTCACGGTGGCTGAGCACAT
 L  G  M  C  P  Q  H  N  I  L  F  H  H  L  T  V  A  E  H  M
      3080                      3100                      3120
GCTGTTCTATGCCCAGCTGAAAGGAAAGTCCCAGGAGGAGGCCCAGCTGGAGATGGAAGC
 L  F  Y  A  Q  L  K  G  K  S  Q  E  E  A  Q  L  E  M  E  A
      3140                      3160                      3180
CATGTTGGAGGACACAGGCCTCCACCACAAGCGGAATGAAGAGGCTCAGGACCTATCAG|G
 M  L  E  D  T  G  L  H  H  K  R  N  E  E  A  Q  D  L  S  G
      3200                      3220                      3240
TGGCATGCAGAGAAAGCTGTCGGTTGCCATTGCCTTTGTGGGAGATGCCAAGGTGGTGAT
 G  M  Q  R  K  L  S  V  A  I  A  F  V  G  D  A  K  V  V  I
      3260                      3280                      3300
TCTGGACGAACCCACCTCTGGGGTGGACCCTTACTCGAGACGCTCAATCTGGGATCTGCT
 L  D  E  P  T  S  G  V  D  P  Y  S  R  R  S  I  W  D  L  L
      3320                      3340                      3360
CCTGAAGTATCGCTCAG|GCAGAACCATCATCATGCCCACTCACCACATGGACGAGGCCGA
 L  K  Y  R  S  G  R  T  I  I  M  P  T  H  H  M  D  E  A  D
      3380                      3400                      3420
CCACCAAGGGGACCGCATTGCCATCATTGCCCAGGGAAGGCTCTACTGCTCAGGCACCCC
 H  Q  G  D  R  I  A  I  I  A  Q  G  R  L  Y  C  S  G  T  P
      3440                      3460                      3480
ACTCTTCCTGAAGAACTGCTTTGGCACAGGCTTGTACTTAACCTTGGTGCGCAAGATGAA
 L  F  L  K  N  C  F  G  T  G  L  Y  L  T  L  V  R  K  M  K
      3500                      3520                      3540
AAACATCCAGAGCCAAAGGAAAGGCAGTGAG|GGGACCTGCAGCTGCTCGTCTAAGGGTTT
 N  I  Q  S  Q  R  K  G  S  E  G  T  C  S  C  S  S  K  G  F
      3560                      3580                      3600
CTCCACCACGTGTCCAGCCCACGTCGATGACCTAACTCCAGAACAAGTCCTGGATGGGGA
 S  T  T  C  P  A  H  V  D  D  L  T  P  E  Q  V  L  D  G  D
```

FIG. 3D

```
       3620                3640                3660
TGTAAATGAGCTGATGGATGTAGTTCTCCACCATGTTCCAGAGGCAAAGCTGGTGGAGTG
 V  N  E  L  M  D  V  V  L  H  H  V  P  E  A  K  L  V  E  C
       3680                3700                3720
CATTGGTCAAGAACTTATCTTCCTTCTTCCAAATAAGAACTTCAAGCACAGAGCATATGC
 I  G  Q  E  L  I  F  L  L  P  N  K  N  F  K  H  R  A  Y  A
       3740                3760                3780
CAGCCTTTTCAGAGAGCTGGAGGAGACGCTGGCTGACCTTGGTCTCAGCAGTTTTGGAAT
 S  L  F  R  E  L  E  E  T  L  A  D  L  G  L  S  S  F  G  I
       3800                3820                3840
TTCTGACACTCCCCTGGAAGAG|ATTTTTCTGAAGGTCACGGAGGATTCTGATTCAGGACC
 S  D  T  P  L  E  E   I  F  L  K  V  T  E  D  S  D  S  G  P
       3860                3880                3900
TCTGTTTGCGG|GTGGCGCTCAGCAGAAAAGAGAAAACGTCAACCCCCGACACCCCTGCTT
 L  F  A  G   G  A  Q  Q  K  R  E  N  V  N  P  R  H  P  C  L
       3920                3940                3960
GGGTCCCAGAGAGAAGGCTGGACAGACACCCCAGGACTCCAATGTCTGCTCCCCAGGGGC
 G  P  R  E  K  A  G  Q  T  P  Q  D  S  N  V  C  S  P  G  A
       3980                4000                4020
GCCGGCTGCTCACCCAGAGGGCCAGCCTCCCCCAGAGCCAGAGTGCCCAGGCCCGCAGCT
 P  A  A  H  P  E  G  Q  P  P  P  E  P  E  C  P  G  P  Q  L
       4040                4060                4080
CAACACGGGGACACAGCTGGTCCTCCAGCATGTGCAGGCGCTGCTGGTCAAGAGATTCCA
 N  T  G  T  Q  L  V  L  Q  H  V  Q  A  L  L  V  K  R  F  Q
       4100                4120                4140
ACACACCATCCGCAGCCACAAGGACTTCCTGGCGCAG|ATCGTGCTCCCGGCTACCTTTGT
 H  T  I  R  S  H  K  D  F  L  A  Q   I  V  L  P  A  T  F  V
       4160                4180                4200
GTTTTTGGCTCTGATGCTTTCTATTGTTATCCTTCCTTTTGGCGAATACCCCGCTTTGAC
 F  L  A  L  M  L  S  I  V  I  L  P  F  G  E  Y  P  A  L  T
       4220                4240                4260
CCTTCACCCCTGGATATATGGGCAGCAGTACACCTTCTTCAG|CATGGATGAACCAGGCAG
 L  H  P  W  I  Y  G  Q  Q  Y  T  F  F  S   M  D  E  P  G  S
       4280                4300                4320
TGAGCAGTTCACGGTACTTGCAGACGTCCTCCTGAATAAGCCAGGCTTTGGCAACCGCTG
 E  Q  F  T  V  L  A  D  V  L  L  N  K  P  G  F  G  N  R  C
       4340                4360                4380
CCTGAAGGAAGGGTGGCTTCC|GGAGTACCCCTGTGGCAACTCAACACCCTGGAAGACTCC
 L  K  E  G  W  L  P   E  Y  P  C  G  N  S  T  P  W  K  T  P
       4400                4420                4440
TTCTGTGTCCCCAAACATCACCCAGCTGTTCCAGAAGCAGAAATGGACACAGGTCAACCC
 S  V  S  P  N  I  T  Q  L  F  Q  K  Q  K  W  T  Q  V  N  P
       4460                4480                4500
TTCACCATCCTGCAG|GTGCAGCACCAGGGAGAAGCTCACCATGCTGCCAGAGTGCCCCGA
 S  P  S  C  R   C  S  T  R  E  K  L  T  M  L  P  E  C  P  E
       4520                4540                4560
GGGTGCCGGGGGCCTCCCGCCCCCCCAG|AGAACACAGCGCAGCACGGAAATTCTACAAGA
 G  A  G  G  L  P  P  P  Q   R  T  Q  R  S  T  E  I  L  Q  D
```

FIG. 3E

```
       4580                      4600                      4620
CCTGACGGACAGGAACATCTCCGACTTCTTGGTAAAAACGTATCCTGCTCTTATAAGAAG
 L  T  D  R  N  I  S  D  F  L  V  K  T  Y  P  A  L  I  R  S
       4640                      4660                      4680
CAGC|TTAAAGAGCAAATTCTGGGTCAATGAACAGAG|GTATGGAGGAATTTCCATTGGAGG
 S   L  K  S  K  F  W  V  N  E  Q  R   Y  G  G  I  S  I  G  G
       4700                      4720                      4740
AAAGCTCCCAGTCGTCCCCATCACGGGGGAAGCACTTGTTGGGTTTTTAAGCGACCTTGG
 K  L  P  V  V  P  I  T  G  E  A  L  V  G  F  L  S  D  L  G
       4760                      4780                      4800
CCGGATCATGAATGTGAGCGGG|GGCCCTATCACTAGAGAGGCCTCTAAAGAAATACCTGA
 R  I  M  N  V  S  G   G  P  I  T  R  E  A  S  K  E  I  P  D
       4820                      4840                      4860
TTTCCTTAAACATCTAGAAACTGAAGACAACATTA|AGGTGTGGTTTAATAACAAAGGCTG
 F  L  K  H  L  E  T  E  D  N  I  K   V  W  F  N  N  K  G  W
       4880                      4900                      4920
GCATGCCCTGGTCAGCTTTCTCAATGTGGCCCACAACGCCATCTTACGGGCCAGCCTGCC
 H  A  L  V  S  F  L  N  V  A  H  N  A  I  L  R  A  S  L  P
       4940                      4960                      4980
TAAGGACAGGAGCCCCGAGGAGTATGGAATCACCGTCATTAGCCAACCCCTGAACCTGAC
 K  D  R  S  P  E  E  Y  G  I  T  V  I  S  Q  P  L  N  L  T
       5000                      5020                      5040
CAAGGAGCAGCTCTCAGAGATTACAGT|GCTGACCACTTCAGTGGATGCTGTGGTTGCCAT
 K  E  Q  L  S  E  I  T  V   L  T  T  S  V  D  A  V  V  A  I
       5060                      5080                      5100
CTGCGTGATTTTCTCCATGTCCTTCGTCCCAGCCAGCTTTGTCCTTTATTTGATCCAGGA
 C  V  I  F  S  M  S  F  V  P  A  S  F  V  L  Y  L  I  Q  E
       5120                      5140                      5160
GCGGGTGAACAAATCCAAGCACCTCCAGTTTATCAGTGGAGTGAGCCCCACCACCTACTG
 R  V  N  K  S  K  H  L  Q  F  I  S  G  V  S  P  T  T  Y  W
       5180                      5200                      5220
GGTGACCAACTTCCTCTGGGACATC|ATGAATTATTCCGTGAGTGCTGGGCTGGTGGTGGG
 V  T  N  F  L  W  D  I   M  N  Y  S  V  S  A  G  L  V  V  G
       5240                      5260                      5280
CATCTTCATCGGGTTTCAGAAGAAAGCCTACACTTCTCCAGAAAACCTTCCTGCCCTTGT
 I  F  I  G  F  Q  K  K  A  Y  T  S  P  E  N  L  P  A  L  V
       5300                      5320                      5340
GGCACTGCTCCTGCTGTATGG|ATGGGCGGTCATTCCCATGATGTACCCAGCATCCTTCCT
 A  L  L  L  L  Y  G   W  A  V  I  P  M  M  Y  P  A  S  F  L
       5360                      5380                      5400
GTTTGATGTCCCCAGCACAGCCTATGTGGCTTTATCTTGTGCTAATCTGTTCATCGGCAT
 F  D  V  P  S  T  A  Y  V  A  L  S  C  A  N  L  F  I  G  I
       5420                      5440                      5460
CAACAGCAGTGCTATTACCTTCATCTTGGAATTATTTGATAATAACCGG|ACGCTGCTCAG
 N  S  S  A  I  T  F  I  L  E  L  F  D  N  N  R   T  L  L  R
       5480                      5500                      5520
GTTCAACGCCGTGCTGAGGAAGCTGCTCATTGTCTTCCCCCACTTCTGCCTGGGCCGGGG
 F  N  A  V  L  R  K  L  L  I  V  F  P  H  F  C  L  G  R  G
```

FIG. 3F

```
      5540                5560                5580
CCTCATTGACCTTGCACTGAGCCAGGCTGTGACAGATGTCTATGCCCGGTTTG|GTGAGGA
 L  I  D  L  A  L  S  Q  A  V  T  D  V  Y  A  R  F  G   E  E
      5600                5620                5640
GCACTCTGCAAATCCGTTCCACTGGGACCTGATTGGGAAGAACCTGTTTGCCATGGTGGT
 H  S  A  N  P  F  H  W  D  L  I  G  K  N  L  F  A  M  V  V
      5660                5680                5700
GGAAGGGGTGGTGTACTTCCTCCTGACCCTGCTGGTCCAGCGCCACTTCTTCCTCTCCCA
 E  G  V  V  Y  F  L  L  T  L  L  V  Q  R  H  F  F  L  S  Q
      5720                5740                5760
ATG|GATTGCCGAGCCCACTAAGGAGCCCATTGTTGATGAAGATGATGATGTGGCTGAAGA
 W   I  A  E  P  T  K  E  P  I  V  D  E  D  D  D  V  A  E  E
      5780                5800                5820
AAGACAAAGAATTATTACTGGTGGAAATAAAACTGACATCTTAAGGCTACATGAACTAAC
 R  Q  R  I  I  T  G  G  N  K  T  D  I  L  R  L  H  E  L  T
      5840                5860                5880
CAAG|ATTTATCTGGGCACCTCCAGCCCAGCAGTGGACAGGCTGTGTGTCGGAGTTCGCCC
 K   I  Y  L  G  T  S  S  P  A  V  D  R  L  C  V  G  V  R  P
      5900                5920                5940
TGGAGAG|TGCTTTGGCCTCCTGGGAGTGAATGGTGCCGGCAAAACAACCACATTCAAGAT
 G  E   C  F  G  L  L  G  V  N  G  A  G  K  T  T  T  F  K  M
      5960                5980                6000
GCTCACTGGGGACACCACAGTGACCTCAGGGGATGCCACCGTAGCAGGCAAGAG|TATTTT
 L  T  G  D  T  T  V  T  S  G  D  A  T  V  A  G  K  S   I  L
      6020                6040                6060
AACCAATATTTCTGAAGTCCATCAAAATATGGGCTACTGTCCTCAGTTTGATGCAATCGA
 T  N  I  S  E  V  H  Q  N  M  G  Y  C  P  Q  F  D  A  I  D
      6080                6100                6120
TGAGCTGCTCACAGGACGAGAACATCTTTACCTTTATGCCCGGCTTCGAGGTGTACCAGC
 E  L  L  T  G  R  E  H  L  Y  L  Y  A  R  L  R  G  V  P  A
      6140                6160                6180
AGAAGAAATCGAAAAG|GTTGCAAACTGGAGTATTAAGAGCCTGGGCCTGACTGTCTACGC
 E  E  I  E  K   V  A  N  W  S  I  K  S  L  G  L  T  V  Y  A
      6200                6220                6240
CGACTGCCTGGCTGGCACGTACAGTGGGGGCAACAAGCGGAAACTCTCCACAGCCATCGC
 D  C  L  A  G  T  Y  S  G  G  N  K  R  K  L  S  T  A  I  A
      6260                6280                6300
ACTCATTGGCTGCCCACCGCTGGTGCTGCTG|GATGAGCCCACCACAGGGATGGACCCCCA
 L  I  G  C  P  P  L  V  L  L   D  E  P  T  T  G  M  D  P  Q
      6320                6240                6360
GGCACGCCGCATGCTGTGGAACGTCATCGTGAGCATCATCAGAAAAGGGAGGGCTGTGGT
 A  R  R  M  L  W  N  V  I  V  S  I  I  R  K  G  R  A  V  V
      6380                6400                6420
CCTCACATCCCACAG|CATGGAAGAATGTGAGGCACTGTGTACCCGGCTGGCCATCATGGT
 L  T  S  H  S   M  E  E  C  E  A  L  C  T  R  L  A  I  M  V
      6440                6460                6480
AAAGGGCGCCTTTCGATGTATGGGCACCATTCAGCATCTCAAGTCCAA|ATTTGGAGATGG
 K  G  A  F  R  C  M  G  T  I  Q  H  L  K  S  K   F  G  D  G
      6500                6520                6540
CTATATCGTCACAATGAAGATCAAATCCCCGAAGGACGACCTGCTTCCTGACCTGAACCC
 Y  I  V  T  M  K  I  K  S  P  K  D  D  L  L  P  D  L  N  P
```

FIG. 3G

```
       6560                 6580                 6600
TGTGGAGCAGTTCTTCCAGGGGAACTTCCCAGGCAGTGTGCAGAGGGAGAGGCACTACAA
 V  E  Q  F  F  Q  G  N  F  P  G  S  V  Q  R  E  R  H  Y  N
       6620                 6640                 6660
CATGCTCCAGTTCCAGGTCTCCTCCTCCCTGGCGAGGATCTTCCAGCTCCTCCTCTC
 M  L  Q  F  Q  V  S  S  S  S  L  A  R  I  F  Q  L  L  L  S
       6680                 6700                 6720
CCACAAGGACAGCCTGCTCATCGAGGAGTACTCAGTCACACAGACCACACTGGACCAG|GT
 H  K  D  S  L  L  I  E  E  Y  S  V  T  Q  T  T  L  D  Q  V
       6740                 6760                 6780
GTTTGTAAATTTTGCTAAACAGCAGACTGAAAGTCATGACCTCCCTCTGCACCCTCGAGC
 F  V  N  F  A  K  Q  Q  T  E  S  H  D  L  P  L  H  P  R  A
       6800                 6820                 6840
TGCTGGAGCCAGTCGACAAGCCCAG|GACTGATCTTTCACACCGCTCGTTCCTGCAGCCAG
 A  G  A  S  R  Q  A  Q  D
       6860                 6880                 6900
AAAGGAACTCTGGGCAGCTGGAGGCGCAGGAGCCTGTGCCCATATGGTCATCCAAATGGA
       6920                 6940                 6960
CTGGCCCAGCGTAAATGACCCCACTGCAGCAGAAAACAAACACACGAGGAGCATGCAGCG
       6980                 7000                 7020
AATTCAGAAAGAGGTCTTTCAGAAGGAAACCGAAACTGACTTGCTCACCTGGAACACCTG
       7040                 7060                 7080
ATGGTGAAACCAAACAAATACAAAATCCTTCTCCAGACCCCAGAACTAGAAACCCCGGGC
       7100                 7120                 7140
CATCCCACTAGCAGCTTTGGCCTCCATATTGCTCTCATTTCAAGCAGATCTGCTTTTCTG
       7160                 7180
CATGTTTGTCTGTGTGTCTGCGTTGTGTGTGATTTTCATGGAAA
```

*FIG. 3H*

```
Abc1 M A C X P Q L R L L L W K N L T F R R R Q T C Q L L L E V A W P L F I F L I L I S V R L S Y P P Y E 50
ABCR M G F V R Q I Q L L L W K N W T L R K R Q K I R F V V E L V W P L S L F L V L I W L R N A N P L Y S 50
Abc2 . . . . . . . . . . . . . . . . . . . . . . . . . . . . . . . . . . . . . . . . . . . . . . . . . . 0
ABCC M A V L R Q L A L L L W K N Y T L Q K R K V L V T V L E L F L P L L F S G I L I W L R L K I Q S E N 50

Abc1 Q H E C H F P N K A M P S A G T L P W V Q G I I C N A N N P C F R Y P T P G E A P G V V G N F N K S 100
ABCR H H E C H F P N K A M P S A G M L P W L Q G I F C N V N N P C F Q S P T P G E S P G I V S N Y N N S 100
Abc2 . . . . . . . . . . . . . . . . . . . . . . . . . . . . . . . . . . . . . . . . . . . . . . . . . . 0
ABCC V P N A T I Y P G Q S I Q E L P L F F T F P P P G D T W E L A Y I P S H S D A A K T V T E T V R R A 100

Abc1 I V S R L F S D A Q R L L L Y S Q R D T S I K D M H K V L R M L R Q I K H . . . . . . . . . P N S N 141
ABCR I L A R V Y R D F Q E L L M N A P E S Q H L G R I W T E L H I L S Q F M D T L R T H P E R I A G R G 150
Abc2 . . . . . . . . . . . . . . . . . . . . . . . . . . . . . . . . . . . . . . . . . . . . . . . . . . 0
ABCC L V I N M R V R G F P S E K D F E D Y I R Y D N C S S S V L A A V V F E H P F N H S K E P L P L A V 150

Abc1 L K L Q D F L V D N E T F S G F L Q H N L S L P R S T V D S L L Q X N V G L Q K V F L Q G Y Q L H L 191
ABCR I R I R D I L K D E E T L T L F L I K N I G L S D S V V Y L L I N S Q V R P E Q F A H G V P D L A L 200
Abc2 . . . . . . . . . . . . . . . . . . . . . . . . . . . . . . . . . . . . . . . . . . . . . . . . . . 0
ABCC K Y H L R F S Y T R R N Y M W T Q T G S F F L K E T E G W H . . . . . . . . . . . . . . . . . . . . 180

Abc1 A S L . C N G S K L E E I I Q L G D A E V S . . . . . A L C G L P R K K L D A A E R V L R Y N M D I 235
ABCR K D I A C S E A L L E R F I I F S Q R R G A K T V R Y A L C S L S Q G T L Q W I E D T L Y A N V D F 250
Abc2 . . . . . . . . . . . . . . . . . . . . . . . . . . . . . . . . . . . . . . . . . . . . . . . . . . 0
ABCC . . . . . . . . . . . . . . . . . . . . . . . . . . . . . . . . . . . . . . . . . . . . . . . . . . 180

Abc1 L K . . . P V V T K L N S T S H L P T Q H L A E A T T V L L D S L G G L A Q E L F S T K S W S D M R 282
ABCR F K L F R V L P T L L D S R S Q G I N L R . . . S W G G I L S D M S P R I Q E F I H R P S M Q D L L 297
Abc2 . . . . . . . . . . . . . . . . . . . . . . . . . . . . . . . . . . . . . . . . . . . . . . . . . . 0
ABCC . . . . . . . . . . . . . . . . . . . . . . . . . . . . . . . . . . . . . . . . . . . . . . . . . . 180

Abc1 Q E V M F L T N V N S S S S S T Q I Y Q A V S R I V C G H P E G G G L K I K S L N W Y E D N N Y K A 332
ABCR W V T R P L M Q N G G P E T F T K L M G I L S D L L C G Y P E G G G S R V L S F N W Y E D N N Y K A 347
Abc2 . . . . . . . . . . . . . . . . . . . . . . . . . . . . . . . . . . . . . . . . . . . . . . . . . . 0
ABCC . . . . . . . . . . . . . . . . . . . . . . . . . . . . . . . . . . . . . . . . . . . . . . . . . . 180

Abc1 L F G G N N T E E D V D T F Y D N S T T P Y C N D L M K N L E S S P L S R I I W K A L K P L L V G K 382
ABCR F L G I D S T R K D P I Y S Y D R R T T S F C N A L I Q S L E S N P L T K I A W R A A K P L L M G K 397
Abc2 . . . . . . . . . . . . . . . . . . . . . . . . . . . . . . . . . . . . . . . . . . . . . . . . . . 0
ABCC . . . . . . . . . . . . . . . . . . . . . . . . . . . . . . . . . . . . . . . . . . . . . . . . . . 180

Abc1 I L Y T P D T P A T R Q V M A E V N K T F Q E L A V F H D L E G M W E E L S P Q I W T F M E N S Q E 432
ABCR I L Y T P D S P A A R R I L K N A N S T F E E L E H V R K L V K A W E E V G P Q I W Y F F D N S T Q 447
Abc2 . . . . . . . . . . . . . . . . . . . . . . . . . . . . . . . . . . . . . . . . . . . . . . . . . . 0
ABCC . . . . . . . . . . . . . . . . . . . . . . . . . . . . . . . . . . . . . . . . . . . . . . . . . . 180

Abc1 M D L V R T L L D S R G N D Q F W E Q K L D G L D W T A Q D I M A F L A K N P E D V Q S P N G S V Y 482
ABCR M N M I R D T L G N P T V K D F L N R Q L G E E G I T A E A I L N F L Y K G P R E S Q A D D M A N F 497
Abc2 . . . . . . . . . . . . . . . . . . . . . . . . . . . . . . . . . . . . . . . . . . . . . . . . . . 0
ABCC . . . . . . . . . . . . . . . . . . . . . . . . . . . . . . . . . . . . . . . . . . . . . . . . . . 180

Abc1 T W R E A F N E T N Q A I Q T I S R F M E C V N L N K L E P I P T E V R L I N K S M E L L D E R K F 532
ABCR D W R D I F N I T D R T L R L V N Q Y L E C L V L D K F E S Y N D E T Q L T Q R A L S L L E E N M F 547
Abc2 . . . . . . . . . . . . . . . . . . . . . . . . . . . . . . . . . . . . . . . . . . . . . . . . . . 0
ABCC . . . . . . . . . . . . . . . . . . . . . . . . . . . . . . . . . . . . . . . . . . . . . . . . . . 180

Abc1 W A G I V F T G I T P D S V E L P H H V K Y K I R M D I D N V E R T N K I K D G Y W D P G P R A D P 582
ABCR W A G V V F P D M Y P W T S S L P P H V K Y K I R M D I D V V E K T N K I K D R Y W D S G P R A D P 597
Abc2 . . . . . . . . . . . . . . . . . . . . . . . . . . . . . . . . . . . . . . . . . . . . . . . . . . 0
ABCC . . . . . . . . . . . . . . . . . . . . . . . . . . . . . . T T S L F P L F P N P G P R E P T 197
```

FIG. 4A

```
Abc1 F E D . . . M R Y V W G G F A Y L Q D V V E Q A I I R V L T G S E . . . . . K K T G V Y V Q Q M P Y 624
ABCR V E D . . . F R Y I W G G F A Y L Q D M V E Q G I T R S Q V Q A E . . . . . A P V G I Y L Q Q M P Y 639
Abc2 . . . . . . . . . . . . . . . . . . . . . . . . . . . . . . . . . . . . . . . . . . . . . . . . . . 0
ABCC S P D G G E P G Y I R E G F L A V Q H A V D R A I M E Y H A D A A T R Q L F Q R L T V T I K R F P Y 247

Abc1 P C Y V D D I F L R V M S R S M P L F M T L A W I Y S V A V I I K S I V Y E K E A R L K E T M R I M 674
ABCR P C F V D D S F M I I L N R C F P I F M V L A W I Y S V S M T V K S I V L E K E L R L K E T L K N Q 689
Abc2 . . . . . . . . . . . . . . . . . . . . . . . . . . . . . . . . . . . . . . . . . . . . . . . . . . 0
ABCC P P F I A D P F L V A I Q Y Q L P L L L L S F T Y T A L T I A R A V V Q E K E R R L K E Y M R M M 297

Abc1 G L D N G I L W F S W F V S S L I P L L V S A G L L V V I L . . . . . K L G N L L P Y S D P S V V F 719
ABCR G V S N A V I W C T W F L D S F S I M S M S I F L L T I F I . . . . . M H G R I L H Y S D P F I L F 734
Abc2 . . . . . . . . . . . . . . . . . . . . . . . . . . . . . . . . . . . . . . . . . . . . . . . . . . 0
ABCC G L S S W L H W S A W F L L F F L F L L I A A S F M T L L F C V K V K P N V A V L S R S D P S L V L 347

Abc1 V F L S V F A M V T I L Q C F L I S T L F S R A N L A A A C G G I I Y F T L Y L P Y V L C V A W Q D 769
ABCR L F L L A F S T A T I M L C F L L S T F F S K A S L A A A C S G V I Y F T L Y L P H I L C F A W Q D 784
Abc2 . . . . . . . . . . . . . . . . . . . . . . . . . . . . . . . . . . . . . . . . . . . . . . . . . . 0
ABCC A F L L C F A I S T I S F S F M V S T F F S K A N M A A A F G G F L Y F F T Y I P Y F F V A P R Y N 397

Abc1 Y V G F S I K I F A S L L S P V A F G F G C E Y F A L F E E Q G I G V Q W D N L F E S P V E E D G F 819
ABCR R M T A E L K K A V S L L S P V A F G F G T E Y L V R F E E Q G L G L Q W S N I G N S P T E G D E F 834
Abc2 . . . . . . . . . . . . . . . . . . . . . . . . . . . . . . . . . . . . . . . . . . . . . . . . . . 0
ABCC W M T L S Q K L C S C L L S N V A M A M G A Q L I G K F E A K G M G I Q W R D L L S P V N V D D D F 447

Abc1 N L T T A V S M M L F D T F L Y G V M T W Y I E A V F P G Q Y G I P R P W Y F P C T K S Y W F G E E 869
ABCR S F L L S M Q M M L L D A A C Y G L L A W Y L D Q V F P G D Y G T P L P W Y F L L Q E S Y W L S G E 884
Abc2 . . . . . . . . . . . . . . . . . . . . . . . . . . . . . . . . . . . . . . . . . . . . . . . . . . 0
ABCC C F G Q V L G M L L L D S V L Y G L V T W Y M E A V F P G Q F G V P Q P W Y F F I M P S Y W C G K P 497

Abc1 . . . . . . . . . . . . . . . I D E K S H P G S S Q K G V S E I C M E E E P T H L R L G V S I Q N L 904
ABCR G C S T R E E R A L E K T E P L T E E T E D P E H P E G I H D S F F E R E H P G W V P G V C V K N L 934
Abc2 . . . . . . . . . . . . . . . . . Q A C A M E S R H F E E T R G M E E E P T H L P L V V C V D K L 32
ABCC R A V A . . . . . . . . . . . . . G K E E E D S D P E K A L R N E Y F E A E P E D L V A G T K I K H L 535

Abc1 V K V Y R D G M K . . V A V D G L A L N F Y E G Q I T S F L G H N G A G K T T T M S I L T G L F P P 952
ABCR V K I F E P C G R . . P A V D R L N I T F Y E N Q I T A F L G H N G A G K T T T L S I L T G L L P P 982
Abc2 T K V Y K N D K K . . L A L N K L S L N L Y E N Q V V S F L G H N G A G K T T T M S I L T G L F P P 80
ABCC S K V F R V G N K D R A A V R D L N L N L Y E G Q I T V L L G H N G A G K T T T L S M L T G L F P P 585
                                                     A

Abc1 T S G T A Y I L G K D I R S E M S S I R Q N L G V C P Q H N V L F D M L T V E E H I W F Y A R L K G 1002
ABCR T S G T V L V G G R D I E T S L D A V R Q S L G M C P Q H N I L F H H L T V A E H M L F Y A Q L K G 1032
Abc2 T S G S A T I Y G H D I R T E M D E I R K N L G M C P Q H N V L F D R L T V E E H L W F Y S R L K S 130
ABCC T S G R A Y I S G Y E I S Q D M V Q I R K S L G L C P Q H D I L F D N L T V A E H L Y F Y A Q L K G 635

Abc1 L S E K H V K A E M E Q M A L D V G L P P S K L K S K T S Q L S G G M Q R K L S V A L A F V G G S K 1052
ABCR K S Q E E A Q L E M E A M L E D T G L H H . K R N E E A Q D L S G G M Q R K L S V A I A F V G D A K 1081
Abc2 M A Q E E I R K E T D K M I E D L E L S N . K R H S L V Q T L S G G M K R K L S V A I A F V G G S R 179
ABCC L S R Q K C P E E V K Q M L H I I G L E D . K W N S R S R F L S G G M R R K L S I G I A L I A G S K 684
                                                               C

Abc1 V V I L D E P T A G V D P Y S R R G I W E L L L K Y R Q G R T I I L S T H H M D E A D I L G D R I A 1102
ABCR V V I L D E P T S G V D P Y S R R S I W D L L L K Y R S G R T I I M S T H H M D E A D H Q G D R I A 1131
Abc2 A I I L D E P T A G V D P Y A R R A I W D L I L K Y K P G R T I I L S T H H M D E A D L L G D R I A 229
ABCC V L I L D E P T S G M D A I S R R A I W D L L Q R Q K S D R T I V L T T H F M D E A D L L G D R I A 734
             B

Abc1 I I S H G K L C C V G S S L F L K N Q L G T G Y Y L T L V K K D V E S S L S S C R N S S S T V S C L 1152
ABCR I I A Q G R L Y C S G T P L F L K N C F G T G L Y L T L V R K . M K N I Q S Q R K G S E G T C S C S 1180
Abc2 I I S H G K L K C C G S P L F L K G A Y K D G Y R L T L V K Q P A E P G T S Q E P G L A S S P S G C 279
ABCC I M A K G E L Q C C G S S L F L K Q K Y G A G Y H M T L V K E P . . . . . . . . . . . . . . . . 766
```

*FIG. 4B*

```
Abc1 KKEDSVSQSSSDAGLGSDHESDTLTIDVSAISNLIRKHVSEARLVEDIGH 1202
ABCR SKGFSTTCPAHVDDLTPE...QVLDGDVNELMDVVLHHVPEAKLVECIGQ 1227
Abc2 PRLSSCSEP...................QVSQFIRKHVASSLLVSDTST  309
ABCC ......................HCNPEDISQLVHHHVPNATLESSAGA  792

Abc1 ELTYVLPYEAAKEGAFVELFHEIDDRLSDLGISSYGISETTLEEIFLKVA 1252
ABCR ELIFLLPNKNFKHRAYASLFRELEETLADLGLSSFGISDTPLEEIFLKVT 1277
Abc2 ELSYILPSEAVKKGAFERLFQQLEHSLDALHLSSFGLMDTTLEEVFLKVS  359
ABCC ELSFILPRESTHR..FEGLFAKLEKKQKELGIASFGASITTMEEVFLRVG  840

Abc1 EE...................SGVDAETSDGTLPARRNR.RAFGDKQ.SC 1281
ABCR ED..................SDSGPLFAGG..AQQKR.ENVNPRH.PC 1303
Abc2 EEDQSLENSEADVKESRKDVLPQAEGLTAVGGQAGNLARCSELAQSQ.AS  408
ABCC KLVDSSMDI..............QAIQLPALQYQHERRASDWAVDSNLCGA  877

Abc1 LHPFTEDDAVDPNDSDI....DPESRETDLLSGMD.............. 1312
ABCR LGP.REKAGQTPQDSNVCSPGAPAAHPEGQPPPEPE.............. 1238
Abc2 LQSASSVGSARGEEGTGYSDGYGDYRPLFDNLQDPDNVSLQEAEMEALAQ  458
ABCC MDPSDGIGALIEEERT..................................  893

Abc1 .GKGSYQLKGWKLTQQQFVALLWKRLLIARRSRKGFFAQIVLPAVFVCIA 1361
ABCR .CPGPQLNTGTQLVLQHVQALLVKRFQHTIRSHKDFLAQIVLPATFVFLA 1387
Abc2 VGQGSRKLEGWWLKMRQFHGLLVKRFHCARRNSKALCSQILLPAFFVCVA  508
ABCC ...AVKLNTGLALHCQQFWAMFLKKAAYSWREWKMVAAQVLVPLTCVTLA  940
                                               H1

Abc1 LVFSLIVPPFGKYPSLELQPWMYN..................EQYTF.VSN 1393
ABCR LMLSIVILPFGEYPALTLHPWIYG..................QQYTF.FSM 1419
Abc2 MTVALSVPEIGDLPPLVLSPSQYHNYTQPRGNFIPYANEERQEYRLRLSP  558
ABCC LLAINYSSELFDDPMLRLTLGEYGRTVVP.....................  940

Abc1 DA..................PEDMGTQELLNA......LTKDPGF 1414
ABCR DE..................PGSEQFTVLADV......LLNKPGF 1440
Abc2 DASPQQLVSTFRLPSGVGATCVLKSPANGSLGPMLNLSSGESRLLAARFF  608
ABCC ....................FSVPGTSQLGQQL.................  982

Abc1 GTRCME....GNPIPDTPCLAGEEDWTISPVPQSIVDLFQNGNWTMKNPS 1460
ABCR GNRCLK....EGWLPEYPCGNSTPWKTPS.VSPNITQLFQKQKWTQVNPS 1485
Abc2 DSMCLESFTQGLPLSNFVPPPPSPAPSDSPVXPDEDSLQAWNMSLPPTAG  658
ABCC ..................................................  982

Abc1 PACQCSSDKIKKMLPV..................CPPGAGGLPPPQRKQKTADI 1496
ABCR PSCRCSTREKLTMLPE.................CPEGAGGLPPPQRTQRSTEI 1521
Abc2 PETWTSAPSLPRLVHEPVRCTCSAQGTGFSCPSSVGG.HPPQMRVVTGDI  707
ABCC ......SEHLKDALQ..................AEGQEPR.......EV 1000

Abc1 LQNLTGRNISDYLVKTYVQIIAKSLKNKIWVNEFRYGGFSLGVSNSQALP 1546
ABCR LQDLTDRNISDFLVKTYPALIRSSLKSKFWVNEQRYGGISIGGKLPVVPI 1571
Abc2 LTDITGHNVSEYLLFT.........SDRFRLH..RYGAITFGN.......  739
ABCC LGDL.....EEFLIF..........RASVEGGGFNERCL........... 1024

Abc1 PSHEVNDAIKQMKKLLKLTKDTSADRFLSSLGRFMAGLDTKNNVKVWFNN 1596
ABCR TGEALVGFLSDLGRIMNVSGGPITREASKEIPDFLKHLETEDNIKVWFNN 1621
Abc2 ..................VQKSIPASFGARVPPMVRKIAVRRVAQVLYNN  771
ABCC ...................VAASFRDVGERTVVNALFNN 1044

Abc1 KGWHAISSFLNVINNAILRANLQKGE.NPSQYGITAFNHPLNLTKQQLSE 1645
ABCR KGWHALVSFLNVAHNAILRASLPKDR.SPEEYGITVISQPLNLTKEQLSE 1670
Abc2 KGYHSMPTYLNSLNNAILRANLPKSKGNPAAYXITVTNHPMNKTSASLS.  820
ABCC QAYHSPATALAVVDNLLFKL.....LCGPHASIVVSNFPQPRSALQAAK 1088

Abc1 VALMTTSVDVLVSICVIFAMSFVPASFVVFLIQERVSKAKHLQFISGVKP 1695
ABCR ITVLTTSVDAVVAICVIFSMSFVPASFVLYLIQERVNKSKHLQFISGVSP 1720
Abc2 LDYLLQGTDVVIAIFIIVAMSFVPASFVVFLVAEKSTKAKHLQFVSGCNP  870
ABCC DQFNEGRKGFDIALNLLFAMAFLASTFSILAVSERAVQAKHVQFVSGVHV 1138
```

FIG. 4C

```
Abc1 VIYWLSNFVWDNCNYVVPATLVIIIFICFQQKSYVSSINLPVLALLLLY 1745
ABCR TIYWVTNFLWDIMNYSVSAGLVVGIFIGFQKKAYTSPENLPALVALLLLY 1770
Abc2 VIYWLANYVWDNLNYLVPATCCVIILFVFDLPAYTSPINFPAVLSLFLLY 920
ABCC ASFWLSALLWDLISFLIPSLLLLVVFKAFDVRAFTHDGHMADTLLLLLY 1188

Abc1 GWSIIPLMYPASFVFKIPSTAYVVLTSVNLFIGINGSVATFVLELFTNNK 1795
ABCR GWAVIPMMYPASFLFDVPSTAYVALSCANLFIGINSSAITFILELFDNNR 1820
Abc2 GWSIIPIMYPASFWFEVPSSAYVFLIVINLFIGITATVATFLLQLFEHDK 970
ABCC GWAIIPLMYLMNFFFLGAATAYTRLTIFNILSGIATFLMVIMRI..PAV 1236

Abc1 .LNDINDILKSVFLIFPHFCLGRGLIDM..........VKNQAMADALER 1834
ABCR TLLRFNAVLRKLLTVFPHFCLGRGLIDL..........ALSQAVTDVYAR 1860
Abc2 DLKVVNSYLKSCFLIFPNYNLGHGLMEM..........AYNEYINEYYAK 1010
ABCC KLEELSKTLDHVFLVLPNHCLGMAVSSFYENYETRRYCTSSEVAAHYCKK 1286

Abc1 FG.E.NRFVSPLSWDLVGRNLFAMAVEGVVFELITVLIQYRFFIRPRPVK 1882
ABCR FG.E.EHSANPFHWDLIGKNLFAMVVEGVVYFLLTILVQRHFFLSQWIAE 1898
Abc2 IG.QFDKMKSPFEWDIVIRGLVAMTVEGFVGFFLTIMCQYNFLRQPQRLP 1059
ABCC YNIQYQENFYAWSAPGVGRFVASMAASGCAYLILLFLIETNLLQRLRGIL 1336

Abc1 AKLP...........PLNDEDEDVRRERQRILDGGGQNDI...LEIKEL 1917
ABCR PTKE...........PIVDEDDDVAEERQRIITGGNKTDI...LRLHEL 1943
Abc2 VSTK...........PV.EDDVDVASERQRVLRGDADNDM...VKIENL 1093
ABCC CALRRRTLTELYTHMPVLPEDQDVADERMRILAPSPDSLLHTPLIWKEL 1386

Abc1 TKIYRRKRKP...AVDRICIGI.PPGECFGLLGVNGAGKSTTFKMLTGDT 1963
ABCR TKIYLGTSSP...AVDRLCVGV.RPGECFGLLGVNGAGKTTTFKMLTGDT 1989
Abc2 TKVYKSRKIGRILAVDRLCLGVCVPGECFGLLGVNGAGKTSTFKMLTGDE 1143
ABCC SKVYEQR..VPLLAVDRLSLAV.QKGECFGLLGFNGAGKTTTFKMLTGEE 1433
                                            A

Abc1 PVTRGDAFLNKNSILSNIHEVHQNMGYCPQFDAITELLTGREHVEFFALL 2013
ABCR TVTSGDAIVAGKSILTNISEVHQNMGYCPQFDAIDELLTGREHLYLYARL 2039
Abc2 STTGGEAFVNGHSVLKDLLQVQQSLGYCPQFDVPVDELTAREHLQLYTRL 1193
ABCC SLTSGDAFVGGHRISSDVGKVRQRIGYCPQFDALLDHMTGREMLVMYARL 1483

Abc1 RGVPEKEVGKFGEWAIRKLGLVKYGEKYASNYSGGNKRKLSTAMALIGGP 2063
ABCR RGVPAEEIEKVANWSIKSLGLTVYADCLAGTYSGGNKRKLSTATALIGCP 2080
Abc2 RCIPWKDEAQVVKWALEKLELTKYADKPAGTYSGGNKRKLSTAIALIGYP 1243
ABCC RGIPERHIGACVENTLRGLLLEPHANKLVRTYSGGNKRKLSTGIALIGEP 1533
                                  C

Abc1 PVVFLDEPTTGMDPKARRFLWNCALSIVKEGRSVVLTSHSMEECEALCTR 2113
ABCR PLVLLDEPTTGMDPQARRMLWNVIVSIIRKGRAVVLTSHSMEECEALCTR 2139
Abc2 AFIFLDEPTTGMDPKARRFLWNLILDLIKTGRSVVLTSHSMEECEALCTR 1293
ABCC AVIFLDEPSTGMDPVARRLLWDTVARARESGKAIIITSHSMEECEALCTR 1583
         B

Abc1 MAIMVNGRFRCLGSVQHLKNRFGDGYTIVVRIAGSN.....PDLKPVQEFF 2159
ABCR LAIMVKGAFRCMGTIQHLKSKFGDGYIVTMKIKSPKDDLLPDLNPVEQFF 2189
Abc2 LAIMVNGRLHCLGSIQHLKNRFGDGYMITVRTKSSQ....NVKDVVRFF 1338
ABCC LAIMVQGQFKCLGSPQHLKSKFGSGYSLRAKVQSEGQQ..EALEEFKAFV 1631

Abc1 GLAFPGSVLKEKHRNMLQYQLPSSLSSLARIFSILSQSKKRLHIEDYSVS 2209
ABCR QGNFPGSVQRERHYNMLQFQVSS..SSLARIFQLLLSHKDSLLIEEYSVT 2237
Abc2 NRNFPEAHAQGKIPYKVQYQLKSEHISLAQVFSKMEQVVGVLGIEDYSVS 1388
ABCC DLTFPGSVLEDEHQGMVHYHLPGRDLSWAKVFGILEKAKEKYGVDDYSVS 1631

Abc1 QTTLDQVFVNFAKDQSDDDHLKDLS..............LHKNQTVVDVAV 2246
ABCR QTTLDQVFVNFAKQQTESH..DLP...............LHPRAAGASRQA 2271
Abc2 QTTLDNVFVNFAKKQSDNVEQQEAEPSSLPSPLGLLSLLRPRPAPTELRA 1438
ABCC QISLEQVFLSFAHLQPPTAEEGR............................ 1704

Abc1 LTSFLQDEKVKESYV................... 2261
ABCR QD................................ 2273
Abc2 LVADEPEDLDTEDEGLISFEEERAQLSFNTDTLC 1472
ABCC .................................. 1704
```

FIG. 4D

MAPPING THE MOUSE *ABCR* LOCUS

SEQUENCE LISTING

<160> NUMBER OF SEQ ID NOS: 120

<210> SEQ ID NO 1
<211> LENGTH: 7783
<212> TYPE: DNA
<213> ORGANISM: Homo sapiens

<400> SEQUENCE: 1

```
cccctacccc tctgctaagc tcagggataa cccaactagc tgaccataat gacttcagtc      60

attacggagc aagatgaaag actaaaagag ggagggatca cttcagatct gccgagtgag     120

tcgattggac ttaaagggcc agtcaaaccc tgactgccgg ctcatggcag gctcttgccg     180

aggacaaatg cccagcctat atttatgcaa agagattttg ttccaaactt aaggtcaaag     240
```

```
atacctaaag acatccccct caggaacccc tctcatggag gagagtgcct gagggtcttg    300
gtttcccatt gcatccccca cctcaatttc cctggtgccc agccacttgt gtctttaggg    360
ttctctttct ctccataaaa gggagccaac acagtgtcgg cctcctctcc ccaactaagg    420
gcttatgtgt aattaaaagg gattatgctt tgaaggggaa aagtagcctt taatcaccag    480
gagaaggaca cagcgtccgg agccagaggc gctcttaacg gcgtttatgt cctttgctgt    540
ctgaggggcc tcagctctga ccaatctggt cttcgtgtgg tcattagcat gggcttcgtg    600
agacagatac agcttttgct ctggaagaac tggaccctgc ggaaaaggca aaagattcgc    660
tttgtggtgg aactcgtgtg gcctttatct ttatttctgg tcttgatctg gttaaggaat    720
gccaacccgc tctacagcca tcatgaatgc catttcccca acaaggcgat gccctcagca    780
ggaatgctgc cgtggctcca ggggatcttc tgcaatgtga acaatccctg ttttcaaagc    840
cccaccccag gagaatctcc tggaattgtg tcaaactata acaactccat cttggcaagg    900
gtatatcgag attttcaaga actcctcatg aatgcaccag agagccagca ccttggccgt    960
atttggacag agctacacat cttgtcccaa ttcatggaca ccctccggac tcacccggag   1020
agaattgcag gaagaggaat acgaataagg gatatcttga aagatgaaga aacactgaca   1080
ctatttctca ttaaaaacat cggcctgtct gactcagtgg tctaccttct gatcaactct   1140
caagtccgtc cagagcagtt cgctcatgga gtcccggacc tggcgctgaa ggacatcgcc   1200
tgcagcgagg ccctcctgga gcgcttcatc atcttcagcc agagacgcgg ggcaaagacg   1260
gtgcgctatg ccctgtgctc cctctcccag ggcaccctac agtggataga agacactctg   1320
tatgccaacg tggacttctt caagctcttc cgtgtgcttc ccacactcct agacagccgt   1380
tctcaaggta tcaatctgag atcttgggga ggaatattat ctgatatgtc accaagaatt   1440
caagagttta tccatcggcc gagtatgcag gacttgctgt gggtgaccag gcccctcatg   1500
cagaatggtg gtccagagac ctttacaaag ctgatgggca tcctgtctga cctcctgtgt   1560
ggctaccccg agggaggtgg ctctcgggtg ctctccttca actggtatga agacaataac   1620
tataaggcct ttctggggat tgactccaca aggaaggatc ctatctattc ttatgacaga   1680
agaacaacat ccttttgtaa tgcattgatc cagagcctgg agtcaaatcc tttaaccaaa   1740
atcgcttgga gggcggcaaa gcctttgctg atgggaaaaa tcctgtacac tcctgattca   1800
cctgcagcac gaaggatact gaagaatgcc aactcaactt ttgaagaact ggaacacgtt   1860
aggaagttgg tcaaagcctg ggaagaagta gggccccaga tctggtactt ctttgacaac   1920
agcacacaga tgaacatgat cagagatacc ctggggaacc caacagtaaa agactttttg   1980
aataggcagc ttggtgaaga aggtattact gctgaagcca tcctaaactt cctctacaag   2040
ggccctcggg aaagccaggc tgacgacatg gccaacttcg actggaggga catatttaac   2100
atcactgatc gcaccctccg cctggtcaat caatacctgg agtgcttggt cctggataag   2160
tttgaaagct acaatgatga aactcagctc acccaacgtg ccctctctct actggaggaa   2220
aacatgttct gggccggagt ggtattccct gacatgtatc cctggaccag ctctctacca   2280
ccccacgtga agtataagat ccgaatggac atagacgtgg tggagaaaac caataagatt   2340
aaagacaggt attgggattc tggtcccaga gctgatcccg tggaagattt ccggtacatc   2400
tggggcgggt ttgcctatct gcaggacatg gttgaacagg ggatcacaag gagccaggtg   2460
caggcggagg ctccagttgg aatctacctc cagcagatgc cctacccctg cttcgtggac   2520
gattctttca tgatcatcct gaaccgctgt ttccctatct tcatggtgct ggcatggatc   2580
tactctgtct ccatgactgt gaagagcatc gtcttggaga aggagttgcg actgaaggag   2640
```

```
accttgaaaa atcagggtgt ctccaatgca gtgatttggt gtacctggtt cctggacagc   2700

ttctccatca tgtcgatgag catcttcctc ctgacgatat tcatcatgca tggaagaatc   2760

ctacattaca gcgacccatt catcctcttc ctgttcttgt tggctttctc cactgccacc   2820

atcatgctgt gctttctgct cagcaccttc ttctccaagg ccagtctggc agcagcctgt   2880

agtggtgtca tctatttcac cctctacctg ccacacatcc tgtgcttcgc ctggcaggac   2940

cgcatgaccg ctgagctgaa gaaggctgtg agcttactgt ctccggtggc atttggattt   3000

ggcactgagt acctggttcg ctttgaagag caaggcctgg ggctgcagtg gagcaacatc   3060

gggaacagtc ccacggaagg ggacgaattc agcttcctgc tgtccatgca gatgatgctc   3120

cttgatgctg cgtgctatgg cttactcgct tggtaccttg atcaggtgtt tccaggagac   3180

tatggaaccc cacttccttg gtactttctt ctacaagagt cgtattggct tagcggtgaa   3240

gggtgttcaa ccagagaaga aagagccctg gaaaagaccg agcccctaac agaggaaacg   3300

gaggatccag agcacccaga aggaatacac gactccttct ttgaacgtga gcatccaggg   3360

tgggttcctg gggtatgcgt gaagaatctg gtaaagattt ttgagccctg tggccggcca   3420

gctgtggacc gtctgaacat caccttctac gagaaccaga tcaccgcatt cctgggccac   3480

aatggagctg ggaaaaccac caccttgtcc atcctgacgg gtctgttgcc accaacctct   3540

gggactgtgc tcgttggggg aagggacatt gaaaccagcc tggatgcagt ccggcagagc   3600

cttggcatgt gtccacagca caacatcctg ttccaccacc tcacggtggc tgagcacatg   3660

ctgttctatg cccagctgaa aggaaagtcc caggaggagg cccagctgga gatggaagcc   3720

atgttggagg acacaggcct ccaccacaag cggaatgaag aggctcagga cctatcaggt   3780

ggcatgcaga gaaagctgtc ggttgccatt gcctttgtgg gagatgccaa ggtggtgatt   3840

ctggacgaac ccacctctgg ggtggaccct tactcgagac gctcaatctg ggatctgctc   3900

ctgaagtatc gctcaggcag aaccatcatc atgcccactc accacatgga cgaggccgac   3960

caccaagggg accgcattgc catcattgcc cagggaaggc tctactgctc aggcacccca   4020

ctcttcctga agaactgctt tggcacaggc ttgtacttaa ccttggtgcg caagatgaaa   4080

aacatccaga gccaaaggaa aggcagtgag gggacctgca gctgctcgtc taagggtttc   4140

tccaccacgt gtccagccca cgtcgatgac ctaactccag aacaagtcct ggatggggat   4200

gtaaatgagc tgatggatgt agttctccac catgttccag aggcaaagct ggtggagtgc   4260

attggtcaag aacttatctt ccttcttcca aataagaact tcaagcacag agcatatgcc   4320

agccttttca gagagctgga ggagacgctg gctgaccttg gtctcagcag ttttggaatt   4380

tctgacactc ccctggaaga gatttttctg aaggtcacgg aggattctga ttcaggacct   4440

ctgtttgcgg gtggcgctca gcagaaaaga gaaaacgtca acccccgaca cccctgcttg   4500

ggtcccagag agaaggctgg acagacaccc caggactcca atgtctgctc cccaggggcg   4560

ccggctgctc acccagaggg ccagcctccc ccagagccag agtgcccagg cccgcagctc   4620

aacacgggga cacagctggt cctccagcat gtgcaggcgc tgctggtcaa gagattccaa   4680

cacaccatcc gcagccacaa ggacttcctg gcgcagatcg tgctcccggc taccttttgtg   4740

tttttggctc tgatgctttc tattgttatc cttccttttg gcgaataccc cgctttgacc   4800

cttcacccct ggatatatgg gcagcagtac accttcttca gcatggatga accaggcagt   4860

gagcagttca cggtacttgc agacgtcctc ctgaataagc caggctttgg caaccgctgc   4920

ctgaaggaag ggtggcttcc ggagtacccc tgtggcaact caacaccctg gaagactcct   4980

tctgtgtccc caaacatcac ccagctgttc cagaagcaga aatggacaca ggtcaaccct   5040
```

```
tcaccatcct gcaggtgcag caccagggag aagctcacca tgctgccaga gtgccccgag   5100
ggtgccgggg gcctcccgcc cccccagaga acacagcgca gcacggaaat tctacaagac   5160
ctgacggaca ggaacatctc cgacttcttg gtaaaaacgt atcctgctct tataagaagc   5220
agcttaaaga gcaaattctg ggtcaatgaa cagaggtatg gaggaatttc cattggagga   5280
aagctcccag tcgtccccat cacgggggaa gcacttgttg ggtttttaag cgaccttggc   5340
cggatcatga atgtgagcgg gggccctatc actagagagg cctctaaaga aatacctgat   5400
ttccttaaac atctagaaac tgaagacaac attaaggtgt ggtttaataa caaaggctgg   5460
catgccctgg tcagctttct caatgtggcc cacaacgcca tcttacgggc cagcctgcct   5520
aaggacagga gccccgagga gtatggaatc accgtcatta gccaacccct gaacctgacc   5580
aaggagcagc tctcagagat tacagtgctg accacttcag tggatgctgt ggttgccatc   5640
tgcgtgattt tctccatgtc cttcgtccca gccagctttg tcctttattt gatccaggag   5700
cgggtgaaca aatccaagca cctccagttt atcagtggag tgagccccac cacctactgg   5760
gtgaccaact tcctctggga catcatgaat tattccgtga gtgctgggct ggtggtgggc   5820
atcttcatcg ggtttcagaa gaaagcctac acttctccag aaaaccttcc tgcccttgtg   5880
gcactgctcc tgctgtatgg atgggcggtc attcccatga tgtacccagc atccttcctg   5940
tttgatgtcc ccagcacagc ctatgtggct ttatcttgtg ctaatctgtt catcggcatc   6000
aacagcagtg ctattacctt catcttggaa ttatttgata ataaccggac gctgctcagg   6060
ttcaacgccg tgctgaggaa gctgctcatt gtcttccccc acttctgcct gggccggggc   6120
ctcattgacc ttgcactgag ccaggctgtg acagatgtct atgcccggtt tggtgaggag   6180
cactctgcaa atccgttcca ctgggacctg attgggaaga acctgtttgc catggtggtg   6240
gaaggggtgg tgtacttcct cctgaccctg ctggtccagc gccacttctt cctctcccaa   6300
tggattgccg agcccactaa ggagcccatt gttgatgaag atgatgatgt ggctgaagaa   6360
agacaaagaa ttattactgg tggaaataaa actgacatct taaggctaca tgaactaacc   6420
aagatttatc tgggcacctc cagcccagca gtggacaggc tgtgtgtcgg agttcgccct   6480
ggagagtgct ttggcctcct gggagtgaat ggtgccggca aaacaaccac attcaagatg   6540
ctcactgggg acaccacagt gacctcaggg gatgccaccg tagcaggcaa gagtatttta   6600
accaatattt ctgaagtcca tcaaaatatg ggctactgtc ctcagtttga tgcaatcgat   6660
gagctgctca caggacgaga acatctttac ctttatgccc ggcttcgagg tgtaccagca   6720
gaagaaatcg aaaaggttgc aaactggagt attaagagcc tgggcctgac tgtctacgcc   6780
gactgcctgg ctggcacgta cagtgggggc aacaagcgga aactctccac agccatcgca   6840
ctcattggct gcccaccgct ggtgctgctg gatgagccca ccacagggat ggacccccag   6900
gcacgccgca tgctgtggaa cgtcatcgtg agcatcatca gaaaagggag ggctgtggtc   6960
ctcacatccc acagcatgga agaatgtgag gcactgtgta cccggctggc catcatggta   7020
aagggcgcct ttcgatgtat gggcaccatt cagcatctca agtccaaatt tggagatggc   7080
tatatcgtca caatgaagat caaatccccg aaggacgacc tgcttcctga cctgaaccct   7140
gtggagcagt tcttccaggg gaacttccca ggcagtgtgc agagggagag gcactacaac   7200
atgctccagt tccaggtctc ctcctcctcc ctggcgagga tcttccagct cctcctctcc   7260
cacaaggaca gcctgctcat cgaggagtac tcagtcacac agaccacact ggaccaggtg   7320
tttgtaaatt ttgctaaaca gcagactgaa agtcatgacc tccctctgca ccctcgagct   7380
gctggagcca gtcgacaagc ccaggactga tctttcacac cgctcgttcc tgcagccaga   7440
```

```
aaggaactct gggcagctgg aggcgcagga gcctgtgccc atatggtcat ccaaatggac   7500
tggcccagcg taaatgaccc cactgcagca gaaaacaaac acacgaggag catgcagcga   7560
attcagaaag aggtctttca gaaggaaacc gaaactgact tgctcacctg gaacacctga   7620
tggtgaaacc aaacaaatac aaaatccttc tccagacccc agaactagaa accccgggcc   7680
atcccactag cagctttggc ctccatattg ctctcatttc aagcagatct gcttttctgc   7740
atgtttgtct gtgtgtctgc gttgtgtgtg attttcatgg aaa                      7783
```

<210> SEQ ID NO 2
<211> LENGTH: 6819
<212> TYPE: DNA
<213> ORGANISM: Homo sapiens

<400> SEQUENCE: 2

```
atgggcttcg tgagacagat acagcttttg ctctggaaga actggaccct gcggaaaagg     60
caaaagattc gctttgtggt ggaactcgtg tggcctttat ctttatttct ggtcttgatc    120
tggttaagga atgccaaccc gctctacagc catcatgaat gccatttccc caacaaggcg    180
atgccctcag caggaatgct gccgtggctc caggggatct tctgcaatgt gaacaatccc    240
tgttttcaaa gccccacccc aggagaatct cctggaattg tgtcaaacta taacaactcc    300
atcttggcaa gggtatatcg agattttcaa gaactcctca tgaatgcacc agagagccag    360
caccttggcc gtatttggac agagctacac atcttgtccc aattcatgga caccctccgg    420
actcacccgg agagaattgc aggaagagga atacgaataa gggatatctt gaaagatgaa    480
gaaacactga cactatttct cattaaaaac atcggcctgt ctgactcagt ggtctacctt    540
ctgatcaact ctcaagtccg tccagagcag ttcgctcatg gagtcccgga cctggcgctg    600
aaggacatcg cctgcagcga ggccctcctg gagcgcttca tcatcttcag ccagagacgc    660
ggggcaaaga cggtgcgcta tgccctgtgc tccctctccc agggcaccct acagtggata    720
gaagacactc tgtatgccaa cgtggacttc ttcaagctct tccgtgtgct tcccacactc    780
ctagacagcc gttctcaagg tatcaatctg agatcttggg gaggaatatt atctgatatg    840
tcaccaagaa ttcaagagtt tatccatcgg ccgagtatgc aggacttgct gtgggtgacc    900
aggcccctca tgcagaatgg tggtccagag acctttacaa agctgatggg catcctgtct    960
gacctcctgt gtggctaccc cgagggaggt ggctctcggg tgctctcctt caactggtat   1020
gaagacaata actataaggc ctttctgggg attgactcca caaggaagga tcctatctat   1080
tcttatgaca gaagaacaac atccttttgt aatgcattga tccagagcct ggagtcaaat   1140
cctttaacca aaatcgcttg gagggcggca aagcctttgc tgatgggaaa aatcctgtac   1200
actcctgatt cacctgcagc acgaaggata ctgaagaatg ccaactcaac ttttgaagaa   1260
ctggaacacg ttaggaagtt ggtcaaagcc tgggaagaag tagggcccca gatctggtac   1320
ttctttgaca acagcacaca gatgaacatg atcagagata ccctggggaa cccaacagta   1380
aaagactttt tgaataggca gcttggtgaa gaaggtatta ctgctgaagc catcctaaac   1440
ttcctctaca agggccctcg ggaaagccag gctgacgaca tggccaactt cgactggagg   1500
gacatattta acatcactga tcgcaccctc cgcctggtca atcaatacct ggagtgcttg   1560
gtcctggata agtttgaaag ctacaatgat gaaactcagc tcacccaacg tgccctctct   1620
ctactggagg aaaacatgtt ctgggccgga gtggtattcc ctgacatgta tccctggacc   1680
agctctctac caccccacgt gaagtataag atccgaatgg acatagacgt ggtggagaaa   1740
accaataaga ttaaagacag gtattgggat tctggtccca gagctgatcc cgtggaagat   1800
```

-continued

```
ttccggtaca tctggggcgg gtttgcctat ctgcaggaca tggttgaaca ggggatcaca   1860
aggagccagg tgcaggcgga ggctccagtt ggaatctacc tccagcagat gccctacccc   1920
tgcttcgtgg acgattcttt catgatcatc ctgaaccgct gtttccctat cttcatggtg   1980
ctggcatgga tctactctgt ctccatgact gtgaagagca tcgtcttgga gaaggagttg   2040
cgactgaagg agaccttgaa aaatcagggt gtctccaatg cagtgatttg gtgtacctgg   2100
ttcctggaca gcttctccat catgtcgatg agcatcttcc tcctgacgat attcatcatg   2160
catggaagaa tcctacatta cagcgaccca ttcatcctct tcctgttctt gttggctttc   2220
tccactgcca ccatcatgct gtgctttctg ctcagcacct tcttctccaa ggccagtctg   2280
gcagcagcct gtagtggtgt catctatttc accctctacc tgccacacat cctgtgcttc   2340
gcctggcagg accgcatgac cgctgagctg aagaaggctg tgagcttact gtctccggtg   2400
gcatttggat ttggcactga gtacctggtt cgctttgaag agcaaggcct ggggctgcag   2460
tggagcaaca tcgggaacag tcccacggaa ggggacgaat tcagcttcct gctgtccatg   2520
cagatgatgc tccttgatgc tgcgtgctat ggcttactcg cttggtacct tgatcaggtg   2580
tttccaggag actatggaac ccccacttcct tggtactttc ttctacaaga gtcgtattgg   2640
cttagcggtg aagggtgttc aaccagagaa gaaagagccc tggaaaagac cgagccccta   2700
acagaggaaa cggaggatcc agagcaccca gaaggaatac acgactcctt ctttgaacgt   2760
gagcatccag ggtgggttcc tggggtatgc gtgaagaatc tggtaaagat tttgagccc    2820
tgtggccggc cagctgtgga ccgtctgaac atcaccttct acgagaacca gatcaccgca   2880
ttcctgggcc acaatggagc tgggaaaacc accaccttgt ccatcctgac gggtctgttg   2940
ccaccaacct ctgggactgt gctcgttggg ggaagggaca ttgaaaccag cctggatgca   3000
gtccggcaga gccttggcat gtgtccacag cacaacatcc tgttccacca cctcacggtg   3060
gctgagcaca tgctgttcta tgcccagctg aaaggaaagt cccaggagga ggcccagctg   3120
gagatggaag ccatgttgga ggacacaggc ctccaccaca agcggaatga agaggctcag   3180
gacctatcag gtggcatgca gagaaagctg tcggttgcca ttgcctttgt gggagatgcc   3240
aaggtggtga ttctggacga acccacctct ggggtggacc cttactcgag acgctcaatc   3300
tgggatctgc tcctgaagta tcgctcaggc agaaccatca tcatgcccac tcaccacatg   3360
gacgaggccg accaccaagg ggaccgcatt gccatcattg cccagggaag gctctactgc   3420
tcaggcaccc cactcttcct gaagaactgc tttggcacag gcttgtactt aaccttggtg   3480
cgcaagatga aaaacatcca gagccaaagg aaaggcagtg aggggacctg cagctgctcg   3540
tctaagggtt tctccaccac gtgtccagcc cacgtcgatg acctaactcc agaacaagtc   3600
ctggatgggg atgtaaatga gctgatggat gtagttctcc accatgttcc agaggcaaag   3660
ctggtggagt gcattggtca agaacttatc ttccttcttc caaataagaa cttcaagcac   3720
agagcatatg ccagcctttt cagagagctg gaggagacgc tggctgacct tggtctcagc   3780
agttttggaa tttctgacac tcccctggaa gagatttttc tgaaggtcac ggaggattct   3840
gattcaggac ctctgtttgc gggtggcgct cagcagaaaa gagaaaacgt caaccccccga   3900
cacccctgct tgggtcccag agagaaggct ggacagacac cccaggactc caatgtctgc   3960
tccccagggg cgccggctgc tcacccagag ggccagcctc cccagagcc  agagtgccca   4020
ggcccgcagc tcaacacggg gacacagctg gtcctccagc atgtgcaggc gctgctggtc   4080
aagagattcc aacacaccat ccgcagccac aaggacttcc tggcgcagat cgtgctcccg   4140
gctacctttg tgtttttggc tctgatgctt tctattgtta tccttccttt tggcgaatac   4200
```

```
cccgctttga cccttcaccc ctggatatat gggcagcagt acaccttctt cagcatggat   4260
gaaccaggca gtgagcagtt cacggtactt gcagacgtcc tcctgaataa gccaggcttt   4320
ggcaaccgct gcctgaagga agggtggctt ccggagtacc cctgtggcaa ctcaacaccc   4380
tggaagactc cttctgtgtc cccaaacatc acccagctgt tccagaagca gaaatggaca   4440
caggtcaacc cttcaccatc ctgcaggtgc agcaccaggg agaagctcac catgctgcca   4500
gagtgccccg agggtgccgg gggcctcccg ccccccccaga gaacacagcg cagcacggaa   4560
attctacaag acctgacgga caggaacatc tccgacttct tggtaaaaac gtatcctgct   4620
cttataagaa gcagcttaaa gagcaaattc tgggtcaatg aacagaggta tggaggaatt   4680
tccattggag gaaagctccc agtcgtcccc atcacggggg aagcacttgt tgggttttta   4740
agcgaccttg gccggatcat gaatgtgagc gggggcccta tcactagaga ggcctctaaa   4800
gaaatacctg atttccttaa acatctagaa actgaagaca acattaaggt gtggtttaat   4860
aacaaaggct ggcatgccct ggtcagcttt ctcaatgtgg cccacaacgc catcttacgg   4920
gccagcctgc ctaaggacag gagccccgag gagtatggaa tcaccgtcat tagccaaccc   4980
ctgaacctga ccaaggagca gctctcagag attacagtgc tgaccacttc agtggatgct   5040
gtggttgcca tctgcgtgat ttctccatg tccttcgtcc cagccagctt tgtcctttat   5100
ttgatccagg agcgggtgaa caaatccaag cacctccagt ttatcagtgg agtgagcccc   5160
accacctact gggtgaccaa cttcctctgg gacatcatga attattccgt gagtgctggg   5220
ctggtggtgg gcatcttcat cgggtttcag aagaaagcct acacttctcc agaaaacctt   5280
cctgcccttg tggcactgct cctgctgtat ggatgggcgg tcattcccat gatgtaccca   5340
gcatccttcc tgtttgatgt ccccagcaca gcctatgtgg ctttatcttg tgctaatctg   5400
ttcatcggca tcaacagcag tgctattacc ttcatcttgg aattatttga taataaccgg   5460
acgctgctca ggttcaacgc cgtgctgagg aagctgctca ttgtcttccc ccacttctgc   5520
ctgggccggg gcctcattga ccttgcactg agccaggctg tgacagatgt ctatgcccgg   5580
tttggtgagg agcactctgc aaatccgttc cactgggacc tgattgggaa gaacctgttt   5640
gccatggtgg tggaaggggt ggtgtacttc ctcctgaccc tgctggtcca gcgccacttc   5700
ttcctctccc aatggattgc cgagcccact aaggagccca ttgttgatga agatgatgat   5760
gtggctgaag aaagacaaag aattattact ggtggaaata aaactgacat cttaaggcta   5820
catgaactaa ccaagattta tctgggcacc tccagcccag cagtggacag gctgtgtgtc   5880
ggagttcgcc ctggagagtg ctttggcctc ctgggagtga atggtgccgg caaaacaacc   5940
acattcaaga tgctcactgg ggacaccaca gtgacctcag gggatgccac cgtagcaggc   6000
aagagtattt taaccaatat ttctgaagtc catcaaaata tgggctactg tcctcagttt   6060
gatgcaatcg atgagctgct cacaggacga gaacatcttt acctttatgc ccggcttcga   6120
ggtgtaccag cagaagaaat cgaaaaggtt gcaaactgga gtattaagag cctgggcctg   6180
actgtctacg ccgactgcct ggctggcacg tacagtgggg gcaacaagcg gaaactctcc   6240
acagccatcg cactcattgg ctgcccaccg ctggtgctgc tggatgagcc caccacaggg   6300
atggaccccc aggcacgccg catgctgtgg aacgtcatcg tgagcatcat cagaaaaggg   6360
agggctgtgg tcctcacatc ccacagcatg gaagaatgtg aggcactgtg tacccggctg   6420
gccatcatgg taaagggcgc ctttcgatgt atgggcacca ttcagcatct caagtccaaa   6480
tttggagatg gctatatcgt cacaatgaag atcaaatccc cgaaggacga cctgcttcct   6540
gacctgaacc ctgtggagca gttcttccag ggaacttcc caggcagtgt gcagagggag   6600
```

```
aggcactaca acatgctcca gttccaggtc tcctcctcct ccctggcgag gatcttccag   6660

ctcctcctct cccacaagga cagcctgctc atcgaggagt actcagtcac acagaccaca   6720

ctggaccagg tgtttgtaaa ttttgctaaa cagcagactg aaagtcatga cctccctctg   6780

caccctcgag ctgctggagc cagtcgacaa gcccaggac                          6819


<210> SEQ ID NO 3
<211> LENGTH: 2273
<212> TYPE: PRT
<213> ORGANISM: Homo sapiens

<400> SEQUENCE: 3

Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
        35                  40                  45

Tyr Ser His His Glu Cys His Phe Pro Asn Lys Ala Met Pro Ser Ala
    50                  55                  60

Gly Met Leu Pro Trp Leu Gln Gly Ile Phe Cys Asn Val Asn Asn Pro
65                  70                  75                  80

Cys Phe Gln Ser Pro Thr Pro Gly Glu Ser Pro Gly Ile Val Ser Asn
                85                  90                  95

Tyr Asn Asn Ser Ile Leu Ala Arg Val Tyr Arg Asp Phe Gln Glu Leu
            100                 105                 110

Leu Met Asn Ala Pro Glu Ser Gln His Leu Gly Arg Ile Trp Thr Glu
        115                 120                 125

Leu His Ile Leu Ser Gln Phe Met Asp Thr Leu Arg Thr His Pro Glu
    130                 135                 140

Arg Ile Ala Gly Arg Gly Ile Arg Ile Arg Asp Ile Leu Lys Asp Glu
145                 150                 155                 160

Glu Thr Leu Thr Leu Phe Leu Ile Lys Asn Ile Gly Leu Ser Asp Ser
                165                 170                 175

Val Val Tyr Leu Leu Ile Asn Ser Gln Val Arg Pro Glu Gln Phe Ala
            180                 185                 190

His Gly Val Pro Asp Leu Ala Leu Lys Asp Ile Ala Cys Ser Glu Ala
        195                 200                 205

Leu Leu Glu Arg Phe Ile Ile Phe Ser Gln Arg Arg Gly Ala Lys Thr
    210                 215                 220

Val Arg Tyr Ala Leu Cys Ser Leu Ser Gln Gly Thr Leu Gln Trp Ile
225                 230                 235                 240

Glu Asp Thr Leu Tyr Ala Asn Val Asp Phe Phe Lys Leu Phe Arg Val
                245                 250                 255

Leu Pro Thr Leu Leu Asp Ser Arg Ser Gln Gly Ile Asn Leu Arg Ser
            260                 265                 270

Trp Gly Gly Ile Leu Ser Asp Met Ser Pro Arg Ile Gln Glu Phe Ile
        275                 280                 285

His Arg Pro Ser Met Gln Asp Leu Leu Trp Val Thr Arg Pro Leu Met
    290                 295                 300

Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Gly Ser Arg Val Leu Ser
                325                 330                 335
```

```
Phe Asn Trp Tyr Glu Asp Asn Asn Tyr Lys Ala Phe Leu Gly Ile Asp
            340                 345                 350

Ser Thr Arg Lys Asp Pro Ile Tyr Ser Tyr Asp Arg Arg Thr Thr Ser
        355                 360                 365

Phe Cys Asn Ala Leu Ile Gln Ser Leu Glu Ser Asn Pro Leu Thr Lys
    370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
                405                 410                 415

Thr Phe Glu Glu Leu Glu His Val Arg Lys Leu Val Lys Ala Trp Glu
            420                 425                 430

Glu Val Gly Pro Gln Ile Trp Tyr Phe Phe Asp Asn Ser Thr Gln Met
        435                 440                 445

Asn Met Ile Arg Asp Thr Leu Gly Asn Pro Thr Val Lys Asp Phe Leu
    450                 455                 460

Asn Arg Gln Leu Gly Glu Glu Gly Ile Thr Ala Glu Ala Ile Leu Asn
465                 470                 475                 480

Phe Leu Tyr Lys Gly Pro Arg Glu Ser Gln Ala Asp Asp Met Ala Asn
                485                 490                 495

Phe Asp Trp Arg Asp Ile Phe Asn Ile Thr Asp Arg Thr Leu Arg Leu
            500                 505                 510

Val Asn Gln Tyr Leu Glu Cys Leu Val Leu Asp Lys Phe Glu Ser Tyr
        515                 520                 525

Asn Asp Glu Thr Gln Leu Thr Gln Arg Ala Leu Ser Leu Leu Glu Glu
    530                 535                 540

Asn Met Phe Trp Ala Gly Val Val Phe Pro Asp Met Tyr Pro Trp Thr
545                 550                 555                 560

Ser Ser Leu Pro Pro His Val Lys Tyr Lys Ile Arg Met Asp Ile Asp
                565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
        595                 600                 605

Ala Tyr Leu Gln Asp Met Val Glu Gln Gly Ile Thr Arg Ser Gln Val
    610                 615                 620

Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
                645                 650                 655

Ile Phe Met Val Leu Ala Trp Ile Tyr Ser Val Ser Met Thr Val Lys
            660                 665                 670

Ser Ile Val Leu Glu Lys Glu Leu Arg Leu Lys Glu Thr Leu Lys Asn
        675                 680                 685

Gln Gly Val Ser Asn Ala Val Ile Trp Cys Thr Trp Phe Leu Asp Ser
    690                 695                 700

Phe Ser Ile Met Ser Met Ser Ile Phe Leu Leu Thr Ile Phe Ile Met
705                 710                 715                 720

His Gly Arg Ile Leu His Tyr Ser Asp Pro Phe Ile Leu Phe Leu Phe
                725                 730                 735

Leu Leu Ala Phe Ser Thr Ala Thr Ile Met Leu Cys Phe Leu Leu Ser
            740                 745                 750

Thr Phe Phe Ser Lys Ala Ser Leu Ala Ala Ala Cys Ser Gly Val Ile
        755                 760                 765
```

```
Tyr Phe Thr Leu Tyr Leu Pro His Ile Leu Cys Phe Ala Trp Gln Asp
    770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
                805                 810                 815

Leu Gly Leu Gln Trp Ser Asn Ile Gly Asn Ser Pro Thr Glu Gly Asp
            820                 825                 830

Glu Phe Ser Phe Leu Leu Ser Met Gln Met Met Leu Leu Asp Ala Ala
        835                 840                 845

Cys Tyr Gly Leu Leu Ala Trp Tyr Leu Asp Gln Val Phe Pro Gly Asp
    850                 855                 860

Tyr Gly Thr Pro Leu Pro Trp Tyr Phe Leu Leu Gln Glu Ser Tyr Trp
865                 870                 875                 880

Leu Ser Gly Glu Gly Cys Ser Thr Arg Glu Glu Arg Ala Leu Glu Lys
                885                 890                 895

Thr Glu Pro Leu Thr Glu Glu Thr Glu Asp Pro Glu His Pro Glu Gly
            900                 905                 910

Ile His Asp Ser Phe Phe Glu Arg Glu His Pro Gly Trp Val Pro Gly
        915                 920                 925

Val Cys Val Lys Asn Leu Val Lys Ile Phe Glu Pro Cys Gly Arg Pro
    930                 935                 940

Ala Val Asp Arg Leu Asn Ile Thr Phe Tyr Glu Asn Gln Ile Thr Ala
945                 950                 955                 960

Phe Leu Gly His Asn Gly Ala Gly Lys Thr Thr Thr Leu Ser Ile Leu
                965                 970                 975

Thr Gly Leu Leu Pro Pro Thr Ser Gly Thr Val Leu Val Gly Gly Arg
            980                 985                 990

Asp Ile Glu Thr Ser Leu Asp Ala  Val Arg Gln Ser Leu  Gly Met Cys
        995                 1000                 1005

Pro Gln  His Asn Ile Leu Phe  His His Leu Thr Val  Ala Glu His
    1010                 1015                 1020

Met Leu  Phe Tyr Ala Gln Leu  Lys Gly Lys Ser Gln  Glu Glu Ala
    1025                 1030                 1035

Gln Leu  Glu Met Glu Ala Met  Leu Glu Asp Thr Gly  Leu His His
    1040                 1045                 1050

Lys Arg  Asn Glu Glu Ala Gln  Asp Leu Ser Gly Gly  Met Gln Arg
    1055                 1060                 1065

Lys Leu  Ser Val Ala Ile Ala  Phe Val Gly Asp Ala  Lys Val Val
    1070                 1075                 1080

Ile Leu  Asp Glu Pro Thr Ser  Gly Val Asp Pro Tyr  Ser Arg Arg
    1085                 1090                 1095

Ser Ile  Trp Asp Leu Leu Leu  Lys Tyr Arg Ser Gly  Arg Thr Ile
    1100                 1105                 1110

Ile Met  Pro Thr His His Met  Asp Glu Ala Asp His  Gln Gly Asp
    1115                 1120                 1125

Arg Ile  Ala Ile Ile Ala Gln  Gly Arg Leu Tyr Cys  Ser Gly Thr
    1130                 1135                 1140

Pro Leu  Phe Leu Lys Asn Cys  Phe Gly Thr Gly Leu  Tyr Leu Thr
    1145                 1150                 1155

Leu Val  Arg Lys Met Lys Asn  Ile Gln Ser Gln Arg  Lys Gly Ser
    1160                 1165                 1170

Glu Gly  Thr Cys Ser Cys Ser  Ser Lys Gly Phe Ser  Thr Thr Cys
```

```
    1175                1180                1185

Pro Ala  His Val Asp Asp Leu  Thr Pro Glu Gln Val  Leu Asp Gly
    1190                1195                1200

Asp Val  Asn Glu Leu Met Asp  Val Val Leu His His  Val Pro Glu
    1205                1210                1215

Ala Lys  Leu Val Glu Cys Ile  Gly Gln Glu Leu Ile  Phe Leu Leu
    1220                1225                1230

Pro Asn  Lys Asn Phe Lys His  Arg Ala Tyr Ala Ser  Leu Phe Arg
    1235                1240                1245

Glu Leu  Glu Glu Thr Leu Ala  Asp Leu Gly Leu Ser  Ser Phe Gly
    1250                1255                1260

Ile Ser  Asp Thr Pro Leu Glu  Glu Ile Phe Leu Lys  Val Thr Glu
    1265                1270                1275

Asp Ser  Asp Ser Gly Pro Leu  Phe Ala Gly Gly Ala  Gln Gln Lys
    1280                1285                1290

Arg Glu  Asn Val Asn Pro Arg  His Pro Cys Leu Gly  Pro Arg Glu
    1295                1300                1305

Lys Ala  Gly Gln Thr Pro Gln  Asp Ser Asn Val Cys  Ser Pro Gly
    1310                1315                1320

Ala Pro  Ala Ala His Pro Glu  Gly Gln Pro Pro Pro  Glu Pro Glu
    1325                1330                1335

Cys Pro  Gly Pro Gln Leu Asn  Thr Gly Thr Gln Leu  Val Leu Gln
    1340                1345                1350

His Val  Gln Ala Leu Leu Val  Lys Arg Phe Gln His  Thr Ile Arg
    1355                1360                1365

Ser His  Lys Asp Phe Leu Ala  Gln Ile Val Leu Pro  Ala Thr Phe
    1370                1375                1380

Val Phe  Leu Ala Leu Met Leu  Ser Ile Val Ile Leu  Pro Phe Gly
    1385                1390                1395

Glu Tyr  Pro Ala Leu Thr Leu  His Pro Trp Ile Tyr  Gly Gln Gln
    1400                1405                1410

Tyr Thr  Phe Phe Ser Met Asp  Glu Pro Gly Ser Glu  Gln Phe Thr
    1415                1420                1425

Val Leu  Ala Asp Val Leu Leu  Asn Lys Pro Gly Phe  Gly Asn Arg
    1430                1435                1440

Cys Leu  Lys Glu Gly Trp Leu  Pro Glu Tyr Pro Cys  Gly Asn Ser
    1445                1450                1455

Thr Pro  Trp Lys Thr Pro Ser  Val Ser Pro Asn Ile  Thr Gln Leu
    1460                1465                1470

Phe Gln  Lys Gln Lys Trp Thr  Gln Val Asn Pro Ser  Pro Ser Cys
    1475                1480                1485

Arg Cys  Ser Thr Arg Glu Lys  Leu Thr Met Leu Pro  Glu Cys Pro
    1490                1495                1500

Glu Gly  Ala Gly Gly Leu Pro  Pro Pro Gln Arg Thr  Gln Arg Ser
    1505                1510                1515

Thr Glu  Ile Leu Gln Asp Leu  Thr Asp Arg Asn Ile  Ser Asp Phe
    1520                1525                1530

Leu Val  Lys Thr Tyr Pro Ala  Leu Ile Arg Ser Ser  Leu Lys Ser
    1535                1540                1545

Lys Phe  Trp Val Asn Glu Gln  Arg Tyr Gly Gly Ile  Ser Ile Gly
    1550                1555                1560

Gly Lys  Leu Pro Val Val Pro  Ile Thr Gly Glu Ala  Leu Val Gly
    1565                1570                1575
```

```
Phe Leu Ser Asp Leu Gly Arg Ile Met Asn Val Ser Gly Gly Pro
    1580                1585                1590

Ile Thr Arg Glu Ala Ser Lys Glu Ile Pro Asp Phe Leu Lys His
    1595                1600                1605

Leu Glu Thr Glu Asp Asn Ile Lys Val Trp Phe Asn Asn Lys Gly
    1610                1615                1620

Trp His Ala Leu Val Ser Phe Leu Asn Val Ala His Asn Ala Ile
    1625                1630                1635

Leu Arg Ala Ser Leu Pro Lys Asp Arg Ser Pro Glu Glu Tyr Gly
    1640                1645                1650

Ile Thr Val Ile Ser Gln Pro Leu Asn Leu Thr Lys Glu Gln Leu
    1655                1660                1665

Ser Glu Ile Thr Val Leu Thr Thr Ser Val Asp Ala Val Val Ala
    1670                1675                1680

Ile Cys Val Ile Phe Ser Met Ser Phe Val Pro Ala Ser Phe Val
    1685                1690                1695

Leu Tyr Leu Ile Gln Glu Arg Val Asn Lys Ser Lys His Leu Gln
    1700                1705                1710

Phe Ile Ser Gly Val Ser Pro Thr Thr Tyr Trp Val Thr Asn Phe
    1715                1720                1725

Leu Trp Asp Ile Met Asn Tyr Ser Val Ser Ala Gly Leu Val Val
    1730                1735                1740

Gly Ile Phe Ile Gly Phe Gln Lys Lys Ala Tyr Thr Ser Pro Glu
    1745                1750                1755

Asn Leu Pro Ala Leu Val Ala Leu Leu Leu Leu Tyr Gly Trp Ala
    1760                1765                1770

Val Ile Pro Met Met Tyr Pro Ala Ser Phe Leu Phe Asp Val Pro
    1775                1780                1785

Ser Thr Ala Tyr Val Ala Leu Ser Cys Ala Asn Leu Phe Ile Gly
    1790                1795                1800

Ile Asn Ser Ser Ala Ile Thr Phe Ile Leu Glu Leu Phe Asp Asn
    1805                1810                1815

Asn Arg Thr Leu Leu Arg Phe Asn Ala Val Leu Arg Lys Leu Leu
    1820                1825                1830

Ile Val Phe Pro His Phe Cys Leu Gly Arg Gly Leu Ile Asp Leu
    1835                1840                1845

Ala Leu Ser Gln Ala Val Thr Asp Val Tyr Ala Arg Phe Gly Glu
    1850                1855                1860

Glu His Ser Ala Asn Pro Phe His Trp Asp Leu Ile Gly Lys Asn
    1865                1870                1875

Leu Phe Ala Met Val Val Glu Gly Val Val Tyr Phe Leu Leu Thr
    1880                1885                1890

Leu Leu Val Gln Arg His Phe Phe Leu Ser Gln Trp Ile Ala Glu
    1895                1900                1905

Pro Thr Lys Glu Pro Ile Val Asp Glu Asp Asp Asp Val Ala Glu
    1910                1915                1920

Glu Arg Gln Arg Ile Ile Thr Gly Gly Asn Lys Thr Asp Ile Leu
    1925                1930                1935

Arg Leu His Glu Leu Thr Lys Ile Tyr Leu Gly Thr Ser Ser Pro
    1940                1945                1950

Ala Val Asp Arg Leu Cys Val Gly Val Arg Pro Gly Glu Cys Phe
    1955                1960                1965

Gly Leu Leu Gly Val Asn Gly Ala Gly Lys Thr Thr Thr Phe Lys
    1970                1975                1980
```

```
Met Leu  Thr Gly Asp Thr Thr  Val Thr Ser Gly Asp  Ala Thr Val
    1985                 1990                 1995

Ala Gly  Lys Ser Ile Leu Thr  Asn Ile Ser Glu Val  His Gln Asn
    2000                 2005                 2010

Met Gly  Tyr Cys Pro Gln Phe  Asp Ala Ile Asp Glu  Leu Leu Thr
    2015                 2020                 2025

Gly Arg  Glu His Leu Tyr Leu  Tyr Ala Arg Leu Arg  Gly Val Pro
    2030                 2035                 2040

Ala Glu  Glu Ile Glu Lys Val  Ala Asn Trp Ser Ile  Lys Ser Leu
    2045                 2050                 2055

Gly Leu  Thr Val Tyr Ala Asp  Cys Leu Ala Gly Thr  Tyr Ser Gly
    2060                 2065                 2070

Gly Asn  Lys Arg Lys Leu Ser  Thr Ala Ile Ala Leu  Ile Gly Cys
    2075                 2080                 2085

Pro Pro  Leu Val Leu Leu Asp  Glu Pro Thr Thr Gly  Met Asp Pro
    2090                 2095                 2100

Gln Ala  Arg Arg Met Leu Trp  Asn Val Ile Val Ser  Ile Ile Arg
    2105                 2110                 2115

Lys Gly  Arg Ala Val Val Leu  Thr Ser His Ser Met  Glu Glu Cys
    2120                 2125                 2130

Glu Ala  Leu Cys Thr Arg Leu  Ala Ile Met Val Lys  Gly Ala Phe
    2135                 2140                 2145

Arg Cys  Met Gly Thr Ile Gln  His Leu Lys Ser Lys  Phe Gly Asp
    2150                 2155                 2160

Gly Tyr  Ile Val Thr Met Lys  Ile Lys Ser Pro Lys  Asp Asp Leu
    2165                 2170                 2175

Leu Pro  Asp Leu Asn Pro Val  Glu Gln Phe Phe Gln  Gly Asn Phe
    2180                 2185                 2190

Pro Gly  Ser Val Gln Arg Glu  Arg His Tyr Asn Met  Leu Gln Phe
    2195                 2200                 2205

Gln Val  Ser Ser Ser Ser Leu  Ala Arg Ile Phe Gln  Leu Leu Leu
    2210                 2215                 2220

Ser His  Lys Asp Ser Leu Leu  Ile Glu Glu Tyr Ser  Val Thr Gln
    2225                 2230                 2235

Thr Thr  Leu Asp Gln Val Phe  Val Asn Phe Ala Lys  Gln Gln Thr
    2240                 2245                 2250

Glu Ser  His Asp Leu Pro Leu  His Pro Arg Ala Ala  Gly Ala Ser
    2255                 2260                 2265

Arg Gln  Ala Gln Asp
    2270
```

<210> SEQ ID NO 4
<211> LENGTH: 114
<212> TYPE: DNA
<213> ORGANISM: Homo sapiens

<400> SEQUENCE: 4

```
ggagtacccc tgtggcaact caacaccctg gaagactcct tctgtgtccc caaacatcac     60

ccagctgttc cagaagcaga aatggacaca ggtcaaccct tcaccatcct gcag          114
```

<210> SEQ ID NO 5
<211> LENGTH: 6705
<212> TYPE: DNA
<213> ORGANISM: Homo sapiens

<400> SEQUENCE: 5

```
atgggcttcg tgagacagat acagcttttg ctctggaaga actggaccct gcggaaaagg     60
caaaagattc gctttgtggt ggaactcgtg tggcctttat ctttatttct ggtcttgatc    120
tggttaagga atgccaaccc gctctacagc catcatgaat gccatttccc caacaaggcg    180
atgccctcag caggaatgct gccgtggctc caggggatct tctgcaatgt gaacaatccc    240
tgttttcaaa gccccaccc aggagaatct cctggaattg tgtcaaacta taacaactcc     300
atcttggcaa gggtatatcg agattttcaa gaactcctca tgaatgcacc agagagccag    360
caccttggcc gtatttggac agagctacac atcttgtccc aattcatgga caccctccgg    420
actcacccgg agagaattgc aggaagagga atacgaataa gggatatctt gaaagatgaa    480
gaaacactga cactatttct cattaaaaac atcggcctgt ctgactcagt ggtctacctt    540
ctgatcaact ctcaagtccg tccagagcag ttcgctcatg gagtcccgga cctggcgctg    600
aaggacatcg cctgcagcga ggccctcctg gagcgcttca tcatcttcag ccagagacgc    660
ggggcaaaga cggtgcgcta tgccctgtgc tccctctccc agggcaccct acagtggata    720
gaagacactc tgtatgccaa cgtggacttc ttcaagctct tccgtgtgct tcccacactc    780
ctagacagcc gttctcaagg tatcaatctg agatcttggg gaggaatatt atctgatatg    840
tcaccaagaa ttcaagagtt tatccatcgg ccgagtatgc aggacttgct gtgggtgacc    900
aggcccctca tgcagaatgg tggtccagag acctttacaa agctgatggg catcctgtct    960
gacctcctgt gtggctaccc cgagggaggt ggctctcggg tgctctcctt caactggtat   1020
gaagacaata actataaggc ctttctgggg attgactcca caaggaagga tcctatctat   1080
tcttatgaca gaagaacaac atccttttgt aatgcattga tccagagcct ggagtcaaat   1140
cctttaacca aaatcgcttg gagggcggca aagcctttgc tgatgggaaa aatcctgtac   1200
actcctgatt cacctgcagc acgaaggata ctgaagaatg ccaactcaac ttttgaagaa   1260
ctggaacacg ttaggaagtt ggtcaaagcc tgggaagaag tagggcccca gatctggtac   1320
ttctttgaca acagcacaca gatgaacatg atcagagata ccctggggaa cccaacagta   1380
aaagactttt tgaataggca gcttggtgaa gaaggtatta ctgctgaagc catcctaaac   1440
ttcctctaca agggccctcg ggaaagccag gctgacgaca tggccaactt cgactggagg   1500
gacatattta acatcactga tcgcaccctc cgcctggtca atcaatacct ggagtgcttg   1560
gtcctggata agtttgaaag ctacaatgat gaaactcagc tcacccaacg tgccctctct   1620
ctactggagg aaaacatgtt ctgggccgga gtggtattcc ctgacatgta tccctggacc   1680
agctctctac caccccacgt gaagtataag atccgaatgg acatagacgt ggtggagaaa   1740
accaataaga ttaaagacag gtattgggat tctggtccca gagctgatcc cgtggaagat   1800
ttccggtaca tctggggcgg gtttgcctat ctgcaggaca tggttgaaca ggggatcaca   1860
aggagccagg tgcaggcgga ggctccagtt ggaatctacc tccagcagat gccctacccc   1920
tgcttcgtgg acgattcttt catgatcatc ctgaaccgct gtttccctat cttcatggtg   1980
ctggcatgga tctactctgt ctccatgact gtgaagagca tcgtcttgga gaaggagttg   2040
cgactgaagg agaccttgaa aaatcagggt gtctccaatg cagtgatttg gtgtacctgg   2100
ttcctggaca gcttctccat catgtcgatg agcatcttcc tcctgacgat attcatcatg   2160
catggaagaa tcctacatta cagcgaccca ttcatcctct tcctgttctt gttggctttc   2220
tccactgcca ccatcatgct gtgctttctg ctcagcacct tcttctccaa ggccagtctg   2280
gcagcagcct gtagtggtgt catctatttc accctctacc tgccacacat cctgtgcttc   2340
gcctggcagg accgcatgac cgctgagctg aagaaggctg tgagcttact gtctccggtg   2400
```

```
gcatttggat ttggcactga gtacctggtt cgctttgaag agcaaggcct ggggctgcag   2460

tggagcaaca tcgggaacag tcccacggaa ggggacgaat tcagcttcct gctgtccatg   2520

cagatgatgc tccttgatgc tgcgtgctat ggcttactcg cttggtacct tgatcaggtg   2580

tttccaggag actatggaac cccacttcct tggtactttc ttctacaaga gtcgtattgg   2640

cttagcggtg aagggtgttc aaccagagaa gaaagagccc tggaaaagac cgagccccta   2700

acagaggaaa cggaggatcc agagcaccca gaaggaatac acgactcctt ctttgaacgt   2760

gagcatccag ggtgggttcc tggggtatgc gtgaagaatc tggtaaagat tttgagcccc   2820

tgtggccggc cagctgtgga ccgtctgaac atcaccttct acgagaacca gatcaccgca   2880

ttcctgggcc acaatggagc tgggaaaacc accaccttgt ccatcctgac gggtctgttg   2940

ccaccaacct ctgggactgt gctcgttggg ggaagggaca ttgaaaccag cctggatgca   3000

gtccggcaga gccttggcat gtgtccacag cacaacatcc tgttccacca cctcacggtg   3060

gctgagcaca tgctgttcta tgcccagctg aaaggaaagt cccaggagga ggcccagctg   3120

gagatggaag ccatgttgga ggacacaggc ctccaccaca agcggaatga agaggctcag   3180

gacctatcag gtggcatgca gagaaagctg tcggttgcca ttgcctttgt gggagatgcc   3240

aaggtggtga ttctggacga acccacctct ggggtggacc cttactcgag acgctcaatc   3300

tgggatctgc tcctgaagta tcgctcaggc agaaccatca tcatgcccac tcaccacatg   3360

gacgaggccg accaccaagg ggaccgcatt gccatcattg cccagggaag gctctactgc   3420

tcaggcaccc cactcttcct gaagaactgc tttggcacag gcttgtactt aaccttggtg   3480

cgcaagatga aaaacatcca gagccaaagg aaaggcagtg aggggacctg cagctgctcg   3540

tctaagggtt tctccaccac gtgtccagcc cacgtcgatg acctaactcc agaacaagtc   3600

ctggatgggg atgtaaatga gctgatggat gtagttctcc accatgttcc agaggcaaag   3660

ctggtggagt gcattggtca agaacttatc ttccttcttc caaataagaa cttcaagcac   3720

agagcatatg ccagcctttt cagagagctg gaggagacgc tggctgacct tggtctcagc   3780

agttttggaa tttctgacac tcccctggaa gagatttttc tgaaggtcac ggaggattct   3840

gattcaggac ctctgtttgc gggtggcgct cagcagaaaa gagaaaacgt caaccccccga   3900

cacccctgct tgggtcccag agagaaggct ggacagacac cccaggactc caatgtctgc   3960

tccccagggg cgccggctgc tcacccagag ggccagcctc ccccagagcc agagtgccca   4020

ggcccgcagc tcaacacggg gacacagctg gtcctccagc atgtgcaggc gctgctggtc   4080

aagagattcc aacacaccat ccgcagccac aaggacttcc tggcgcagat cgtgctcccg   4140

gctacctttg tgtttttggc tctgatgctt tctattgtta tccttccttt tggcgaatac   4200

cccgctttga cccttcaccc ctggatatat gggcagcagt acaccttctt cagcatggat   4260

gaaccaggca gtgagcagtt cacggtactt gcagacgtcc tcctgaataa gccaggcttt   4320

ggcaaccgct gcctgaagga agggtggctt ccgtgcagca ccagggagaa gctcaccatg   4380

ctgccagagt gccccgaggg tgccgggggc ctcccgcccc cccagagaac acagcgcagc   4440

acggaaattc tacaagacct gacggacagg aacatctccg acttcttggt aaaaacgtat   4500

cctgctctta taagaagcag cttaaagagc aaattctggg tcaatgaaca gaggtatgga   4560

ggaatttcca ttggaggaaa gctcccagtc gtccccatca cgggggaagc acttgttggg   4620

tttttaagcg accttggccg gatcatgaat gtgagcgggg gccctatcac tagagaggcc   4680

tctaaagaaa tacctgattt ccttaaacat ctagaaactg aagacaacat taaggtgtgg   4740

tttaataaca aaggctggca tgccctggtc agctttctca atgtggccca caacgccatc   4800
```

```
ttacgggcca gcctgcctaa ggacaggagc cccgaggagt atggaatcac cgtcattagc   4860

caacccctga acctgaccaa ggagcagctc tcagagatta cagtgctgac cacttcagtg   4920

gatgctgtgg ttgccatctg cgtgattttc tccatgtcct tcgtcccagc cagctttgtc   4980

ctttatttga tccaggagcg ggtgaacaaa tccaagcacc tccagtttat cagtggagtg   5040

agccccacca cctactgggt gaccaacttc ctctgggaca tcatgaatta ttccgtgagt   5100

gctgggctgg tggtgggcat cttcatcggg tttcagaaga aagcctacac ttctccagaa   5160

aaccttcctg cccttgtggc actgctcctg ctgtatggat gggcggtcat tcccatgatg   5220

tacccagcat ccttcctgtt tgatgtcccc agcacagcct atgtggcttt atcttgtgct   5280

aatctgttca tcggcatcaa cagcagtgct attaccttca tcttggaatt atttgataat   5340

aaccggacgc tgctcaggtt caacgccgtg ctgaggaagc tgctcattgt cttcccccac   5400

ttctgcctgg gccggggcct cattgacctt gcactgagcc aggctgtgac agatgtctat   5460

gcccggtttg gtgaggagca ctctgcaaat ccgttccact gggacctgat tgggaagaac   5520

ctgtttgcca tggtggtgga aggggtggtg tacttcctcc tgaccctgct ggtccagcgc   5580

cacttcttcc tctcccaatg gattgccgag cccactaagg agcccattgt tgatgaagat   5640

gatgatgtgg ctgaagaaag acaaagaatt attactggtg gaaataaaac tgacatctta   5700

aggctacatg aactaaccaa gatttatctg ggcacctcca gcccagcagt ggacaggctg   5760

tgtgtcggag ttcgccctgg agagtgcttt ggcctcctgg gagtgaatgg tgccggcaaa   5820

acaaccacat tcaagatgct cactggggac accacagtga cctcagggga tgccaccgta   5880

gcaggcaaga gtattttaac caatatttct gaagtccatc aaaatatggg ctactgtcct   5940

cagtttgatg caatcgatga gctgctcaca ggacgagaac atctttacct ttatgcccgg   6000

cttcgaggtg taccagcaga agaaatcgaa aaggttgcaa actggagtat taagagcctg   6060

ggcctgactg tctacgccga ctgcctggct ggcacgtaca gtgggggcaa caagcggaaa   6120

ctctccacag ccatcgcact cattggctgc ccaccgctgg tgctgctgga tgagcccacc   6180

acagggatgg acccccaggc acgccgcatg ctgtggaacg tcatcgtgag catcatcaga   6240

aaagggaggg ctgtggtcct cacatcccac agcatggaag aatgtgaggc actgtgtacc   6300

cggctggcca tcatggtaaa gggcgccttt cgatgtatgg gcaccattca gcatctcaag   6360

tccaaatttg gagatggcta tatcgtcaca atgaagatca aatccccgaa ggacgacctg   6420

cttcctgacc tgaaccctgt ggagcagttc ttccagggga acttcccagg cagtgtgcag   6480

agggagaggc actacaacat gctccagttc caggtctcct cctcctccct ggcgaggatc   6540

ttccagctcc tcctctccca caaggacagc ctgctcatcg aggagtactc agtcacacag   6600

accacactgg accaggtgtt tgtaaatttt gctaaacagc agactgaaag tcatgacctc   6660

cctctgcacc ctcgagctgc tggagccagt cgacaagccc aggac                   6705
```

<210> SEQ ID NO 6
<211> LENGTH: 2235
<212> TYPE: PRT
<213> ORGANISM: Homo sapiens

<400> SEQUENCE: 6

```
Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
```

-continued

```
        35                  40                  45

Tyr Ser His His Glu Cys His Phe Pro Asn Lys Ala Met Pro Ser Ala
    50                  55                  60

Gly Met Leu Pro Trp Leu Gln Gly Ile Phe Cys Asn Val Asn Asn Pro
65                  70                  75                  80

Cys Phe Gln Ser Pro Thr Pro Gly Glu Ser Pro Gly Ile Val Ser Asn
                85                  90                  95

Tyr Asn Asn Ser Ile Leu Ala Arg Val Tyr Arg Asp Phe Gln Glu Leu
            100                 105                 110

Leu Met Asn Ala Pro Glu Ser Gln His Leu Gly Arg Ile Trp Thr Glu
        115                 120                 125

Leu His Ile Leu Ser Gln Phe Met Asp Thr Leu Arg Thr His Pro Glu
    130                 135                 140

Arg Ile Ala Gly Arg Gly Ile Arg Ile Arg Asp Ile Leu Lys Asp Glu
145                 150                 155                 160

Glu Thr Leu Thr Leu Phe Leu Ile Lys Asn Ile Gly Leu Ser Asp Ser
                165                 170                 175

Val Val Tyr Leu Leu Ile Asn Ser Gln Val Arg Pro Glu Gln Phe Ala
            180                 185                 190

His Gly Val Pro Asp Leu Ala Leu Lys Asp Ile Ala Cys Ser Glu Ala
        195                 200                 205

Leu Leu Glu Arg Phe Ile Ile Phe Ser Gln Arg Arg Gly Ala Lys Thr
    210                 215                 220

Val Arg Tyr Ala Leu Cys Ser Leu Ser Gln Gly Thr Leu Gln Trp Ile
225                 230                 235                 240

Glu Asp Thr Leu Tyr Ala Asn Val Asp Phe Phe Lys Leu Phe Arg Val
                245                 250                 255

Leu Pro Thr Leu Leu Asp Ser Arg Ser Gln Gly Ile Asn Leu Arg Ser
            260                 265                 270

Trp Gly Gly Ile Leu Ser Asp Met Ser Pro Arg Ile Gln Glu Phe Ile
        275                 280                 285

His Arg Pro Ser Met Gln Asp Leu Leu Trp Val Thr Arg Pro Leu Met
    290                 295                 300

Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Gly Ser Arg Val Leu Ser
                325                 330                 335

Phe Asn Trp Tyr Glu Asp Asn Asn Tyr Lys Ala Phe Leu Gly Ile Asp
            340                 345                 350

Ser Thr Arg Lys Asp Pro Ile Tyr Ser Tyr Asp Arg Arg Thr Thr Ser
        355                 360                 365

Phe Cys Asn Ala Leu Ile Gln Ser Leu Glu Ser Asn Pro Leu Thr Lys
    370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
                405                 410                 415

Thr Phe Glu Glu Leu Glu His Val Arg Lys Leu Val Lys Ala Trp Glu
            420                 425                 430

Glu Val Gly Pro Gln Ile Trp Tyr Phe Phe Asp Asn Ser Thr Gln Met
        435                 440                 445

Asn Met Ile Arg Asp Thr Leu Gly Asn Pro Thr Val Lys Asp Phe Leu
    450                 455                 460
```

```
Asn Arg Gln Leu Gly Glu Glu Gly Ile Thr Ala Glu Ala Ile Leu Asn
465                 470                 475                 480

Phe Leu Tyr Lys Gly Pro Arg Glu Ser Gln Ala Asp Asp Met Ala Asn
                485                 490                 495

Phe Asp Trp Arg Asp Ile Phe Asn Ile Thr Asp Arg Thr Leu Arg Leu
            500                 505                 510

Val Asn Gln Tyr Leu Glu Cys Leu Val Leu Asp Lys Phe Glu Ser Tyr
        515                 520                 525

Asn Asp Glu Thr Gln Leu Thr Gln Arg Ala Leu Ser Leu Leu Glu Glu
    530                 535                 540

Asn Met Phe Trp Ala Gly Val Val Phe Pro Asp Met Tyr Pro Trp Thr
545                 550                 555                 560

Ser Ser Leu Pro Pro His Val Lys Tyr Lys Ile Arg Met Asp Ile Asp
                565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
        595                 600                 605

Ala Tyr Leu Gln Asp Met Val Glu Gln Gly Ile Thr Arg Ser Gln Val
    610                 615                 620

Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
                645                 650                 655

Ile Phe Met Val Leu Ala Trp Ile Tyr Ser Val Ser Met Thr Val Lys
            660                 665                 670

Ser Ile Val Leu Glu Lys Glu Leu Arg Leu Lys Glu Thr Leu Lys Asn
        675                 680                 685

Gln Gly Val Ser Asn Ala Val Ile Trp Cys Thr Trp Phe Leu Asp Ser
    690                 695                 700

Phe Ser Ile Met Ser Met Ser Ile Phe Leu Leu Thr Ile Phe Ile Met
705                 710                 715                 720

His Gly Arg Ile Leu His Tyr Ser Asp Pro Phe Ile Leu Phe Leu Phe
                725                 730                 735

Leu Leu Ala Phe Ser Thr Ala Thr Ile Met Leu Cys Phe Leu Leu Ser
            740                 745                 750

Thr Phe Phe Ser Lys Ala Ser Leu Ala Ala Ala Cys Ser Gly Val Ile
        755                 760                 765

Tyr Phe Thr Leu Tyr Leu Pro His Ile Leu Cys Phe Ala Trp Gln Asp
    770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
                805                 810                 815

Leu Gly Leu Gln Trp Ser Asn Ile Gly Asn Ser Pro Thr Glu Gly Asp
            820                 825                 830

Glu Phe Ser Phe Leu Leu Ser Met Gln Met Met Leu Leu Asp Ala Ala
        835                 840                 845

Cys Tyr Gly Leu Leu Ala Trp Tyr Leu Asp Gln Val Phe Pro Gly Asp
    850                 855                 860

Tyr Gly Thr Pro Leu Pro Trp Tyr Phe Leu Leu Gln Glu Ser Tyr Trp
865                 870                 875                 880

Leu Ser Gly Glu Gly Cys Ser Thr Arg Glu Glu Arg Ala Leu Glu Lys
                885                 890                 895
```

```
Thr Glu Pro Leu Thr Glu Glu Thr Glu Asp Pro Glu His Pro Glu Gly
            900                 905                 910

Ile His Asp Ser Phe Phe Glu Arg Glu His Pro Gly Trp Val Pro Gly
        915                 920                 925

Val Cys Val Lys Asn Leu Val Lys Ile Phe Glu Pro Cys Gly Arg Pro
    930                 935                 940

Ala Val Asp Arg Leu Asn Ile Thr Phe Tyr Glu Asn Gln Ile Thr Ala
945                 950                 955                 960

Phe Leu Gly His Asn Gly Ala Gly Lys Thr Thr Thr Leu Ser Ile Leu
                965                 970                 975

Thr Gly Leu Leu Pro Pro Thr Ser Gly Thr Val Leu Val Gly Gly Arg
            980                 985                 990

Asp Ile Glu Thr Ser Leu Asp Ala  Val Arg Gln Ser Leu  Gly Met Cys
        995                 1000                1005

Pro Gln  His Asn Ile Leu Phe  His His Leu Thr Val  Ala Glu His
    1010                1015                1020

Met Leu  Phe Tyr Ala Gln Leu  Lys Gly Lys Ser Gln  Glu Glu Ala
    1025                1030                1035

Gln Leu  Glu Met Glu Ala Met  Leu Glu Asp Thr Gly  Leu His His
    1040                1045                1050

Lys Arg  Asn Glu Glu Ala Gln  Asp Leu Ser Gly Gly  Met Gln Arg
    1055                1060                1065

Lys Leu  Ser Val Ala Ile Ala  Phe Val Gly Asp Ala  Lys Val Val
    1070                1075                1080

Ile Leu  Asp Glu Pro Thr Ser  Gly Val Asp Pro Tyr  Ser Arg Arg
    1085                1090                1095

Ser Ile  Trp Asp Leu Leu Leu  Lys Tyr Arg Ser Gly  Arg Thr Ile
    1100                1105                1110

Ile Met  Pro Thr His His Met  Asp Glu Ala Asp His  Gln Gly Asp
    1115                1120                1125

Arg Ile  Ala Ile Ile Ala Gln  Gly Arg Leu Tyr Cys  Ser Gly Thr
    1130                1135                1140

Pro Leu  Phe Leu Lys Asn Cys  Phe Gly Thr Gly Leu  Tyr Leu Thr
    1145                1150                1155

Leu Val  Arg Lys Met Lys Asn  Ile Gln Ser Gln Arg  Lys Gly Ser
    1160                1165                1170

Glu Gly  Thr Cys Ser Cys Ser  Ser Lys Gly Phe Ser  Thr Thr Cys
    1175                1180                1185

Pro Ala  His Val Asp Asp Leu  Thr Pro Glu Gln Val  Leu Asp Gly
    1190                1195                1200

Asp Val  Asn Glu Leu Met Asp  Val Val Leu His His  Val Pro Glu
    1205                1210                1215

Ala Lys  Leu Val Glu Cys Ile  Gly Gln Glu Leu Ile  Phe Leu Leu
    1220                1225                1230

Pro Asn  Lys Asn Phe Lys His  Arg Ala Tyr Ala Ser  Leu Phe Arg
    1235                1240                1245

Glu Leu  Glu Glu Thr Leu Ala  Asp Leu Gly Leu Ser  Ser Phe Gly
    1250                1255                1260

Ile Ser  Asp Thr Pro Leu Glu  Glu Ile Phe Leu Lys  Val Thr Glu
    1265                1270                1275

Asp Ser  Asp Ser Gly Pro Leu  Phe Ala Gly Gly Ala  Gln Gln Lys
    1280                1285                1290

Arg Glu  Asn Val Asn Pro Arg  His Pro Cys Leu Gly  Pro Arg Glu
```

-continued

```
    1295                1300                1305

Lys Ala  Gly Gln Thr Pro Gln  Asp Ser Asn Val Cys  Ser Pro Gly
    1310                1315                1320

Ala Pro  Ala Ala His Pro Glu  Gly Gln Pro Pro Pro  Glu Pro Glu
    1325                1330                1335

Cys Pro  Gly Pro Gln Leu Asn  Thr Gly Thr Gln Leu  Val Leu Gln
    1340                1345                1350

His Val  Gln Ala Leu Leu Val  Lys Arg Phe Gln His  Thr Ile Arg
    1355                1360                1365

Ser His  Lys Asp Phe Leu Ala  Gln Ile Val Leu Pro  Ala Thr Phe
    1370                1375                1380

Val Phe  Leu Ala Leu Met Leu  Ser Ile Val Ile Leu  Pro Phe Gly
    1385                1390                1395

Glu Tyr  Pro Ala Leu Thr Leu  His Pro Trp Ile Tyr  Gly Gln Gln
    1400                1405                1410

Tyr Thr  Phe Phe Ser Met Asp  Glu Pro Gly Ser Glu  Gln Phe Thr
    1415                1420                1425

Val Leu  Ala Asp Val Leu Leu  Asn Lys Pro Gly Phe  Gly Asn Arg
    1430                1435                1440

Cys Leu  Lys Glu Gly Trp Leu  Pro Cys Ser Thr Arg  Glu Lys Leu
    1445                1450                1455

Thr Met  Leu Pro Glu Cys Pro  Glu Gly Ala Gly Gly  Leu Pro Pro
    1460                1465                1470

Pro Gln  Arg Thr Gln Arg Ser  Thr Glu Ile Leu Gln  Asp Leu Thr
    1475                1480                1485

Asp Arg  Asn Ile Ser Asp Phe  Leu Val Lys Thr Tyr  Pro Ala Leu
    1490                1495                1500

Ile Arg  Ser Ser Leu Lys Ser  Lys Phe Trp Val Asn  Glu Gln Arg
    1505                1510                1515

Tyr Gly  Gly Ile Ser Ile Gly  Gly Lys Leu Pro Val  Val Pro Ile
    1520                1525                1530

Thr Gly  Glu Ala Leu Val Gly  Phe Leu Ser Asp Leu  Gly Arg Ile
    1535                1540                1545

Met Asn  Val Ser Gly Gly Pro  Ile Thr Arg Glu Ala  Ser Lys Glu
    1550                1555                1560

Ile Pro  Asp Phe Leu Lys His  Leu Glu Thr Glu Asp  Asn Ile Lys
    1565                1570                1575

Val Trp  Phe Asn Asn Lys Gly  Trp His Ala Leu Val  Ser Phe Leu
    1580                1585                1590

Asn Val  Ala His Asn Ala Ile  Leu Arg Ala Ser Leu  Pro Lys Asp
    1595                1600                1605

Arg Ser  Pro Glu Glu Tyr Gly  Ile Thr Val Ile Ser  Gln Pro Leu
    1610                1615                1620

Asn Leu  Thr Lys Glu Gln Leu  Ser Glu Ile Thr Val  Leu Thr Thr
    1625                1630                1635

Ser Val  Asp Ala Val Val Ala  Ile Cys Val Ile Phe  Ser Met Ser
    1640                1645                1650

Phe Val  Pro Ala Ser Phe Val  Leu Tyr Leu Ile Gln  Glu Arg Val
    1655                1660                1665

Asn Lys  Ser Lys His Leu Gln  Phe Ile Ser Gly Val  Ser Pro Thr
    1670                1675                1680

Thr Tyr  Trp Val Thr Asn Phe  Leu Trp Asp Ile Met  Asn Tyr Ser
    1685                1690                1695
```

```
Val Ser  Ala Gly Leu Val Val  Gly Ile Phe Ile Gly  Phe Gln Lys
    1700                 1705                 1710

Lys Ala  Tyr Thr Ser Pro Glu  Asn Leu Pro Ala Leu  Val Ala Leu
    1715                 1720                 1725

Leu Leu  Leu Tyr Gly Trp Ala  Val Ile Pro Met Met  Tyr Pro Ala
    1730                 1735                 1740

Ser Phe  Leu Phe Asp Val Pro  Ser Thr Ala Tyr Val  Ala Leu Ser
    1745                 1750                 1755

Cys Ala  Asn Leu Phe Ile Gly  Ile Asn Ser Ser Ala  Ile Thr Phe
    1760                 1765                 1770

Ile Leu  Glu Leu Phe Asp Asn  Asn Arg Thr Leu Leu  Arg Phe Asn
    1775                 1780                 1785

Ala Val  Leu Arg Lys Leu Leu  Ile Val Phe Pro His  Phe Cys Leu
    1790                 1795                 1800

Gly Arg  Gly Leu Ile Asp Leu  Ala Leu Ser Gln Ala  Val Thr Asp
    1805                 1810                 1815

Val Tyr  Ala Arg Phe Gly Glu  Glu His Ser Ala Asn  Pro Phe His
    1820                 1825                 1830

Trp Asp  Leu Ile Gly Lys Asn  Leu Phe Ala Met Val  Val Glu Gly
    1835                 1840                 1845

Val Val  Tyr Phe Leu Leu Thr  Leu Leu Val Gln Arg  His Phe Phe
    1850                 1855                 1860

Leu Ser  Gln Trp Ile Ala Glu  Pro Thr Lys Glu Pro  Ile Val Asp
    1865                 1870                 1875

Glu Asp  Asp Asp Val Ala Glu  Glu Arg Gln Arg Ile  Ile Thr Gly
    1880                 1885                 1890

Gly Asn  Lys Thr Asp Ile Leu  Arg Leu His Glu Leu  Thr Lys Ile
    1895                 1900                 1905

Tyr Leu  Gly Thr Ser Ser Pro  Ala Val Asp Arg Leu  Cys Val Gly
    1910                 1915                 1920

Val Arg  Pro Gly Glu Cys Phe  Gly Leu Leu Gly Val  Asn Gly Ala
    1925                 1930                 1935

Gly Lys  Thr Thr Thr Phe Lys  Met Leu Thr Gly Asp  Thr Thr Val
    1940                 1945                 1950

Thr Ser  Gly Asp Ala Thr Val  Ala Gly Lys Ser Ile  Leu Thr Asn
    1955                 1960                 1965

Ile Ser  Glu Val His Gln Asn  Met Gly Tyr Cys Pro  Gln Phe Asp
    1970                 1975                 1980

Ala Ile  Asp Glu Leu Leu Thr  Gly Arg Glu His Leu  Tyr Leu Tyr
    1985                 1990                 1995

Ala Arg  Leu Arg Gly Val Pro  Ala Glu Glu Ile Glu  Lys Val Ala
    2000                 2005                 2010

Asn Trp  Ser Ile Lys Ser Leu  Gly Leu Thr Val Tyr  Ala Asp Cys
    2015                 2020                 2025

Leu Ala  Gly Thr Tyr Ser Gly  Gly Asn Lys Arg Lys  Leu Ser Thr
    2030                 2035                 2040

Ala Ile  Ala Leu Ile Gly Cys  Pro Pro Leu Val Leu  Leu Asp Glu
    2045                 2050                 2055

Pro Thr  Thr Gly Met Asp Pro  Gln Ala Arg Arg Met  Leu Trp Asn
    2060                 2065                 2070

Val Ile  Val Ser Ile Ile Arg  Lys Gly Arg Ala Val  Val Leu Thr
    2075                 2080                 2085

Ser His  Ser Met Glu Glu Cys  Glu Ala Leu Cys Thr  Arg Leu Ala
    2090                 2095                 2100
```

```
Ile Met  Val Lys Gly Ala Phe  Arg Cys Met Gly Thr  Ile Gln His
    2105                 2110                 2115

Leu Lys  Ser Lys Phe Gly Asp  Gly Tyr Ile Val Thr  Met Lys Ile
    2120                 2125                 2130

Lys Ser  Pro Lys Asp Asp Leu  Leu Pro Asp Leu Asn  Pro Val Glu
    2135                 2140                 2145

Gln Phe  Phe Gln Gly Asn Phe  Pro Gly Ser Val Gln  Arg Glu Arg
    2150                 2155                 2160

His Tyr  Asn Met Leu Gln Phe  Gln Val Ser Ser Ser  Ser Leu Ala
    2165                 2170                 2175

Arg Ile  Phe Gln Leu Leu Leu  Ser His Lys Asp Ser  Leu Leu Ile
    2180                 2185                 2190

Glu Glu  Tyr Ser Val Thr Gln  Thr Thr Leu Asp Gln  Val Phe Val
    2195                 2200                 2205

Asn Phe  Ala Lys Gln Gln Thr  Glu Ser His Asp Leu  Pro Leu His
    2210                 2215                 2220

Pro Arg  Ala Ala Gly Ala Ser  Arg Gln Ala Gln Asp
    2225                 2230                 2235


<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:  Primer

<400> SEQUENCE: 7

atcctctgac tcagcaatca ca                                          22


<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 8

ttgcaattac aaatgcaatg g                                           21


<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 9

atccataccc ttcccactcc                                             20


<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 10

gcagcagaag ataagcacac c                                           21


<210> SEQ ID NO 11
<211> LENGTH: 38
<212> TYPE: PRT
```

<213> ORGANISM: Homo sapiens

<400> SEQUENCE: 11

```
Glu Tyr Pro Cys Gly Asn Ser Thr Pro Trp Lys Thr Pro Ser Val Ser
1               5                   10                  15

Pro Asn Ile Thr Gln Leu Phe Gln Lys Gln Lys Trp Thr Gln Val Asn
            20                  25                  30

Pro Ser Pro Ser Cys Arg
        35
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
accctctgct aagctcagag 20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 13
accccacact tccaacctg 19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
aagtcctact gcacacatgg 20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 15
acactcccac cccaagatc 19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 16
ttcccaaaaa ggccaactc 19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 17
cacgcacgtg tgcattcag 19

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
gctatttcct tattaatgag gc 22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
ccaactctcc ctgttctttc 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
tgtttccaat cgactctggc 20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 21
ttcttgcctt tctcaggctg g 21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 22
gtattcccag gttctgtgg 19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 23
taccccagga atcaccttg 19

<210> SEQ ID NO 24
<211> LENGTH: 21

```
<212> TYPE: DNA
<213> ORGANISM: Artificial Sequence
<220> FEATURE:
<223> OTHER INFORMATION: Description of Artificial Sequence:  Primer

<400> SEQUENCE: 24

agcatatagg agatcagact g                                              21


<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 25

tgacataagt ggggtaaatg g                                              21


<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 26

gagcattggc ctcacagcag                                                20


<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:  Primer

<400> SEQUENCE: 27

ccccaggttt gtttcacc                                                  18


<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 28

agacatgtga tgtggataca c                                              21


<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 29

gtgggaggtc cagggtacac                                                20


<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence:  Primer

<400> SEQUENCE: 30

aggggcagaa aagacacac                                                 19
```

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 31
tagcgattaa ctctttcctg g 21

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 32
ctcttcaggg agccttagc 19

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 33
ttcaagacca cttgacttgc 20

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 34
tgggacagca gccttatc 18

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 35
ccaaatgtaa tttcccactg ac 22

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 36
aatgagttcc gagtcaccct g 21

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 37
cccattcgcg tgtcatgg 18

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 38
tccatctggg ctttgttctc 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 39
aatccaggca catgaacagg 20

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 40
aggctggtgg gagagagc 18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 41
agtggacccc ctcagagg 18

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 42
ctgttgcatt ggataaaagg c 21

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 43
gatgaatgga gagggctgg 19

<210> SEQ ID NO 44
<211> LENGTH: 21

```
<212> TYPE: DNA
<213> ORGANISM: Artificial Sequence
<220> FEATURE:
<223> OTHER INFORMATION: Description of Artificial Sequence:  Primer

<400> SEQUENCE: 44

ctgcggtaag gtaggatagg g                                              21


<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 45

cacaccgttt acatagaggg c                                              21


<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence:  Primer

<400> SEQUENCE: 46

cctctcccct cctttcctg                                                 19


<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence:  Primer

<400> SEQUENCE: 47

gtcagtttcc gtaggcttc                                                 19


<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence:  Primer

<400> SEQUENCE: 48

tggggccatg taattaggc                                                 19


<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 49

tgggaaagag tagacagccg                                                20


<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:  Primer

<400> SEQUENCE: 50

actgaacctg gtgtgggg                                                  18
```

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 51
tatctctgcc tgtgcccag 19

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 52
gtaagatcag ctgctggaag 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 53
gaagctctcc tgcaccaagc 20

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 54
aggtaccccc acaatgcc 18

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 55
tcattgtggt tccagtactc ag 22

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 56
tttttgcaac tatatagcca gg 22

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 57
agcctgtgtg agtagccatg 20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 58
gcatcagggc gaggctgtc 19

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 59
cccagcaata ctgggagatg 20

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 60
ggtaacctca cagtcttcc 19

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 61
gggaacgatg gctttttgc 19

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 62
tcccattatg aagcaatacc 20

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 63
ccttagactt tcgagatgg 19

<210> SEQ ID NO 64
<211> LENGTH: 23

```
<212> TYPE: DNA
<213> ORGANISM: Artificial Sequence
<220> FEATURE:
<223> OTHER INFORMATION: Description of Artificial Sequence:  Primer

<400> SEQUENCE: 64

gctaccagcc tggtatttca ttg                                            23


<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 65

gttataaccc atgcctgaag                                                20


<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence:  Primer

<400> SEQUENCE: 66

tgcacgcgca cgtgtgac                                                  18


<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 67

tgaaggtccc agtgaagtgg g                                              21


<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 68

cagcagctat ccagtaaagg                                                20


<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence:  Primer

<400> SEQUENCE: 69

aacgcctgcc atcttgaac                                                 19


<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 70

gttgggcaca attcttatgc                                                20
```

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 71
gttgtttgga ggtcaggtac 20

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 72
aacatcaccc agctgttcca g 21

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 73
actcaggaga taccagggac 20

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 74
ggaagacaac aagcagtttc ac 22

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 75
atctactgcc ctgatcatac 20

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 76
aagactgaga cttcagtctt c 21

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 77
ggtgtgcctt ttaaaagtgt gc 22

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 78
ttcatgtttc cctacaaaac cc 22

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 79
catgagagtt tctcattcat gg 22

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 80
tgtttacatg gtttttaggg cc 22

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 81
ttcagcagga ggagggatg 19

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 82
cctttccttc actgatttct gc 22

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 83
aatcagcact tcgcggtg 18

<210> SEQ ID NO 84
<211> LENGTH: 19

```
<212> TYPE: DNA
<213> ORGANISM: Artificial Sequence
<220> FEATURE:
<223> OTHER INFORMATION: Description of Artificial Sequence:  Primer

<400> SEQUENCE: 84

tgtaaggcct tcccaaagc                                              19


<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 85

tggtccttca gcgcacacac                                             20


<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 86

cattttgcag agctggcagc                                             20


<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 87

cttctgtcag gagatgatcc                                             20


<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 88

ggagtgcatt atatccagac g                                           21


<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 89

cctggctctg cttgaccaac                                             20


<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 90

tgctgtcctg tgagagcatc                                             20
```

<210> SEQ ID NO 91
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 91
gtaaccctcc cagctttgg 19

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 92
cagttcccac ataaggcctg 20

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 93
cagttctgga tgccctgag 19

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 94
gaagagaggt cccatggaaa gg 22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 95
gcttgcataa gcatatcaat tg 22

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 96
ctcctaaacc atcctttgct c 21

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 97
aggcaggcac aagagctg 18

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 98
cttaccctgg ggcctgac 18

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 99
ctcagagcca ccctactata g 21

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 100
gaagcttctc cagccctagc 20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 101
tgcactctca tgaaacaggc 20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 102
gtttggggtg tttgcttgtc 20

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 103
acctctttcc ccaacccaga g 21

<210> SEQ ID NO 104
<211> LENGTH: 20

<212> TYPE: DNA
<213> ORGANISM: Artificial Sequence
<220> FEATURE:
<223> OTHER INFORMATION: Description of Artificial Sequence: Primer

<400> SEQUENCE: 104
gaagcagtaa tcagaagggc 20

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 105
gcctcacatt cttccatgct g 21

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 106
tcacatccca caggcaagag 20

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 107
ttccaagtgt caatggagaa c 21

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 108
attaccttag gcccaaccac 20

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 109
acactgggtg ttctggacc 19

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 110
gtgtagggtg gtgttttcc 19

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 111
aagcccagtg aaccagctgg 20

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 112
tcagctgagt gcccttcag 19

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 113
aggtgagcaa gtcagtttcg g 21

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 114
ggtcttcgtg tgtggtcatt 20

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 115
ggtccagttc ttccagag 18

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 116
atcctctgac tcagcaatca ca 22

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 117
ttgcaattac aaatgcaatg g 21

<210> SEQ ID NO 118
<211> LENGTH: 2261
<212> TYPE: PRT
<213> ORGANISM: Murine sp.
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (175)..(175)
<223> OTHER INFORMATION: Variable amino acid

<400> SEQUENCE: 118

```
Met Ala Cys Xaa Pro Gln Leu Arg Leu Leu Leu Trp Lys Asn Leu Thr
1               5                   10                  15

Phe Arg Arg Arg Gln Thr Cys Gln Leu Leu Leu Glu Val Ala Trp Pro
            20                  25                  30

Leu Phe Ile Phe Leu Ile Leu Ile Ser Val Arg Leu Ser Tyr Pro Pro
        35                  40                  45

Tyr Glu Gln His Glu Cys His Phe Pro Asn Lys Ala Met Pro Ser Ala
    50                  55                  60

Gly Thr Leu Pro Trp Val Gln Gly Ile Ile Cys Asn Ala Asn Asn Pro
65                  70                  75                  80

Cys Phe Arg Tyr Pro Thr Pro Gly Glu Ala Pro Gly Val Val Gly Asn
                85                  90                  95

Phe Asn Lys Ser Ile Val Ser Arg Leu Phe Ser Asp Ala Gln Arg Leu
            100                 105                 110

Leu Leu Tyr Ser Gln Arg Asp Thr Ser Ile Lys Asp Met His Lys Val
        115                 120                 125

Leu Arg Met Leu Arg Gln Ile Lys His Pro Asn Ser Asn Leu Lys Leu
    130                 135                 140

Gln Asp Phe Leu Val Asp Asn Glu Thr Phe Ser Gly Phe Leu Gln His
145                 150                 155                 160

Asn Leu Ser Leu Pro Arg Ser Thr Val Asp Ser Leu Leu Gln Xaa Asn
                165                 170                 175

Val Gly Leu Gln Lys Val Phe Leu Gln Gly Tyr Gln Leu His Leu Ala
            180                 185                 190

Ser Leu Cys Asn Gly Ser Lys Leu Glu Glu Ile Ile Gln Leu Gly Asp
        195                 200                 205

Ala Glu Val Ser Ala Leu Cys Gly Leu Pro Arg Lys Lys Leu Asp Ala
    210                 215                 220

Ala Glu Arg Val Leu Arg Tyr Asn Met Asp Ile Leu Lys Pro Val Val
225                 230                 235                 240

Thr Lys Leu Asn Ser Thr Ser His Leu Pro Thr Gln His Leu Ala Glu
                245                 250                 255

Ala Thr Thr Val Leu Leu Asp Ser Leu Gly Gly Leu Ala Gln Glu Leu
            260                 265                 270

Phe Ser Thr Lys Ser Trp Ser Asp Met Arg Gln Glu Val Met Phe Leu
        275                 280                 285

Thr Asn Val Asn Ser Ser Ser Ser Ser Thr Gln Ile Tyr Gln Ala Val
    290                 295                 300

Ser Arg Ile Val Cys Gly His Pro Glu Gly Gly Gly Leu Lys Ile Lys
305                 310                 315                 320
```

```
Ser Leu Asn Trp Tyr Glu Asp Asn Asn Tyr Lys Ala Leu Phe Gly Gly
                325                 330                 335

Asn Asn Thr Glu Glu Asp Val Asp Thr Phe Tyr Asp Asn Ser Thr Thr
            340                 345                 350

Pro Tyr Cys Asn Asp Leu Met Lys Asn Leu Glu Ser Ser Pro Leu Ser
        355                 360                 365

Arg Ile Ile Trp Lys Ala Leu Lys Pro Leu Leu Val Gly Lys Ile Leu
    370                 375                 380

Tyr Thr Pro Asp Thr Pro Ala Thr Arg Gln Val Met Ala Glu Val Asn
385                 390                 395                 400

Lys Thr Phe Gln Glu Leu Ala Val Phe His Asp Leu Glu Gly Met Trp
                405                 410                 415

Glu Glu Leu Ser Pro Gln Ile Trp Thr Phe Met Glu Asn Ser Gln Glu
            420                 425                 430

Met Asp Leu Val Arg Thr Leu Leu Asp Ser Arg Gly Asn Asp Gln Phe
        435                 440                 445

Trp Glu Gln Lys Leu Asp Gly Leu Asp Trp Thr Ala Gln Asp Ile Met
    450                 455                 460

Ala Phe Leu Ala Lys Asn Pro Glu Asp Val Gln Ser Pro Asn Gly Ser
465                 470                 475                 480

Val Tyr Thr Trp Arg Glu Ala Phe Asn Glu Thr Asn Gln Ala Ile Gln
                485                 490                 495

Thr Ile Ser Arg Phe Met Glu Cys Val Asn Leu Asn Lys Leu Glu Pro
            500                 505                 510

Ile Pro Thr Glu Val Arg Leu Ile Asn Lys Ser Met Glu Leu Leu Asp
        515                 520                 525

Glu Arg Lys Phe Trp Ala Gly Ile Val Phe Thr Gly Ile Thr Pro Asp
    530                 535                 540

Ser Val Glu Leu Pro His His Val Lys Tyr Lys Ile Arg Met Asp Ile
545                 550                 555                 560

Asp Asn Val Glu Arg Thr Asn Lys Ile Lys Asp Gly Tyr Trp Asp Pro
                565                 570                 575

Gly Pro Arg Ala Asp Pro Phe Glu Asp Met Arg Tyr Val Trp Gly Gly
            580                 585                 590

Phe Ala Tyr Leu Gln Asp Val Val Glu Gln Ala Ile Ile Arg Val Leu
        595                 600                 605

Thr Gly Ser Glu Lys Lys Thr Gly Val Tyr Val Gln Gln Met Pro Tyr
    610                 615                 620

Pro Cys Tyr Val Asp Asp Ile Phe Leu Arg Val Met Ser Arg Ser Met
625                 630                 635                 640

Pro Leu Phe Met Thr Leu Ala Trp Ile Tyr Ser Val Ala Val Ile Ile
                645                 650                 655

Lys Ser Ile Val Tyr Glu Lys Glu Ala Arg Leu Lys Glu Thr Met Arg
            660                 665                 670

Ile Met Gly Leu Asp Asn Gly Ile Leu Trp Phe Ser Trp Phe Val Ser
        675                 680                 685

Ser Leu Ile Pro Leu Leu Val Ser Ala Gly Leu Leu Val Val Ile Leu
    690                 695                 700

Lys Leu Gly Asn Leu Leu Pro Tyr Ser Asp Pro Ser Val Val Phe Val
705                 710                 715                 720

Phe Leu Ser Val Phe Ala Met Val Thr Ile Leu Gln Cys Phe Leu Ile
                725                 730                 735

Ser Thr Leu Phe Ser Arg Ala Asn Leu Ala Ala Ala Cys Gly Gly Ile
```

```
            740                 745                 750

Ile Tyr Phe Thr Leu Tyr Leu Pro Tyr Val Leu Cys Val Ala Trp Gln
        755                 760                 765

Asp Tyr Val Gly Phe Ser Ile Lys Ile Phe Ala Ser Leu Leu Ser Pro
    770                 775                 780

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
                805                 810                 815

Asp Gly Phe Asn Leu Thr Thr Ala Val Ser Met Met Leu Phe Asp Thr
            820                 825                 830

Phe Leu Tyr Gly Val Met Thr Trp Tyr Ile Glu Ala Val Phe Pro Gly
        835                 840                 845

Gln Tyr Gly Ile Pro Arg Pro Trp Tyr Phe Pro Cys Thr Lys Ser Tyr
    850                 855                 860

Trp Phe Gly Glu Glu Ile Asp Glu Lys Ser His Pro Gly Ser Ser Gln
865                 870                 875                 880

Lys Gly Val Ser Glu Ile Cys Met Glu Glu Glu Pro Thr His Leu Arg
                885                 890                 895

Leu Gly Val Ser Ile Gln Asn Leu Val Lys Val Tyr Arg Asp Gly Met
            900                 905                 910

Lys Val Ala Val Asp Gly Leu Ala Leu Asn Phe Tyr Glu Gly Gln Ile
        915                 920                 925

Thr Ser Phe Leu Gly His Asn Gly Ala Gly Lys Thr Thr Thr Met Ser
    930                 935                 940

Ile Leu Thr Gly Leu Phe Pro Pro Thr Ser Gly Thr Ala Tyr Ile Leu
945                 950                 955                 960

Gly Lys Asp Ile Arg Ser Glu Met Ser Ser Ile Arg Gln Asn Leu Gly
                965                 970                 975

Val Cys Pro Gln His Asn Val Leu Phe Asp Met Leu Thr Val Glu Glu
            980                 985                 990

His Ile Trp Phe Tyr Ala Arg Leu  Lys Gly Leu Ser Glu  Lys His Val
        995                 1000                 1005

Lys Ala  Glu Met Glu Gln Met  Ala Leu Asp Val Gly  Leu Pro Pro
    1010                 1015                 1020

Ser Lys  Leu Lys Ser Lys Thr  Ser Gln Leu Ser Gly  Gly Met Gln
    1025                 1030                 1035

Arg Lys  Leu Ser Val Ala Leu  Ala Phe Val Gly Gly  Ser Lys Val
    1040                 1045                 1050

Val Ile  Leu Asp Glu Pro Thr  Ala Gly Val Asp Pro  Tyr Ser Arg
    1055                 1060                 1065

Arg Gly  Ile Trp Glu Leu Leu  Leu Lys Tyr Arg Gln  Gly Arg Thr
    1070                 1075                 1080

Ile Ile  Leu Ser Thr His His  Met Asp Glu Ala Asp  Ile Leu Gly
    1085                 1090                 1095

Asp Arg  Ile Ala Ile Ile Ser  His Gly Lys Leu Cys  Cys Val Gly
    1100                 1105                 1110

Ser Ser  Leu Phe Leu Lys Asn  Gln Leu Gly Thr Gly  Tyr Tyr Leu
    1115                 1120                 1125

Thr Leu  Val Lys Lys Asp Val  Glu Ser Ser Leu Ser  Ser Cys Arg
    1130                 1135                 1140

Asn Ser  Ser Ser Thr Val Ser  Cys Leu Lys Lys Glu  Asp Ser Val
    1145                 1150                 1155
```

```
Ser Gln  Ser Ser Ser Asp Ala  Gly Leu Gly Ser Asp  His Glu Ser
    1160                 1165                 1170

Asp Thr  Leu Thr Ile Asp Val  Ser Ala Ile Ser Asn  Leu Ile Arg
    1175                 1180                 1185

Lys His  Val Ser Glu Ala Arg  Leu Val Glu Asp Ile  Gly His Glu
    1190                 1195                 1200

Leu Thr  Tyr Val Leu Pro Tyr  Glu Ala Ala Lys Glu  Gly Ala Phe
    1205                 1210                 1215

Val Glu  Leu Phe His Glu Ile  Asp Asp Arg Leu Ser  Asp Leu Gly
    1220                 1225                 1230

Ile Ser  Ser Tyr Gly Ile Ser  Glu Thr Thr Leu Glu  Glu Ile Phe
    1235                 1240                 1245

Leu Lys  Val Ala Glu Glu Ser  Gly Val Asp Ala Glu  Thr Ser Asp
    1250                 1255                 1260

Gly Thr  Leu Pro Ala Arg Arg  Asn Arg Arg Ala Phe  Gly Asp Lys
    1265                 1270                 1275

Gln Ser  Cys Leu His Pro Phe  Thr Glu Asp Asp Ala  Val Asp Pro
    1280                 1285                 1290

Asn Asp  Ser Asp Ile Asp Pro  Glu Ser Arg Glu Thr  Asp Leu Leu
    1295                 1300                 1305

Ser Gly  Met Asp Gly Lys Gly  Ser Tyr Gln Leu Lys  Gly Trp Lys
    1310                 1315                 1320

Leu Thr  Gln Gln Gln Phe Val  Ala Leu Leu Trp Lys  Arg Leu Leu
    1325                 1330                 1335

Ile Ala  Arg Arg Ser Arg Lys  Gly Phe Phe Ala Gln  Ile Val Leu
    1340                 1345                 1350

Pro Ala  Val Phe Val Cys Ile  Ala Leu Val Phe Ser  Leu Ile Val
    1355                 1360                 1365

Pro Pro  Phe Gly Lys Tyr Pro  Ser Leu Glu Leu Gln  Pro Trp Met
    1370                 1375                 1380

Tyr Asn  Glu Gln Tyr Thr Phe  Val Ser Asn Asp Ala  Pro Glu Asp
    1385                 1390                 1395

Met Gly  Thr Gln Glu Leu Leu  Asn Ala Leu Thr Lys  Asp Pro Gly
    1400                 1405                 1410

Phe Gly  Thr Arg Cys Met Glu  Gly Asn Pro Ile Pro  Asp Thr Pro
    1415                 1420                 1425

Cys Leu  Ala Gly Glu Glu Asp  Trp Thr Ile Ser Pro  Val Pro Gln
    1430                 1435                 1440

Ser Ile  Val Asp Leu Phe Gln  Asn Gly Asn Trp Thr  Met Lys Asn
    1445                 1450                 1455

Pro Ser  Pro Ala Cys Gln Cys  Ser Ser Asp Lys Ile  Lys Lys Met
    1460                 1465                 1470

Leu Pro  Val Cys Pro Pro Gly  Ala Gly Gly Leu Pro  Pro Pro Gln
    1475                 1480                 1485

Arg Lys  Gln Lys Thr Ala Asp  Ile Leu Gln Asn Leu  Thr Gly Arg
    1490                 1495                 1500

Asn Ile  Ser Asp Tyr Leu Val  Lys Thr Tyr Val Gln  Ile Ile Ala
    1505                 1510                 1515

Lys Ser  Leu Lys Asn Lys Ile  Trp Val Asn Glu Phe  Arg Tyr Gly
    1520                 1525                 1530

Gly Phe  Ser Leu Gly Val Ser  Asn Ser Gln Ala Leu  Pro Pro Ser
    1535                 1540                 1545

His Glu  Val Asn Asp Ala Ile  Lys Gln Met Lys Lys  Leu Leu Lys
    1550                 1555                 1560
```

```
Leu Thr  Lys Asp Thr Ser Ala  Asp Arg Phe Leu Ser  Ser Leu Gly
    1565                 1570                 1575

Arg Phe  Met Ala Gly Leu Asp  Thr Lys Asn Asn Val  Lys Val Trp
    1580                 1585                 1590

Phe Asn  Asn Lys Gly Trp His  Ala Ile Ser Ser Phe  Leu Asn Val
    1595                 1600                 1605

Ile Asn  Asn Ala Ile Leu Arg  Ala Asn Leu Gln Lys  Gly Glu Asn
    1610                 1615                 1620

Pro Ser  Gln Tyr Gly Ile Thr  Ala Phe Asn His Pro  Leu Asn Leu
    1625                 1630                 1635

Thr Lys  Gln Gln Leu Ser Glu  Val Ala Leu Met Thr  Thr Ser Val
    1640                 1645                 1650

Asp Val  Leu Val Ser Ile Cys  Val Ile Phe Ala Met  Ser Phe Val
    1655                 1660                 1665

Pro Ala  Ser Phe Val Val Phe  Leu Ile Gln Glu Arg  Val Ser Lys
    1670                 1675                 1680

Ala Lys  His Leu Gln Phe Ile  Ser Gly Val Lys Pro  Val Ile Tyr
    1685                 1690                 1695

Trp Leu  Ser Asn Phe Val Trp  Asp Met Cys Asn Tyr  Val Val Pro
    1700                 1705                 1710

Ala Thr  Leu Val Ile Ile Ile  Phe Ile Cys Phe Gln  Gln Lys Ser
    1715                 1720                 1725

Tyr Val  Ser Ser Thr Asn Leu  Pro Val Leu Ala Leu  Leu Leu Leu
    1730                 1735                 1740

Leu Tyr  Gly Trp Ser Ile Thr  Pro Leu Met Tyr Pro  Ala Ser Phe
    1745                 1750                 1755

Val Phe  Lys Ile Pro Ser Thr  Ala Tyr Val Val Leu  Thr Ser Val
    1760                 1765                 1770

Asn Leu  Phe Ile Gly Ile Asn  Gly Ser Val Ala Thr  Phe Val Leu
    1775                 1780                 1785

Glu Leu  Phe Thr Asn Asn Lys  Leu Asn Asp Ile Asn  Asp Ile Leu
    1790                 1795                 1800

Lys Ser  Val Phe Leu Ile Phe  Pro His Phe Cys Leu  Gly Arg Gly
    1805                 1810                 1815

Leu Ile  Asp Met Val Lys Asn  Gln Ala Met Ala Asp  Ala Leu Glu
    1820                 1825                 1830

Arg Phe  Gly Glu Asn Arg Phe  Val Ser Pro Leu Ser  Trp Asp Leu
    1835                 1840                 1845

Val Gly  Arg Asn Leu Phe Ala  Met Ala Val Glu Gly  Val Val Phe
    1850                 1855                 1860

Phe Leu  Ile Thr Val Leu Ile  Gln Tyr Arg Phe Phe  Ile Arg Pro
    1865                 1870                 1875

Arg Pro  Val Lys Ala Lys Leu  Pro Pro Leu Asn Asp  Glu Asp Glu
    1880                 1885                 1890

Asp Val  Arg Arg Glu Arg Gln  Arg Ile Leu Asp Gly  Gly Gly Gln
    1895                 1900                 1905

Asn Asp  Ile Leu Glu Ile Lys  Glu Leu Thr Lys Ile  Tyr Arg Arg
    1910                 1915                 1920

Lys Arg  Lys Pro Ala Val Asp  Arg Ile Cys Ile Gly  Ile Pro Pro
    1925                 1930                 1935

Gly Glu  Cys Phe Gly Leu Leu  Gly Val Asn Gly Ala  Gly Lys Ser
    1940                 1945                 1950

Thr Thr  Phe Lys Met Leu Thr  Gly Asp Thr Pro Val  Thr Arg Gly
```

```
    1955                1960                1965

Asp Ala  Phe Leu Asn Lys Asn  Ser Ile Leu Ser Asn  Ile His Glu
    1970                1975                1980

Val His  Gln Asn Met Gly Tyr  Cys Pro Gln Phe Asp  Ala Ile Thr
    1985                1990                1995

Glu Leu  Leu Thr Gly Arg Glu  His Val Glu Phe Phe  Ala Leu Leu
    2000                2005                2010

Arg Gly  Val Pro Glu Lys Glu  Val Gly Lys Phe Gly  Glu Trp Ala
    2015                2020                2025

Ile Arg  Lys Leu Gly Leu Val  Lys Tyr Gly Glu Lys  Tyr Ala Ser
    2030                2035                2040

Asn Tyr  Ser Gly Gly Asn Lys  Arg Lys Leu Ser Thr  Ala Met Ala
    2045                2050                2055

Leu Ile  Gly Gly Pro Pro Val  Val Phe Leu Asp Glu  Pro Thr Thr
    2060                2065                2070

Gly Met  Asp Pro Lys Ala Arg  Arg Phe Leu Trp Asn  Cys Ala Leu
    2075                2080                2085

Ser Ile  Val Lys Glu Gly Arg  Ser Val Val Leu Thr  Ser His Ser
    2090                2095                2100

Met Glu  Glu Cys Glu Ala Leu  Cys Thr Arg Met Ala  Ile Met Val
    2105                2110                2115

Asn Gly  Arg Phe Arg Cys Leu  Gly Ser Val Gln His  Leu Lys Asn
    2120                2125                2130

Arg Phe  Gly Asp Gly Tyr Thr  Ile Val Val Arg Ile  Ala Gly Ser
    2135                2140                2145

Asn Pro  Asp Leu Lys Pro Val  Gln Glu Phe Phe Gly  Leu Ala Phe
    2150                2155                2160

Pro Gly  Ser Val Leu Lys Glu  Lys His Arg Asn Met  Leu Gln Tyr
    2165                2170                2175

Gln Leu  Pro Ser Ser Leu Ser  Ser Leu Ala Arg Ile  Phe Ser Ile
    2180                2185                2190

Leu Ser  Gln Ser Lys Lys Arg  Leu His Ile Glu Asp  Tyr Ser Val
    2195                2200                2205

Ser Gln  Thr Thr Leu Asp Gln  Val Phe Val Asn Phe  Ala Lys Asp
    2210                2215                2220

Gln Ser  Asp Asp Asp His Leu  Lys Asp Leu Ser Leu  His Lys Asn
    2225                2230                2235

Gln Thr  Val Val Asp Val Ala  Val Leu Thr Ser Phe  Leu Gln Asp
    2240                2245                2250

Glu Lys  Val Lys Glu Ser Tyr  Val
    2255                2260
```

<210> SEQ ID NO 119
<211> LENGTH: 1472
<212> TYPE: PRT
<213> ORGANISM: Murine sp.
<220> FEATURE:
<221> NAME/KEY: MOD_RES
<222> LOCATION: (250)..(250)
<223> OTHER INFORMATION: Variable amino acid
<220> FEATURE:
<221> NAME/KEY: MOD_RES
<222> LOCATION: (640)..(640)
<223> OTHER INFORMATION: Variable amino acid
<220> FEATURE:
<221> NAME/KEY: MOD_RES
<222> LOCATION: (804)..(804)
<223> OTHER INFORMATION: Variable amino acid

<400> SEQUENCE: 119

```
Gln Ala Cys Ala Met Glu Ser Arg His Phe Glu Glu Thr Arg Gly Met
1               5                   10                  15

Glu Glu Glu Pro Thr His Leu Pro Leu Val Val Cys Val Asp Lys Leu
            20                  25                  30

Thr Lys Val Tyr Lys Asn Asp Lys Lys Leu Ala Leu Asn Lys Leu Ser
        35                  40                  45

Leu Asn Leu Tyr Glu Asn Gln Val Val Ser Phe Leu Gly His Asn Gly
    50                  55                  60

Ala Gly Lys Thr Thr Thr Met Ser Ile Leu Thr Gly Leu Phe Pro Pro
65                  70                  75                  80

Thr Ser Gly Ser Ala Thr Ile Tyr Gly His Asp Ile Arg Thr Glu Met
                85                  90                  95

Asp Glu Ile Arg Lys Asn Leu Gly Met Cys Pro Gln His Asn Val Leu
            100                 105                 110

Phe Asp Arg Leu Thr Val Glu Glu His Leu Trp Phe Tyr Ser Arg Leu
        115                 120                 125

Lys Ser Met Ala Gln Glu Glu Ile Arg Lys Glu Thr Asp Lys Met Ile
    130                 135                 140

Glu Asp Leu Glu Leu Ser Asn Lys Arg His Ser Leu Val Gln Thr Leu
145                 150                 155                 160

Ser Gly Gly Met Lys Arg Lys Leu Ser Val Ala Ile Ala Phe Val Gly
                165                 170                 175

Gly Ser Arg Ala Ile Ile Leu Asp Glu Pro Thr Ala Gly Val Asp Pro
            180                 185                 190

Tyr Ala Arg Arg Ala Ile Trp Asp Leu Ile Leu Lys Tyr Lys Pro Gly
        195                 200                 205

Arg Thr Ile Leu Leu Ser Thr His His Met Asp Glu Ala Asp Leu Leu
    210                 215                 220

Gly Asp Arg Ile Ala Ile Ile Ser His Gly Lys Leu Lys Cys Cys Gly
225                 230                 235                 240

Ser Pro Leu Phe Leu Lys Gly Ala Tyr Xaa Asp Gly Tyr Arg Leu Thr
                245                 250                 255

Leu Val Lys Gln Pro Ala Glu Pro Gly Thr Ser Gln Glu Pro Gly Leu
            260                 265                 270

Ala Ser Ser Pro Ser Gly Cys Pro Arg Leu Ser Ser Cys Ser Glu Pro
        275                 280                 285

Gln Val Ser Gln Phe Ile Arg Lys His Val Ala Ser Ser Leu Leu Val
    290                 295                 300

Ser Asp Thr Ser Thr Glu Leu Ser Tyr Ile Leu Pro Ser Glu Ala Val
305                 310                 315                 320

Lys Lys Gly Ala Phe Glu Arg Leu Phe Gln Gln Leu Glu His Ser Leu
                325                 330                 335

Asp Ala Leu His Leu Ser Ser Phe Gly Leu Met Asp Thr Thr Leu Glu
            340                 345                 350

Glu Val Phe Leu Lys Val Ser Glu Glu Asp Gln Ser Leu Glu Asn Ser
        355                 360                 365

Glu Ala Asp Val Lys Glu Ser Arg Lys Asp Val Leu Pro Gly Ala Glu
    370                 375                 380

Gly Leu Thr Ala Val Gly Gly Gln Ala Gly Asn Leu Ala Arg Cys Ser
385                 390                 395                 400

Glu Leu Ala Gln Ser Gln Ala Ser Leu Gln Ser Ala Ser Ser Val Gly
                405                 410                 415
```

```
Ser Ala Arg Gly Glu Glu Gly Thr Gly Tyr Ser Asp Gly Tyr Gly Asp
            420                 425                 430

Tyr Arg Pro Leu Phe Asp Asn Leu Gln Asp Pro Asp Asn Val Ser Leu
        435                 440                 445

Gln Glu Ala Glu Met Glu Ala Leu Ala Gln Val Gly Gln Gly Ser Arg
    450                 455                 460

Lys Leu Glu Gly Trp Trp Leu Lys Met Arg Gln Phe His Gly Leu Leu
465                 470                 475                 480

Val Lys Arg Phe His Cys Ala Arg Arg Asn Ser Lys Ala Leu Cys Ser
                485                 490                 495

Gln Ile Leu Leu Pro Ala Phe Phe Val Cys Val Ala Met Thr Val Ala
            500                 505                 510

Leu Ser Val Pro Glu Ile Gly Asp Leu Pro Pro Leu Val Leu Ser Pro
        515                 520                 525

Ser Gln Tyr His Asn Tyr Thr Gln Pro Arg Gly Asn Phe Ile Pro Tyr
    530                 535                 540

Ala Asn Glu Glu Arg Gln Glu Tyr Arg Leu Arg Leu Ser Pro Asp Ala
545                 550                 555                 560

Ser Pro Gln Gln Leu Val Ser Thr Phe Arg Leu Pro Ser Gly Val Gly
                565                 570                 575

Ala Thr Cys Val Leu Lys Ser Pro Ala Asn Gly Ser Leu Gly Pro Met
            580                 585                 590

Leu Asn Leu Ser Ser Gly Glu Ser Arg Leu Leu Ala Ala Arg Phe Phe
        595                 600                 605

Asp Ser Met Cys Leu Glu Ser Phe Thr Gln Gly Leu Pro Leu Ser Asn
    610                 615                 620

Phe Val Pro Pro Pro Pro Ser Pro Ala Pro Ser Asp Ser Pro Val Xaa
625                 630                 635                 640

Pro Asp Glu Asp Ser Leu Gln Ala Trp Asn Met Ser Leu Pro Pro Thr
                645                 650                 655

Ala Gly Pro Glu Thr Trp Thr Ser Ala Pro Ser Leu Pro Arg Leu Val
            660                 665                 670

His Glu Pro Val Arg Cys Thr Cys Ser Ala Gln Gly Thr Gly Phe Ser
        675                 680                 685

Cys Pro Ser Ser Val Gly Gly His Pro Pro Gln Met Arg Val Val Thr
    690                 695                 700

Gly Asp Ile Leu Thr Asp Ile Thr Gly His Asn Val Ser Glu Tyr Leu
705                 710                 715                 720

Leu Phe Thr Ser Asp Arg Phe Arg Leu His Arg Tyr Gly Ala Ile Thr
                725                 730                 735

Phe Gly Asn Val Gln Lys Ser Ile Pro Ala Ser Phe Gly Ala Arg Val
            740                 745                 750

Pro Pro Met Val Arg Lys Ile Ala Val Arg Arg Val Ala Gln Val Leu
        755                 760                 765

Tyr Asn Asn Lys Gly Tyr His Ser Met Pro Thr Tyr Leu Asn Ser Leu
    770                 775                 780

Asn Asn Ala Ile Leu Arg Ala Asn Leu Pro Lys Ser Lys Gly Asn Pro
785                 790                 795                 800

Ala Ala Tyr Xaa Ile Thr Val Thr Asn His Pro Met Asn Lys Thr Ser
                805                 810                 815

Ala Ser Leu Ser Leu Asp Tyr Leu Leu Gln Gly Thr Asp Val Val Ile
            820                 825                 830

Ala Ile Phe Ile Ile Val Ala Met Ser Phe Val Pro Ala Ser Phe Val
        835                 840                 845
```

```
Val Phe Leu Val Ala Glu Lys Ser Thr Lys Ala Lys His Leu Gln Phe
    850                 855                 860

Val Ser Gly Cys Asn Pro Val Ile Tyr Trp Leu Ala Asn Tyr Val Trp
865                 870                 875                 880

Asp Met Leu Asn Tyr Leu Val Pro Ala Thr Cys Cys Val Ile Ile Leu
                885                 890                 895

Phe Val Phe Asp Leu Pro Ala Tyr Thr Ser Pro Thr Asn Phe Pro Ala
            900                 905                 910

Val Leu Ser Leu Phe Leu Leu Tyr Gly Trp Ser Ile Thr Pro Ile Met
        915                 920                 925

Tyr Pro Ala Ser Phe Trp Phe Glu Val Pro Ser Ser Ala Tyr Val Phe
    930                 935                 940

Leu Ile Val Ile Asn Leu Phe Ile Gly Ile Thr Ala Thr Val Ala Thr
945                 950                 955                 960

Phe Leu Leu Gln Leu Phe Glu His Asp Lys Asp Leu Lys Val Val Asn
                965                 970                 975

Ser Tyr Leu Lys Ser Cys Phe Leu Ile Phe Pro Asn Tyr Asn Leu Gly
            980                 985                 990

His Gly Leu Met Glu Met Ala Tyr  Asn Glu Tyr Ile Asn  Glu Tyr Tyr
        995                 1000                1005

Ala Lys  Ile Gly Gln Phe Asp  Lys Met Lys Ser Pro  Phe Glu Trp
    1010                1015                1020

Asp Ile  Val Thr Arg Gly Leu  Val Ala Met Thr Val  Glu Gly Phe
    1025                1030                1035

Val Gly  Phe Phe Leu Thr Ile  Met Cys Gln Tyr Asn  Phe Leu Arg
    1040                1045                1050

Gln Pro  Gln Arg Leu Pro Val  Ser Thr Lys Pro Val  Glu Asp Asp
    1055                1060                1065

Val Asp  Val Ala Ser Glu Arg  Gln Arg Val Leu Arg  Gly Asp Ala
    1070                1075                1080

Asp Asn  Asp Met Val Lys Ile  Glu Asn Leu Thr Lys  Val Tyr Lys
    1085                1090                1095

Ser Arg  Lys Ile Gly Arg Ile  Leu Ala Val Asp Arg  Leu Cys Leu
    1100                1105                1110

Gly Val  Cys Val Pro Gly Glu  Cys Phe Gly Leu Leu  Gly Val Asn
    1115                1120                1125

Gly Ala  Gly Lys Thr Ser Thr  Phe Lys Met Leu Thr  Gly Asp Glu
    1130                1135                1140

Ser Thr  Thr Gly Gly Glu Ala  Phe Val Asn Gly His  Ser Val Leu
    1145                1150                1155

Lys Asp  Leu Leu Gln Val Gln  Gln Ser Leu Gly Tyr  Cys Pro Gln
    1160                1165                1170

Phe Asp  Val Pro Val Asp Glu  Leu Thr Ala Arg Glu  His Leu Gln
    1175                1180                1185

Leu Tyr  Thr Arg Leu Arg Cys  Ile Pro Trp Lys Asp  Glu Ala Gln
    1190                1195                1200

Val Val  Lys Trp Ala Leu Glu  Lys Leu Glu Leu Thr  Lys Tyr Ala
    1205                1210                1215

Asp Lys  Pro Ala Gly Thr Tyr  Ser Gly Gly Asn Lys  Arg Lys Leu
    1220                1225                1230

Ser Thr  Ala Ile Ala Leu Ile  Gly Tyr Pro Ala Phe  Ile Phe Leu
    1235                1240                1245

Asp Glu  Pro Thr Thr Gly Met  Asp Pro Lys Ala Arg  Arg Phe Leu
```

```
    1250                1255                1260

Trp Asn  Leu Ile Leu Asp Leu  Ile Lys Thr Gly Arg  Ser Val Val
    1265                1270                1275

Leu Thr  Ser His Ser Met Glu  Glu Cys Glu Ala Leu  Cys Thr Arg
    1280                1285                1290

Leu Ala  Ile Met Val Asn Gly  Arg Leu His Cys Leu  Gly Ser Ile
    1295                1300                1305

Gln His  Leu Lys Asn Arg Phe  Gly Asp Gly Tyr Met  Ile Thr Val
    1310                1315                1320

Arg Thr  Lys Ser Ser Gln Asn  Val Lys Asp Val Val  Arg Phe Phe
    1325                1330                1335

Asn Arg  Asn Phe Pro Glu Ala  His Ala Gln Gly Lys  Thr Pro Tyr
    1340                1345                1350

Lys Val  Gln Tyr Gln Leu Lys  Ser Glu His Ile Ser  Leu Ala Gln
    1355                1360                1365

Val Phe  Ser Lys Met Glu Gln  Val Val Gly Val Leu  Gly Ile Glu
    1370                1375                1380

Asp Tyr  Ser Val Ser Gln Thr  Thr Leu Asp Asn Val  Phe Val Asn
    1385                1390                1395

Phe Ala  Lys Lys Gln Ser Asp  Asn Val Glu Gln Gln  Glu Ala Glu
    1400                1405                1410

Pro Ser  Ser Leu Pro Ser Pro  Leu Gly Leu Leu Ser  Leu Leu Arg
    1415                1420                1425

Pro Arg  Pro Ala Pro Thr Glu  Leu Arg Ala Leu Val  Ala Asp Glu
    1430                1435                1440

Pro Glu  Asp Leu Asp Thr Glu  Asp Glu Gly Leu Ile  Ser Phe Glu
    1445                1450                1455

Glu Glu  Arg Ala Gln Leu Ser  Phe Asn Thr Asp Thr  Leu Cys
    1460                1465                1470


<210> SEQ ID NO 120
<211> LENGTH: 1704
<212> TYPE: PRT
<213> ORGANISM: Homo sapiens

<400> SEQUENCE: 120

Met Ala Val Leu Arg Gln Leu Ala Leu Leu Leu Trp Lys Asn Tyr Thr
1               5                   10                  15

Leu Gln Lys Arg Lys Val Leu Val Thr Val Leu Glu Leu Phe Leu Pro
            20                  25                  30

Leu Leu Phe Ser Gly Ile Leu Ile Trp Leu Arg Leu Lys Ile Gln Ser
        35                  40                  45

Glu Asn Val Pro Asn Ala Thr Ile Tyr Pro Gly Gln Ser Ile Gln Glu
    50                  55                  60

Leu Pro Leu Phe Phe Thr Phe Pro Pro Pro Gly Asp Thr Trp Glu Leu
65                  70                  75                  80

Ala Tyr Ile Pro Ser His Ser Asp Ala Ala Lys Thr Val Thr Glu Thr
                85                  90                  95

Val Arg Arg Ala Leu Val Ile Asn Met Arg Val Arg Gly Phe Pro Ser
            100                 105                 110

Glu Lys Asp Phe Glu Asp Tyr Ile Arg Tyr Asp Asn Cys Ser Ser Ser
        115                 120                 125

Val Leu Ala Ala Val Val Phe Glu His Pro Phe Asn His Ser Lys Glu
    130                 135                 140

Pro Leu Pro Leu Ala Val Lys Tyr His Leu Arg Phe Ser Tyr Thr Arg
```

```
145                 150                 155                 160

Arg Asn Tyr Met Trp Thr Gln Thr Gly Ser Phe Phe Leu Lys Glu Thr
                165                 170                 175

Glu Gly Trp His Thr Thr Ser Leu Phe Pro Leu Phe Pro Asn Pro Gly
            180                 185                 190

Pro Arg Glu Pro Thr Ser Pro Asp Gly Gly Glu Pro Gly Tyr Ile Arg
        195                 200                 205

Glu Gly Phe Leu Ala Val Gln His Ala Val Asp Arg Ala Ile Met Glu
    210                 215                 220

Tyr His Ala Asp Ala Ala Thr Arg Gln Leu Phe Gln Arg Leu Thr Val
225                 230                 235                 240

Thr Ile Lys Arg Phe Pro Tyr Pro Pro Phe Ile Ala Asp Pro Phe Leu
                245                 250                 255

Val Ala Ile Gln Tyr Gln Leu Pro Leu Leu Leu Leu Leu Ser Phe Thr
            260                 265                 270

Tyr Thr Ala Leu Thr Ile Ala Arg Ala Val Val Gln Glu Lys Glu Arg
        275                 280                 285

Arg Leu Lys Glu Tyr Met Arg Met Met Gly Leu Ser Ser Trp Leu His
    290                 295                 300

Trp Ser Ala Trp Phe Leu Leu Phe Phe Leu Phe Leu Leu Ile Ala Ala
305                 310                 315                 320

Ser Phe Met Thr Leu Leu Phe Cys Val Lys Val Lys Pro Asn Val Ala
                325                 330                 335

Val Leu Ser Arg Ser Asp Pro Ser Leu Val Leu Ala Phe Leu Leu Cys
            340                 345                 350

Phe Ala Ile Ser Thr Ile Ser Phe Ser Phe Met Val Ser Thr Phe Phe
        355                 360                 365

Ser Lys Ala Asn Met Ala Ala Ala Phe Gly Gly Phe Leu Tyr Phe Phe
    370                 375                 380

Thr Tyr Ile Pro Tyr Phe Phe Val Ala Pro Arg Tyr Asn Trp Met Thr
385                 390                 395                 400

Leu Ser Gln Lys Leu Cys Ser Cys Leu Leu Ser Asn Val Ala Met Ala
                405                 410                 415

Met Gly Ala Gln Leu Ile Gly Lys Phe Glu Ala Lys Gly Met Gly Ile
            420                 425                 430

Gln Trp Arg Asp Leu Leu Ser Pro Val Asn Val Asp Asp Asp Phe Cys
        435                 440                 445

Phe Gly Gln Val Leu Gly Met Leu Leu Leu Asp Ser Val Leu Tyr Gly
    450                 455                 460

Leu Val Thr Trp Tyr Met Glu Ala Val Phe Pro Gly Gln Phe Gly Val
465                 470                 475                 480

Pro Gln Pro Trp Tyr Phe Phe Ile Met Pro Ser Tyr Trp Cys Gly Lys
                485                 490                 495

Pro Arg Ala Val Ala Gly Lys Glu Glu Glu Asp Ser Asp Pro Glu Lys
            500                 505                 510

Ala Leu Arg Asn Glu Tyr Phe Glu Ala Glu Pro Glu Asp Leu Val Ala
        515                 520                 525

Gly Ile Lys Ile Lys His Leu Ser Lys Val Phe Arg Val Gly Asn Lys
    530                 535                 540

Asp Arg Ala Ala Val Arg Asp Leu Asn Leu Asn Leu Tyr Glu Gly Gln
545                 550                 555                 560

Ile Thr Val Leu Leu Gly His Asn Gly Ala Gly Lys Thr Thr Thr Leu
                565                 570                 575
```

```
Ser Met Leu Thr Gly Leu Phe Pro Pro Thr Ser Gly Arg Ala Tyr Ile
            580                 585                 590

Ser Gly Tyr Glu Ile Ser Gln Asp Met Val Gln Ile Arg Lys Ser Leu
        595                 600                 605

Gly Leu Cys Pro Gln His Asp Ile Leu Phe Asp Asn Leu Thr Val Ala
    610                 615                 620

Glu His Leu Tyr Phe Tyr Ala Gln Leu Lys Gly Leu Ser Arg Gln Lys
625                 630                 635                 640

Cys Pro Glu Glu Val Lys Gln Met Leu His Ile Ile Gly Leu Glu Asp
                645                 650                 655

Lys Trp Asn Ser Arg Ser Arg Phe Leu Ser Gly Gly Met Arg Arg Lys
            660                 665                 670

Leu Ser Ile Gly Ile Ala Leu Ile Ala Gly Ser Lys Val Leu Ile Leu
        675                 680                 685

Asp Glu Pro Thr Ser Gly Met Asp Ala Ile Ser Arg Arg Ala Ile Trp
    690                 695                 700

Asp Leu Leu Gln Arg Gln Lys Ser Asp Arg Thr Ile Val Leu Thr Thr
705                 710                 715                 720

His Phe Met Asp Glu Ala Asp Leu Leu Gly Asp Arg Ile Ala Ile Met
                725                 730                 735

Ala Lys Gly Glu Leu Gln Cys Cys Gly Ser Ser Leu Phe Leu Lys Gln
            740                 745                 750

Lys Tyr Gly Ala Gly Tyr His Met Thr Leu Val Lys Glu Pro His Cys
        755                 760                 765

Asn Pro Glu Asp Ile Ser Gln Leu Val His His His Val Pro Asn Ala
    770                 775                 780

Thr Leu Glu Ser Ser Ala Gly Ala Glu Leu Ser Phe Ile Leu Pro Arg
785                 790                 795                 800

Glu Ser Thr His Arg Phe Glu Gly Leu Phe Ala Lys Leu Glu Lys Lys
                805                 810                 815

Gln Lys Glu Leu Gly Ile Ala Ser Phe Gly Ala Ser Ile Thr Thr Met
            820                 825                 830

Glu Glu Val Phe Leu Arg Val Gly Lys Leu Val Asp Ser Ser Met Asp
        835                 840                 845

Ile Gln Ala Ile Gln Leu Pro Ala Leu Gln Tyr Gln His Glu Arg Arg
    850                 855                 860

Ala Ser Asp Trp Ala Val Asp Ser Asn Leu Cys Gly Ala Met Asp Pro
865                 870                 875                 880

Ser Asp Gly Ile Gly Ala Leu Ile Glu Glu Glu Arg Thr Ala Val Lys
                885                 890                 895

Leu Asn Thr Gly Leu Ala Leu His Cys Gln Gln Phe Trp Ala Met Phe
            900                 905                 910

Leu Lys Lys Ala Ala Tyr Ser Trp Arg Glu Trp Lys Met Val Ala Ala
        915                 920                 925

Gln Val Leu Val Pro Leu Thr Cys Val Thr Leu Ala Leu Leu Ala Ile
    930                 935                 940

Asn Tyr Ser Ser Glu Leu Phe Asp Asp Pro Met Leu Arg Leu Thr Leu
945                 950                 955                 960

Gly Glu Tyr Gly Arg Thr Val Val Pro Phe Ser Val Pro Gly Thr Ser
                965                 970                 975

Gln Leu Gly Gln Gln Leu Ser Glu His Leu Lys Asp Ala Leu Gln Ala
            980                 985                 990

Glu Gly Gln Glu Pro Arg Glu Val  Leu Gly Asp Leu Glu  Glu Phe Leu
        995                 1000                1005
```

```
Ile Phe  Arg Ala Ser Val Glu  Gly Gly Gly Phe Asn  Glu Arg Cys
    1010                 1015                 1020

Leu Val  Ala Ala Ser Phe Arg  Asp Val Gly Glu Arg  Thr Val Val
    1025                 1030                 1035

Asn Ala  Leu Phe Asn Asn Gln  Ala Tyr His Ser Pro  Ala Thr Ala
    1040                 1045                 1050

Leu Ala  Val Val Asp Asn Leu  Leu Phe Lys Leu Leu  Cys Gly Pro
    1055                 1060                 1065

His Ala  Ser Ile Val Val Ser  Asn Phe Pro Gln Pro  Arg Ser Ala
    1070                 1075                 1080

Leu Gln  Ala Ala Lys Asp Gln  Phe Asn Glu Gly Arg  Lys Gly Phe
    1085                 1090                 1095

Asp Ile  Ala Leu Asn Leu Leu  Phe Ala Met Ala Phe  Leu Ala Ser
    1100                 1105                 1110

Thr Phe  Ser Ile Leu Ala Val  Ser Glu Arg Ala Val  Gln Ala Lys
    1115                 1120                 1125

His Val  Gln Phe Val Ser Gly  Val His Val Ala Ser  Phe Trp Leu
    1130                 1135                 1140

Ser Ala  Leu Leu Trp Asp Leu  Ile Ser Phe Leu Ile  Pro Ser Leu
    1145                 1150                 1155

Leu Leu  Leu Val Val Phe Lys  Ala Phe Asp Val Arg  Ala Phe Thr
    1160                 1165                 1170

Arg Asp  Gly His Met Ala Asp  Thr Leu Leu Leu Leu  Leu Leu Tyr
    1175                 1180                 1185

Gly Trp  Ala Ile Ile Pro Leu  Met Tyr Leu Met Asn  Phe Phe Phe
    1190                 1195                 1200

Leu Gly  Ala Ala Thr Ala Tyr  Thr Arg Leu Thr Ile  Phe Asn Ile
    1205                 1210                 1215

Leu Ser  Gly Ile Ala Thr Phe  Leu Met Val Thr Ile  Met Arg Ile
    1220                 1225                 1230

Pro Ala  Val Lys Leu Glu Glu  Leu Ser Lys Thr Leu  Asp His Val
    1235                 1240                 1245

Phe Leu  Val Leu Pro Asn His  Cys Leu Gly Met Ala  Val Ser Ser
    1250                 1255                 1260

Phe Tyr  Glu Asn Tyr Glu Thr  Arg Arg Tyr Cys Thr  Ser Ser Glu
    1265                 1270                 1275

Val Ala  Ala His Tyr Cys Lys  Lys Tyr Asn Ile Gln  Tyr Gln Glu
    1280                 1285                 1290

Asn Phe  Tyr Ala Trp Ser Ala  Pro Gly Val Gly Arg  Phe Val Ala
    1295                 1300                 1305

Ser Met  Ala Ala Ser Gly Cys  Ala Tyr Leu Ile Leu  Leu Phe Leu
    1310                 1315                 1320

Ile Glu  Thr Asn Leu Leu Gln  Arg Leu Arg Gly Ile  Leu Cys Ala
    1325                 1330                 1335

Leu Arg  Arg Arg Arg Thr Leu  Thr Glu Leu Tyr Thr  Arg Met Pro
    1340                 1345                 1350

Val Leu  Pro Glu Asp Gln Asp  Val Ala Asp Glu Arg  Thr Arg Ile
    1355                 1360                 1365

Leu Ala  Pro Ser Pro Asp Ser  Leu Leu His Thr Pro  Leu Ile Ile
    1370                 1375                 1380

Lys Glu  Leu Ser Lys Val Tyr  Glu Gln Arg Val Pro  Leu Leu Ala
    1385                 1390                 1395

Val Asp  Arg Leu Ser Leu Ala  Val Gln Lys Gly Glu  Cys Phe Gly
```

-continued

```
    1400                1405                1410

Leu Leu  Gly Phe Asn Gly Ala  Gly Lys Thr Thr Thr  Phe Lys Met
    1415                1420                1425

Leu Thr  Gly Glu Glu Ser Leu  Thr Ser Gly Asp Ala  Phe Val Gly
    1430                1435                1440

Gly His  Arg Ile Ser Ser Asp  Val Gly Lys Val Arg  Gln Arg Ile
    1445                1450                1455

Gly Tyr  Cys Pro Gln Phe Asp  Ala Leu Leu Asp His  Met Thr Gly
    1460                1465                1470

Arg Glu  Met Leu Val Met Tyr  Ala Arg Leu Arg Gly  Ile Pro Glu
    1475                1480                1485

Arg His  Ile Gly Ala Cys Val  Glu Asn Thr Leu Arg  Gly Leu Leu
    1490                1495                1500

Leu Glu  Pro His Ala Asn Lys  Leu Val Arg Thr Tyr  Ser Gly Gly
    1505                1510                1515

Asn Lys  Arg Lys Leu Ser Thr  Gly Ile Ala Leu Ile  Gly Glu Pro
    1520                1525                1530

Ala Val  Ile Phe Leu Asp Glu  Pro Ser Thr Gly Met  Asp Pro Val
    1535                1540                1545

Ala Arg  Arg Leu Leu Trp Asp  Thr Val Ala Arg Ala  Arg Glu Ser
    1550                1555                1560

Gly Lys  Ala Ile Ile Ile Thr  Ser His Ser Met Glu  Glu Cys Glu
    1565                1570                1575

Ala Leu  Cys Thr Arg Leu Ala  Ile Met Val Gln Gly  Gln Phe Lys
    1580                1585                1590

Cys Leu  Gly Ser Pro Gln His  Leu Lys Ser Lys Phe  Gly Ser Gly
    1595                1600                1605

Tyr Ser  Leu Arg Ala Lys Val  Gln Ser Glu Gly Gln  Gln Glu Ala
    1610                1615                1620

Leu Glu  Glu Phe Lys Ala Phe  Val Asp Leu Thr Phe  Pro Gly Ser
    1625                1630                1635

Val Leu  Glu Asp Glu His Gln  Gly Met Val His Tyr  His Leu Pro
    1640                1645                1650

Gly Arg  Asp Leu Ser Trp Ala  Lys Val Phe Gly Ile  Leu Glu Lys
    1655                1660                1665

Ala Lys  Glu Lys Tyr Gly Val  Asp Asp Tyr Ser Val  Ser Gln Ile
    1670                1675                1680

Ser Leu  Glu Gln Val Phe Leu  Ser Phe Ala His Leu  Gln Pro Pro
    1685                1690                1695

Thr Ala  Glu Glu Gly Arg
    1700
```

METHODS OF GENE THERAPY USING NUCLEIC ACID SEQUENCES FOR ATP-BINDING CASSETTE TRANSPORTER

CROSS-REFERENCE TO RELATED APPLICATIONS

This is a continuation of U.S. application Ser. No. 10/336,219, filed Jan. 3, 2003, now U.S. Pat. No. 7,192,579, which is a divisional of Ser. No. 09/032,438, now U.S. Pat. No. 6,713,300, filed Feb. 27, 1998, which claims benefit of U.S. Provisional Application No. 60/039,388, filed Feb. 27, 1997. Each of these applications and patents is hereby incorporated by reference.

STATEMENT REGARDING FEDERALLY SPONSORED RESEARCH

This work was supported in part by research grants from the Department of Health and Human Services, grant numbers DHHS #2 T32GM07330-19 and #3 T32EY07102-0553, the National Institutes of Health, grant number M01-RR00064. The United States Government may have certain rights in this invention.

BACKGROUND OF THE INVENTION

Macular degeneration affects approximately 1.7 million individuals in the U.S. and is the most common cause of acquired visual impairment in those over the age of 65. Stargardt disease (STGD; McKusick Mendelian Inheritance (MIM) #248200) is arguably the most common hereditary recessive macular dystrophy and is characterized by juvenile to young adult onset, central visual impairment, progressive bilateral atrophy of the macular retinal pigment epithelium (RPE) and neuroepithelium, and the frequent appearance of orange-yellow flecks distributed around the macula and/or the midretinal periphery (Stargardt, 1909; Anderson et al., 1995). A clinically similar retinal disorder (Fundus Flavimaculatus, FFM, Franceschetti, 1963) often displays later age of onset and slower progression (Fishman, 1976; Noble and Carr, 1979). From linkage analysis, it has been concluded that STGD and FFM are most likely allelic autosomal recessive disorders with slightly different clinical manifestations caused by mutation(s) of a gene at chromosome 1p13-p21 (Gerber et al., 1995; Anderson et al., 1995). The STGD gene has been localized to a 4 cM region flanked by the recombinant markers D1S435 and D1S236 and a complete yeast artificial chromosome (YAC) contig of the region has been constructed (Anderson et al., 1995). Recently, the location of the STGD/FFM locus on human chromosome 1p has been refined to a 2 cM interval between polymorphic markers D1S406 and D1S236 by genetic linkage analysis in an independent set of STGD families (Hoyng et al., 1996). Autosomal dominant disorders with somewhat similar clinical phenotypes to STGD, identified in single large North American pedigrees, have been mapped to chromosome 13q34 (STGD2; MIM #153900; Zhang et al., 1994) and to chromosome 6q11-q14 (STGD3; MIM #600110; Stone et al., 1994) although these conditions are not characterized by the pathognomonic dark choroid observed by fluorescein angiography (Gass, 1987).

Members of the superfamily of mammalian ATP binding cassette (ABC) transporters are being considered as possible candidates for human disease phenotypes. The ABC superfamily includes genes whose products are transmembrane proteins involved in energy-dependent transport of a wide spectrum of substrates across membranes (Childs and Ling, 1994; Dean and Allikmets, 1995). Many disease-causing members of this superfamily result in defects in the transport of specific substrates (CFTR, Riordan et al., 1989; ALD, Mosser et al., 1993; SUR, Thomas et al., 1995; PMP70, Shimozawa et al., 1992; TAP2, de la Salle et al., 1994). In eukaryotes, ABC genes encode typically four domains that include two conserved ATP-binding domains (ATP) and two domains with multiple transmembrane (TM) segments (Hyde et al., 1990). The ATP-binding domains of ABC genes contain motifs of characteristic conserved residues (Walker A and B motifs) spaced by 90-120 amino acids. Both this conserved spacing and the "Signature" or "C" motif just upstream of the Walker B site distinguish members of the ABC superfamily from other ATP-binding proteins (Hyde et al., 1990; Michaelis and Berkower, 1995). These features have allowed the isolation of new ABC genes by hybridization, degenerate PCR, and inspection of DNA sequence databases (Allikmets et al., 1993, 1995; Dean et al., 1994; Luciani et al., 1994).

The characterization of twenty-one new members of the ABC superfamily may permit characterization and functions assigned to these genes by determining their map locations and their patterns of expression (Allikmets et al., 1996). That many known ABC genes are involved in inherited human diseases suggests that some of these new loci will also encode proteins mutated in specific genetic disorders. Despite regionally localizing a gene by mapping, the determination of the precise localization and sequence of one gene nonetheless requires choosing the certain gene from about 250 genes, four to about five million base pairs, from within the regionally localized chromosomal site.

While advancements have been made as described above, mutations in retina-specific ABC transporter (ABCR) in patients with recessive macular dystrophy STGD/FFM have not yet been identified to Applicants' knowledge. That ABCR expression is limited to photoreceptors, as determined by the present invention, provides evidence as to why ABCR has not yet been sequenced. Further, the ABC1 subfamily of ABC transporters is not represented by any homolog in yeast (Michaelis and Berkower, 1995), suggesting that these genes evolved to perform specialized functions in multicellular organisms, which also lends support to why the ABCR gene has been difficult to identify. Unlike ABC genes in bacteria, the homologous genes in higher eukaryotes are much less well studied. The fact that prokaryotes contain a large number of ABC genes suggests that many mammalian members of the superfamily remain uncharacterized. The task of studying eukaryote ABC genes is more difficult because of the significantly higher complexity of eukaryotic systems and the apparent difference in function of even highly homologous genes. While ABC proteins are the principal transporters of a number of diverse compounds in bacterial cells, in contrast, eukaryotes have evolved other mechanisms for the transport of many amino acids and sugars. Eukaryotes have other reasons to diversify the role of ABC genes, for example, performing such functions as ion transport, toxin elimination, and secretion of signaling molecules.

Accordingly, there remains a need for the identification of the sequence of the gene, which in mutated forms is associated with retinal and/or macular degenerative diseases, including Stargardt Disease and Fundus Flavimaculatus, for example, in order to provide enhanced diagnoses and improved prognoses and interventional therapies for individuals affected with such diseases.

SUMMARY OF THE INVENTION

The present invention provides sequences encoding an ATP binding cassette transporter. Nucleic acid sequences, including SEQ ID NO: 1 which is a genomic sequence, and SEQ ID NOS: 2 and 5 which are cDNA sequences, are sequences to which the present invention is directed.

A further aspect of the present invention provides ATP binding cassette transporter polypeptides and/or proteins. SEQ ID NOS: 3 and 6 are novel polypeptides of the invention produced from nucleotide sequences encoding the ATP binding cassette transporter. Also within the scope of the present invention is a purified ATP binding cassette transporter.

The present invention also provides an expression vector comprising a nucleic acid sequence encoding an ATP binding cassette transporter, a transformed host cell capable of expressing a nucleic acid sequence encoding an ATP binding cassette transporter, a cell culture capable of expressing an ATP binding cassette transporter, and a protein preparation comprising an ATP binding cassette transporter.

The present invention is also directed to a method of screening for an agent that modifies ATP binding cassette transporter comprising combining purified ATP binding cassette transporter with an agent suspected of modifying ATP binding cassette transporter and observing a change in at least one characteristic associated with ATP binding cassette transporter. The present invention provides methods of identifying an agent that inhibits macular degeneration comprising combining purified ATP binding cassette transporter from a patient suspected of having macular degeneration and an agent suspected interacting with the ATP binding cassette transporter and observing an inhibition in at least one of the characteristics of diseases associated with the ATP binding cassette transporter. In addition, the present invention provides for methods of identifying an agent that induces onset of at least one characteristic associated with ATP binding cassette transporter comprising combining purified wild-type ATP binding cassette transporter with an agent suspected of inducing a macular degenerative disease and observing the onset of a characteristic associated with macular degeneration.

BRIEF DESCRIPTION OF THE DRAWINGS

FIG. 1A displays a physical map of the ABCR gene. Mega-YAC clones from the CEPH mega-YAC genomic library (Bellane-Chantelot et al., 1992) encompassing the 4 cM critical region for STGD are represented by horizontal bars with shaded circles indicating confirmed positives for STSs by landmark mapping. The individual STS markers and their physical order are shown below the YACs with arrows indicating the centromeric (cen) and telomeric (1 pter) direction (Anderson et al., 1995). The horizontal double head arrow labeled STGD indicates the refined genetic interval delineated by historical recombinants (Anderson et al., 1995). FIG. 1B displays the results of agarose gel electrophoresis of PCR amplification products with primers from the 5' (GGTCTTCGTGTGTGGTCATT, SEQ ID NO: 114, GGTCCAGTTCTTCCAGAG, SEQ ID NO: 115, labeled 5' ABCR) or 3' (ATCCTCTGACTCAGCAATCACA, SEQ ID NO:116, TTGCAATTACAAATGCAATGG, SEQ ID NO: 117, labeled 3' ABCR) regions of ABCR on the 13 different YAC DNA templates indicated as diagonals above the gel. The asterisk denotes that YAC 680_b__5 was positive for the 5' ABCR PCR but negative for the 3' ABCR PCR. These data suggest the ABCR gene maps within the interval delineated by markers D1S3361-D1S236 and is transcribed toward the telomere, as depicted by the open horizontal box.

FIG. 2 exhibits the size and tissue distribution of ABCR transcripts in the adult rat. A blot of total RNA from the indicated tissues was hybridized with a 1.6 kb mouse Abcr probe (top) and a ribosomal protein S26 probe (bottom; Kuwano et al., 1985). The ABCR probe revealed a predominant transcript of approximately 8 kb that is found in retina only. The mobility of the 28S and 18S ribosomal RNAs are indicated at the right. B, brain; H, heart; K, kidney; Li, liver; Lu, lung; R, retina; S, spleen.

FIGS. 3A-H show the sequence of the ABCR coding region within the genomic ABCR sequence, SEQ ID NO: 1. The sequence of the ABCR cDNA, SEQ ID NO: 2, is shown with the predicted protein sequence, SEQ ID NO: 3, in one-letter amino acid code below. The location of splice sites is shown by the symbol |.

FIGS. 4A-D display the alignment of the ABCR protein, SEQ ID NO:3, with other members of the ABC1 subfamily. The deduced amino acid sequence of ABCR is shown aligned to known human and mouse proteins that are members of the same subfamily. Mouse Abc1 (SEQ ID NO:118); Abc2; mouse Abc2 (SEQ ID NO:119); and ABCC, human ABC gene (SEQ ID NO: 120). The Walker A and B motifs and the Signature C motif are designated by underlining and the letters A, B, and C, respectively.

FIGS. 7A-D display hybridization results of retina and choroid from a pigmented mouse (C57/B16); FIGS. 7E and 7F show hybridization results of retina and choroid from an albino rat; and FIGS. 7G and 7H exhibit hybridization results of retina from a macaque monkey. FIGS. 7A, 7E, and 7G display results from a mouse abcr antisense probe; FIG. 7B exhibits results from a mouse abcr sense probe; FIG. 7C shows results from a macaque rhodopsin antisense probe; and FIGS. 7D, 7F, and 7H display results from a mouse blue cone pigment antisense probe. ABCR transcripts are localized to the inner segments of the photoreceptor cell layer, a pattern that matches the distribution of rhodopsin transcripts but is distinct from the distribution of cone visual pigment transcripts. Hybridization is not observed in the RPE or choroid, as seen most clearly in the albino rat eye (arrowhead in FIG. 7E). The retinal layers indicated in FIG. 7B are: OS, outer segments; IS, inner segments; ONL, outer nuclear layer; OPL, outer plexiform layer; INL, inner nuclear layer; IPL, inner plexiform layer; GCL, ganglion cell layer.

DETAILED DESCRIPTION OF ILLUSTRATIVE EMBODIMENTS

Figure 1A:
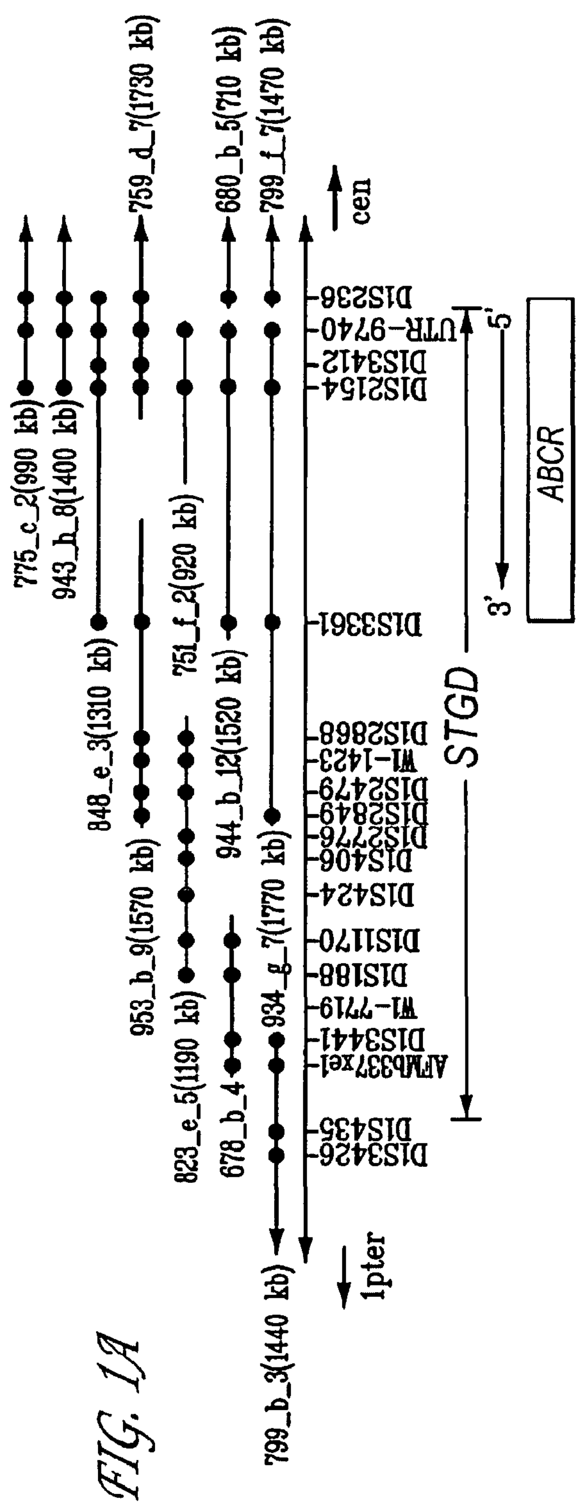
FIGS. 1A and 1B display the ABCR gene and amplification products.

The present invention is directed to the nucleic acid and protein sequences encoding ATP binding cassette transporter. The ATP binding cassette transporter of the present invention is retina specific ATP binding cassette transporter (ABCR);

more particularly, ABCR may be isolated from retinal cells, preferably photoreceptor cells. The present invention provides nucleotide sequences of ABCR including genomic sequences, SEQ ID NO: 1, and cDNA sequences SEQ ID NO: 2 and 5. Novel polypeptide sequences, SEQ ID NOS: 3 and 6, for ABCR, and the translated products of SEQ ID NOS: 2 and 5, respectively, and are also included in the present invention.

SEQ ID NO: 1 provides the human genomic DNA sequence of ABCR. SEQ ID NOS: 2 and 5 provide wild-type cDNA sequences of human ABCR, which result in translated products SEQ ID NOS: 3 and 6, respectively. While not intending to be bound by any particular theory or theories of operation, it is believed that SEQ ID NOS: 2 and 5 are isoforms of ABCR cDNA. The difference between SEQ ID NOS: 2 and 5 may be accounted for by an additional sequence in SEQ ID NO: 2 which is added between bases 4352 and 4353 of SEQ ID NO: 5. This difference is thought to arise from alternative splicing of the nascent transcript of ABCR, in which an alternative exon 30, SEQ ID NO: 4, is excluded. This alternative exon encodes an additional 38 amino acids, SEQ ID NO: 11.

Nucleic acids within the scope of the present invention include cDNA, RNA, genomic DNA, fragments or portions within the sequences, antisense oligonucleotides. Sequences encoding the ABCR also include amino acid, polypeptide, and protein sequences. Variations in the nucleic acid and polypeptide sequences of the present invention are within the scope of the present invention and include N terminal and C terminal extensions, transcription and translation modifications, and modifications in the cDNA sequence to facilitate and improve transcription and translation efficiency. In addition, changes within the wild-type sequences identified herein which changed sequence retains substantially the same wild-type activity, such that the changed sequences are substantially similar to the ABCR sequences identified, are also considered within the scope of the present invention. Mismatches, insertions, and deletions which permit substantial similarity to the ABCR sequences, such as similarity in residues in hydrophobicity, hydrophilicity, basicity, and acidity, will be known to those of skill in the art once armed with the present disclosure. In addition, the isolated, or purified, sequences of the present invention may be natural, recombinant, synthetic, or a combination thereof. Wild-type activity associated with the ABCR sequences of the present invention include, inter alia, all or part of a sequence, or a sequence substantially similar thereto, that codes for ATP binding cassette transporter.

The genomic, SEQ ID NO: 1, and cDNA, SEQ ID NOS: 2 and 5, sequences are identified in FIG. 3 and encode ABCR, certain mutations of which are responsible for the class of retinal disorders known as retinal or macular degenerations. Macular degeneration is characterized by macular dystrophy, various alterations of the peripheral retina, central visual impairment, progressive bilateral atrophy of the macular retinal pigment epithelium (RPE) and neuroepithelium, frequent appearance of orange-yellow flecks distributed around the macula and/or the midretinal periphery, and subretinal deposition of lipofuscin-like material. Retinal and macular degenerative diseases include and are not limited to Stargardt Disease, Fundus Flavimaculatus, age-related macular degeneration, and may include disorders variously called retinitis pigmentosa, combined rod and cone dystrophies, cone dystrophies and degenerations, pattern dystrophy, bull's eye maculopathies, and various other retinal degenerative disorders, some induced by drugs, toxins, environmental influences, and the like. Stargardt Disease is an autosomal recessive retinal disorder characterized by juvenile to adult-onset macular and retinal dystrophy. Fundus Flavimaculatus often displays later age of onset and slower progression. Some environmental insults and drug toxicities may create similar retinal degenerations. Linkage analysis reveals that Stargardt Disease and Fundus Flavimaculatus may be allelic autosomal recessive disorders with slightly different clinical manifestations. The identification of the ABCR gene suggests that different mutations within ABCR may be responsible for these clinical phenomena.

The present invention is also directed to a method of screening for an agent that modifies ATP binding cassette transporter comprising combining purified ATP binding cassette transporter with an agent of modifying ATP binding cassette transporter and observing a change in at least one characteristic associated with ATP binding cassette transporter.

"Modify" and variations thereof include changes such as and not limited to inhibit, suppress, delay, retard, slow, suspend, obstruct, and restrict, as well as induce, encourage, provoke, and cause. Modified may also be defined as complete inhibition such that macular degeneration is arrested, stopped, or blocked. Modifications may, directly or indirectly, inhibit or substantially inhibit, macular degeneration or induce, or substantially induce, macular degeneration, under certain circumstances.

Methods of identifying an agent that inhibits macular degeneration are embodied by the present invention and comprise combining purified ATP binding cassette transporter from a patient suspected of having macular degeneration and an agent suspected of interacting with the ATP binding cassette transporter and observing an inhibition in at least one of the characteristics of diseases associated with the ATP binding cassette transporter. Accordingly, such methods serve to reduce or prevent macular degeneration, such as in human patients. In addition, the present invention provides for methods of identifying an agent that induces onset of at least one characteristic associated with ATP binding cassette transporter comprising combining purified wild-type ATP binding cassette transporter with an agent suspected of inducing a macular degenerative disease and observing the onset of a characteristic associated with macular degenerative. Thus, such methods provide methods of using laboratory animals to determine causative agents of macular degeneration. The ATP binding cassette transporter may be provided for in the methods identified herein in the form of nucleic acids, such as and not limited to SEQ ID NOS: 1, 2, and 5 or as an amino acid, SEQ ID NOS: 3 and 6, for example. Accordingly, transcription and translation inhibitors may be separately identified. Characteristics associated with macular degeneration include and are not limited to central visual impairment, progressive bilateral atrophy of the macular retinal pigment epithelium (RPE) and neuroepithelium, and the frequent appearance of orange-yellow flecks distributed around the macula and/or the midretinal periphery. Accordingly, observing one or more of the characteristics set forth above results in identification of an agent that induces macular degeneration, whereas reduction or inhibition of at least one of the characteristics results in identification of an agent that inhibits macular degeneration.

Mutational analysis of ABCR in Stargardt Disease families revealed thus far seventy four mutations including fifty four single amino acid substitutions, five nonsense mutations resulting in early truncation of the protein, six frame shift mutations resulting in early truncation of the protein, three in-frame deletions resulting in loss of amino acid residues from the protein, and six splice site mutations resulting in incorrect processing of the nascent RNA transcript, see Table 2. Compound heterozygotes for mutations in ABCR were found in forty two families. Homozygous mutations were identified in three families with consanguineous parentage. Accordingly, mutations in wild-type ABCR which result in activities that are not associated with wild-type ABCR are herein referred to as sequences which are associated with macular degeneration. Such mutations include missense mutations, deletions, insertions, substantial differences in hydrophobicity, hydrophilicity, acidity, and basicity. Characteristics which are associated with retinal or macular degeneration include and are not limited to those characteristics set forth above.

Mutations in wild-type ABCR provide a method of detecting macular degeneration. Retinal or macular degeneration may be detected by obtaining a sample comprising patient nucleic acids from a patient tissue sample; amplifying retina-specific ATP binding cassette receptor specific nucleic acids from the patient nucleic acids to produce a test fragment; obtaining a sample comprising control nucleic acids from a control-tissue sample; amplifying control nucleic acids encoding wild-type retina-specific ATP binding cassette receptor to produce a control fragment; comparing the test fragment with the control fragment to detect the presence of a sequence difference in the test fragment, wherein a difference in the test fragment indicates macular degeneration. Mutations in the test fragment, including and not limited to each of the mutations identified above, may provide evidence of macular degeneration.

A purified ABCR protein is also provided by the present invention. The purified ABCR protein may have an amino acid sequence as provided by SEQ ID NOS: 3 and 6.

The present invention is directed to ABCR sequences obtained from mammals from the Order Rodentia, including and not limited to hamsters, rats, and mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

Generally, the sequences of the invention may be produced in host cells transformed with an expression vector comprising a nucleic acid sequence encoding ABCR. The transformed cells are cultured under conditions whereby the nucleic acid sequence coding for ABCR is expressed. After a suitable amount of time for the protein to accumulate, the protein may be purified from the transformed cells.

A gene coding for ABCR may be obtained from cDNA library. Suitable libraries can be obtained from commercial sources such as Clontech, Palo Alto, Calif. Libraries may also be prepared using the following non-limiting examples: hamster insulin-secreting tumor (HIT), mouse αTC-6, and rat insulinoma (RIN) cells. Positive clones are then subjected to DNA sequencing to determine the presence of a DNA sequence coding for ABCR. DNA sequencing is accomplished using the chain termination method of Sanger et al., *Proc. Nat'l. Acad. Sci. U.S.A.,* 1977, 74, 5463. The DNA sequence encoding ABCR is then inserted into an expression vector for later expression in a host cell.

Expression vectors and host cells are selected to form an expression system capable of synthesizing ABCR. Vectors including and not limited to baculovirus vectors may be used in the present invention. Host cells suitable for use in the invention include prokaryotic and eukaryotic cells that can be transformed to stably contain and express ABCR. For example, nucleic acids coding for the recombinant protein may be expressed in prokaryotic or eukaryotic host cells, including the most commonly used bacterial host cell for the production of recombinant proteins, *E. coli*. Other microbial strains may also be used, however, such as *Bacillus subtilis*, and other enterobacteriaceae such as *Salmonella typhimurium* or *Serratia marcescens*, various species of *Pseudomonas*, or other bacterial strains.

The preferable eukaryotic system is yeast, such as *Saccharomyces cerevisiae*. Yeast artificial chromosome (YAC) systems are able to accommodate the large size of ABCR gene sequence or genomic clone. The principle of the YAC system is similar to that used in conventional cloning of DNA. Large fragments of cDNA are ligated into two "arms" of a YAC vector, and the ligation mixture is then introduced into the yeast by transformation. Each of the arms of the YAC vector carries a selectable marker as well as appropriately oriented sequences that function as telomeres in yeast. In addition, one of the two arms carries two small fragments that function as a centromere and as an origin of replication (also called an ARS element-autonomously replicating sequences). Yeast transformants that have taken up and stably maintained an artificial chromosome are identified as colonies on agar plates containing the components necessary for selection of one or both YAC arms. YAC vectors are designed to allow rapid identification of transformants that carry inserts of genomic DNA. Insertion of genomic DNA into the cloning site interrupts a suppressor tRNA gene and results in the formation of red rather than white colonies by yeast strains that carry an amber ade2 gene.

To clone in YAC vectors, genomic DNA from the test organism is prepared under conditions that result in relatively little shearing such that its average size is several million base pairs. The cDNA is then ligated to the arms of the YAC vector, which has been appropriately prepared to prevent self-ligation. As an alternative to partial digestion with EcoRI, YAC vectors may be used that will accept genomic DNA that has been digested to completion with rarely cutting restriction enzymes such as NotI or MluI.

In addition, insect cells, such as *Spodoptera frugiperda*; chicken cells, such as E3C/O and SL-29; mammalian cells, such as HeLa, Chinese hamster ovary cells (CHO), COS-7 or MDCK cells and the like may also be used. The foregoing list is illustrative only and is not intended in any way to limit the types of host cells suitable for expression of the nucleic acid sequences of the invention.

As used herein, expression vectors refer to any type of vector that can be manipulated to contain a nucleic acid sequence coding for ABCR, such as plasmid expression vectors, viral vectors, and yeast expression vectors. The selection of the expression vector is based on compatibility with the desired host cell such that expression of the nucleic acid encoding ABCR results. Plasmid expression vectors comprise a nucleic acid sequence of the invention operably linked with at least one expression control element such as a promoter. In general, plasmid vectors contain replicon and control sequences derived from species compatible with the host cell. To facilitate selection of plasmids containing nucleic acid sequences of the invention, plasmid vectors may also contain a selectable marker such as a gene coding for antibiotic resistance. Suitable examples include the genes coding for ampicillin, tetracycline, chloramphenicol, or kanamycin resistance.

Suitable expression vectors, promoters, enhancers, and other expression control elements are known in the art and may be found in Sambrook et al., *Molecular Cloning: A Laboratory Manual*, second edition, Cold Spring Harbor Laboratory Press, Cold Spring Harbor, N.Y. (1989), incorporated herein by reference in its entirety.

Transformed host cells containing a DNA sequence encoding ABCR may then be grown in an appropriate medium for the host. The cells are then grown until product accumulation reaches desired levels at which time the cells are then harvested and the protein product purified in accordance with conventional techniques. Suitable purification methods include, but are not limited to, SDS PAGE electrophoresis, phenylboronate-agarose, reactive green 19-agarose, concanavalin A sepharose, ion exchange chromatography, affinity chromatography, electrophoresis, dialysis and other methods of purification known in the art.

Protein preparations, of purified or unpurified ABCR by host cells, are accordingly produced which comprise ABCR and other material such as host cell components and/or cell medium, depending on the degree of purification of the protein.

The invention also includes a transgenic non-human animal, including and not limited to mammals, such as and not limited to a mouse, rat, or hamster, comprising a sequence encoding ABCR, or fragment thereof that substantially retains ABCR activity, introduced into the animal or an ancestor of the animal. The sequence may be wild-type or mutant and may be introduced into the animal at the embryonic or adult stage. The sequence is incorporated into the genome of an animal such that it is chromosomally incorporated into an activated state. A transgenic non-human animal has germ cells and somatic cells that contain an ABCR sequence. Embryo cells may be transfected with the gene as it occurs naturally, and transgenic animals are selected in which the gene has integrated into the chromosome at a locus which results in activation. Other activation methods include modifying the gene or its control sequences prior to introduction into the embryo. The embryo may be transfected using a vector containing the gene.

In addition, a transgenic non-human animal may be engineered wherein ABCR is suppressed. For purposes of the present invention, suppression of ABCR includes, and is not limited to strategies which cause ABCR not to be expressed. Such strategies may include and are not limited to inhibition of protein synthesis, pre-mRNA processing, or DNA replication. Each of the above strategies may be accomplished by antisense inhibition of ABCR gene expression. Many techniques for transferring antisense sequences into cells are known to those of skill, including and not limited to microinjection, viral-mediated transfer, somatic cell transformation, transgene integration, and the like, as set forth in Pinkert, Carl, *Transgenic Animal Technology,* 1994, Academic Press, Inc., San Diego, Calif., incorporated herein by reference in its entirety.

Further, a transgenic non-human animal may be prepared such that ABCR is knocked out. For purposes of the present invention, a knock-out includes and is not limited to disruption or rendering null the ABCR gene. A knock-out may be accomplished, for example, with antisense sequences for ABCR. The ABCR gene may be knocked out by injection of an antisense sequence for all or part of the ABCR sequence such as an antisense sequence for all or part of SEQ ID NO: 2. Once ABCR has been rendered null, correlation of the ABCR to macular degeneration may be tested. Sequences encoding mutations affecting the ABCR may be inserted to test for alterations in various retinal and macular degenerations exhibited by changes in the characteristics associated with retinal and macular degeneration.

An ABCR knock-out may be engineered by inserting synthetic DNA into the animal chromosome by homologous recombination. In this method, sequences flanking the target and insert DNA are identical, allowing strand exchange and crossing over to occur between the target and insert DNA. Sequences to be inserted typically include a gene for a selectable marker, such as drug resistance. Sequences to be targeted are typically coding regions of the genome, in this case part of the ABCR gene. In this process of homologous recombination, targeted sequences are replaced with insert sequences thus disrupting the targeted gene and rendering it nonfunctional. This nonfunctional gene is called a null allele of the gene.

To create the knockout mouse, a DNA construct containing the insert DNA and flanking sequences is made. This DNA construct is transfected into pluripotent embryonic stem cells competent for recombination. The identical flanking sequences align with one another, and chromosomal recombination occurs in which the targeted sequence is replaced with the insert sequence, as described in Bradley, A., Production and Analysis of Chimeric Mice, in *Tetracarcinomas and Embryonic Stem Cells—A Practical Approach,* 1987, E. Roberson, Editor, IRC Press, pages 113-151. The stem cells are injected into an embryo, which is then implanted into a female animal and allowed to be born. The animals may contain germ cells derived from the injected stem cells, and subsequent matings may produce animals heterozygous and homozygous for the disrupted gene.

Transgenic non-human animals may also be useful for testing nucleic acid changes to identify additional mutations responsible for macular degeneration. A transgenic non-human animal may comprise a recombinant ABCR.

The present invention is also directed to gene therapy. For purposes of the present invention, gene therapy refers to the transfer and stable insertion of new genetic information into cells for the therapeutic treatment of diseases or disorders. A foreign sequence or gene is transferred into a cell that proliferates to spread the new sequence or gene throughout the cell population. Sequences include antisense sequence of all or part of ABCR, such as an antisense sequence to all or part of the sequences identified as SEQ ID NO: 1, 2, and 5. Known methods of gene transfer include microinjection, electroporation, liposomes, chromosome transfer, transfection techniques, calcium-precipitation transfection techniques, and the like. In the instant case, macular degeneration may result from a loss of gene function, as a result of a mutation for example, or a gain of gene function, as a result of an extra copy of a gene, such as three copies of a wild-type gene, or a gene over expressed as a result of a mutation in a promoter, for example. Expression may be altered by activating or deactivating regulatory elements, such as a promoter. A mutation may be corrected by replacing the mutated sequence with a wild-type sequence or inserting an antisense sequence to bind to an over expressed sequence or to a regulatory sequence.

Numerous techniques are known in the art for the introduction of foreign genes into cells and may be used to construct the recombinant cells for purposes of gene therapy, in accordance with this embodiment of the invention. The technique used should provide for the stable transfer of the heterologous gene sequence to the stem cell, so that the heterologous gene sequence is heritable and expressible by stem cell progeny, and so that the necessary development and physiological functions of the recipient cells are not disrupted. Techniques which may be used include but are not limited to chromosome transfer (e.g., cell fusion, chromosome-mediated gene transfer, micro cell-mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, M. J., 1985, Pharmac. Ther. 29:69-92, incorporated herein by reference in its entirety).

The term "purified", when used to describe the state of nucleic acid sequences of the invention, refers to nucleic acid sequences substantially free of nucleic acid not coding for ABCR or other materials normally associated with nucleic acid in non-recombinant cells, i.e., in its "native state."

The term "purified" or "in purified form" when used to describe the state of an ABCR nucleic acid, protein, polypeptide, or amino acid sequence, refers to sequences substantially free, to at least some degree, of cellular material or other material normally associated with it in its native state. Preferably the sequence has a purity (homogeneity) of at least about 25% to about 100%. More preferably the purity is at least about 50%, when purified in accordance with standard techniques known in the art.

In accordance with methods of the present invention, methods of detecting retinal or macular degenerations in a patient are provided comprising obtaining a patient tissue sample for testing. The tissue sample may be solid or liquid, a body fluid sample such as and not limited to blood, skin, serum, saliva, sputum, mucus, bone narrow, urine, lymph, and a tear; and feces. In addition, a tissue sample from amniotic fluid or chorion may be provided for the detection of retinal or macular degeneration in utero in accordance with the present invention.

A test fragment is defined herein as an amplified sample comprising ABCR-specific nucleic acids from a patient suspected of having retinal or macular degeneration. A control fragment is an amplified sample comprising normal or wild-type ABCR-specific nucleic acids from an individual not suspected of having retinal or macular degeneration.

The method of amplifying nucleic acids may be the polymerase chain reaction using a pair of primers wherein at least one primer within the pair is selected from the group consisting of SEQ ID NOS: 12-113. When the polymerase chain reaction is the amplification method of choice, a pair of primers may be used such that one primer of the pair is selected from the group consisting of SEQ ID NOS: 12-113.

Nucleic acids, such as DNA (such as and not limited to, genomic DNA and cDNA) and/or RNA (such as, and not limited to, mRNA), are obtained from the patient sample. Preferably RNA is obtained.

Nucleic acid extraction is followed by amplification of the same by any technique known in the art. The amplification step includes the use of at least one primer sequence which is complementary to a portion of ABCR-specific expressed nucleic acids or sequences on flanking intronic genomic sequences in order to amplify exon or coding sequences. Primer sequences useful in the amplification methods include and are not limited to SEQ ID NOS: 12-113, which may be used in the amplification methods. Any primer sequence of about 10 nucleotides to about 35 nucleotides, more preferably about 15 nucleotides to about 30 nucleotides, even more preferably about 17 nucleotides to about 25 nucleotides may be useful in the amplification step of the methods of the present invention. In addition, mismatches within the sequences identified above, which achieve the methods of the invention, such that the mismatched sequences are substantially complementary and thus hybridizable to the sequence sought to be identified, are also considered within the scope of the disclosure. Mismatches which permit substantial similarity to SEQ ID NOS: 12-113, such as and not limited to sequences with similar hydrophobicity, hydrophilicity, basicity, and acidity, will be known to those of skill in the art once armed with the present disclosure. The primers may also be unmodified or modified. Primers may be prepared by any method known in the art such as by standard phosphoramidite chemistry. See Sambrook et al., supra.

The method of amplifying nucleic acids may be the polymerase chain reaction using a pair of primers wherein at least one primer within the pair is selected from the group consisting of SEQ ID NOS: 12-113. When the polymerase chain reaction is the amplification method of choice, a pair of primers may be used such that one primer of the pair is selected from the group consisting of SEQ ID NOS: 12-113.

When an amplification method includes the use of two primers, a first primer and a second primer, such as in the polymerase chain reaction, one of the first primer or second primer may be selected from the group consisting of SEQ ID NOS: 12-113. Any primer pairs which copy and amplify nucleic acids between the pairs pointed toward each other and which are specific for ABCR may be used in accordance with the methods of the present invention.

A number of template dependent processes are available to amplify the target sequences of interest present in a sample. One of the best known amplification methods is the polymerase chain reaction (PCR) which is described in detail in U.S. Pat. Nos. 4,683,195, 4,683,202 and 4,800,159, and in Innis et al., *PCR Protocols*, Academic Press, Inc., San Diego Calif., 1990, each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Alternatively, a reverse transcriptase PCR amplification procedure may be performed in order to quantify the amount of mRNA amplified. Polymerase chain reaction methodologies are well known in the art.

Another method for amplification is the ligase chain reaction (referred to as LCR), disclosed in EPA No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Application No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio]triphosphates in one strand of a restriction site (Walker, G. T., et al., *Proc. Natl. Acad, Sci.* (U.S.A.) 1992, 89:392-396, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and which involves annealing several probes throughout a region targeted for amplification, followed by a repair reaction in which only two of the four bases are present. The other two bases can be added as biotinylated derivatives for easy detection. A similar approach is used in SDA.

ABCR-specific nucleic acids can also be detected using a cyclic probe reaction (CPR). In CPR, a probe having a 3' and 5' sequences of non-ABCR specific DNA and middle sequence of ABCR specific RNA is hybridized to DNA which is present in a sample. Upon hybridization, the reaction is treated with RNaseH, and the products of the probe identified as distinctive products, generate a signal which is released after digestion. The original template is annealed to another cycling probe and the reaction is repeated. Thus, CPR involves amplifying a signal generated by hybridization of a probe to a ABCR-specific expressed nucleic acid.

Still other amplification methods described in GB Application No. 2 202 328, and in PCT Application No. PCT/US89/01025, each of which is incorporated by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh D., et al., *Proc. Natl. Acad. Sci.* (U.S.A.) 1989, 86:1173, Gingeras T. R., et al., PCT Application WO 88/10315, each of which is incorporated herein by reference in its entirety), including nucleic acid sequence based amplification (NASBA) and 3SR. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has ABCR-specific sequences. Following polymerization, DNA/RNA hybrids are digested with RNase H while double standard DNA molecules are heat denatured again. In either case the single stranded DNA is made fully double stranded by addition of second ABCR-specific primer, followed by polymerization. The double standard DNA molecules are then multiply transcribed by a polymerase such as T7 or SP6. In an isothermal cyclic reaction, the RNAs are reverse transcribed into double stranded DNA, and transcribed once again with a polymerase such as T7 or SP6. The resulting products, whether truncated or complete, indicate ABCR-specific sequences.

Davey, C., et al., European Patent Application Publication No. 329,822, incorporated herein by reference in its entirety, disclose a nucleic acid amplification process involving cyclically synthesizing single-stranded RNA ("ssRNA"), ssDNA, and double-stranded DNA ("dsDNA") which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller, H. I., et al., PCT application WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A. In: *PCR Protocols: A Guide to Methods and Applications* 1990, Academic Press, N.Y.) and "one-sided PCR" (Ohara, O., et al., *Proc. Natl. Acad. Sci.* (U.S.A.) 1989, 86:5673-5677), all references herein incorporated by reference in their entirety.

Methods based on ligation of two (or more) oligonucleotides in the presence of nucleic acid having the sequence of the resulting "di-oligonucleotide", thereby amplifying the di-oligonucleotide (Wu, D. Y. et al., Genomics 1989, 4:560, incorporated herein by reference in its entirety), may also be used in the amplification step of the present invention.

Test fragment and control fragment may be amplified by any amplification methods known to those of skill in the art, including and not limited to the amplification methods set forth above. For purposes of the present invention, amplification of sequences encoding patient and wild-type ABCR includes amplification of a portion of a sequence such as and not limited to a portion of an ABCR sequence of SEQ ID NO:1, such as sequence of a length of about 10 nucleotides to about 1,000 nucleotides, more preferably about 10 nucleotides to about 100 nucleotides, or having at least 10 nucleotides occurring anywhere within the SEQ ID NO:1, where sequence differences are known to occur within ABCR test fragments. Thus, for example, a portion of the sequence encoding ABCR of a patient sample and a control sample may be amplified to detect sequence differences between these two sequences.

Following amplification of the test fragment and control fragment, comparison between the amplification products of the test fragment and control fragment is carried out. Sequence changes such as and not limited to nucleic acid transition, transversion, and restriction digest pattern alterations may be detected by comparison of the test fragment with the control fragment.

Alternatively, the presence or absence of the amplification product may be detected. The nucleic acids are fragmented into varying sizes of discrete fragments. For example, DNA fragments may be separated according to molecular weight by methods such as and not limited to electrophoresis through an agarose gel matrix. The gels are then analyzed by Southern hybridization. Briefly, DNA in the gel is transferred to a hybridization substrate or matrix such as and not limited to a nitrocellulose sheet and a nylon membrane. A labeled probe encoding an ABCR mutation is applied to the matrix under selected hybridization conditions so as to hybridize with complementary DNA localized on the matrix. The probe may be of a length capable of forming a stable duplex. The probe may have a size range of about 200 to about 10,000 nucleotides in length, preferably about 500 nucleotides in length, and more preferably about 2,454 nucleotides in length. Mismatches which permit substantial similarity to the probe, such as and not limited to sequences with similar hydrophobicity, hydrophilicity, basicity, and acidity, will be known to those of skill in the art once armed with the present disclosure. Various labels for visualization or detection are known to those of skill in the art, such as and not limited to fluorescent staining, ethidium bromide staining for example, avidin/biotin, radioactive labeling such as $^{32}$P labeling, and the like. Preferably, the product such as the PCR product, may be run on an agarose gel and visualized using a stain such as ethidium bromide. See Sambrook et al., supra. The matrix may then be analyzed by autoradiography to locate particular fragments which hybridize to the probe. Yet another alternative is the sequencing of the test fragment and the control fragment to identify sequence differences. Methods of nucleic acid sequencing are known to those of skill in the art, including and not limited to the methods of Maxam and Gilbert, *Proc. Natl. Acad. Sci. USA* 1977, 74, 560-564 and Sanger, *Proc. Natl. Acad. Sci., USA* 1977, 74, 5463-5467.

A pharmaceutical composition comprising all or part of a sequence for ABCR may be delivered to a patient suspected of having retinal or macular degeneration. The sequence may be an antisense sequence. The composition of the present invention may be administered alone or may generally be administered in admixture with a pharmaceutical carrier. The pharmaceutically-acceptable carrier may be selected with regard to the intended route of administration and the standard pharmaceutical practice. The dosage will be about that of the sequence alone and will be set with regard to weight, and clinical condition of the patient. The proportional ratio of active ingredient to carrier will naturally depend, inter alia, on the chemical nature, solubility, and stability of the sequence, as well as the dosage contemplated.

The sequences of the invention may be employed in the method of the invention singly or in combination with other compounds, including and not limited to other sequences set forth in the present invention. The method of the invention may also be used in conjunction with other treatments such as and not limited to antibodies, for example. For in vivo applications the amount to be administered will also depend on such factors as the age, weight, and clinical condition of the patient. The composition of the present invention may be administered by any suitable route, including as an eye drop, inoculation and injection, for example, intravenous, intraocular, oral, intraperitoneal, intramuscular, subcutaneous, topically, and by absorption through epithelial or mucocutaneous linings, for example, conjunctival, nasal, oral, vaginal, rectal and gastrointestinal.

The mode of administration of the composition may determine the sites in the organism to which the compound will be delivered. For instance, topical application may be administered in creams, ointments, gels, oils, emulsions, pastes, lotions, and the like. For parenteral administration, the composition may be used in the form of sterile aqueous or non-aqueous solution which may contain another solute, for example, sufficient salts, glucose or dextrose to make the solution isotonic. A non-aqueous solution may comprise an oil, for example. For oral mode of administration, the present invention may be used in the form of tablets, capsules, lozenges, troches, powders, syrups, elixirs, aqueous solutions and suspension, and the like. Various disintegrants, such as starch, and lubricating agents may be used. For oral administration in capsule form, useful diluents are lactose and high molecular weight polyethylene glycols. When aqueous suspensions are required for oral use, certain sweetening and/or flavoring agents may be added.

A diagnostic kit for detecting retinal or macular degeneration comprising in one or more containers at least one primer which is complementary to an ABCR sequence and a means for visualizing amplified DNA is also within the scope of the present invention. Alternatively, the kit may comprise two primers. In either case, the primers may be selected from the group consisting of SEQ ID NOS:12-113, for example. The diagnostic kit may comprise a pair of primers wherein one primer within said pair is complementary to a region of the ABCR gene, wherein one of said pair of primers is selected from the group consisting of SEQ ID NO: 12-113, a probe specific to the amplified product, and a means for visualizing amplified DNA, and optionally including one or more size markers, and positive and negative controls. The diagnostic kit of the present invention may comprise one or more of a fluorescent dye such as ethidium bromide stain, $^{32}$P, and biotin, as a means for visualizing or detecting amplified DNA. Optionally the kit may include one or more size markers, positive and negative controls, restriction enzymes, and/or a probe specific to the amplified product.

The following examples are illustrative but are not meant to be limiting of the invention.

EXAMPLES

Identification of the ABCR as a Candidate Gene for STGD

One of the 21 new human genes from the ABC superfamily, hereafter called ABCR (retina-specific ABC transporter), was identified (Allikmets et al. 1996) among expressed sequence tags (ESTs) obtained from 5,000 human retina cDNA clones (Wang, Y., Macke, J. P., Abella, B. S., Andreasson, K., Worley, P., Gilbert, D. J., Copeland, N. G., Jenkins, N. A., and Nathans, J. (1996)) and among ESTs obtained from human retina cDNA clones by the I.M.A.G.E. consortium (Lennon et al., 1996). ABCR is closely related to the previously described mouse and human ABC1 and ABC2 genes (Luciani et al., 1994; Allikmets et al., 1995). To determine whether ABCR might cause a disease, the gene was mapped with a whole genome radiation hybrid panel (GeneBridge 4; Research Genetics, Huntsville, Ala.). ABCR mapped to the human chromosome 1p13-p21 region, close to microsatellite markers D1S236 and D1S188. To define further the location of the gene, PCR primers, 3'UTR-For 5'ATCCTCTGACTCAGCAATCACA, SEQ ID NO: 7, and 3'UTR-Rev 5'TTGCAATTACAAATGCAATGG, SEQ ID NO:8, from the putative 3' untranslated region were used to screen YACs from the previously described contig between these anonymous markers (Anderson et al., 1995). At least 12 YACs contain the 3' end of the ABCR gene, including 924_e_9, 759_d_7, 775_c._2, 782_b_4, 982_g_5, 775_b_2, 765_a_3, 751_f_2, 848_e_3, 943_h_8, 934_g_7, and 944_b_12

Figure 1B:
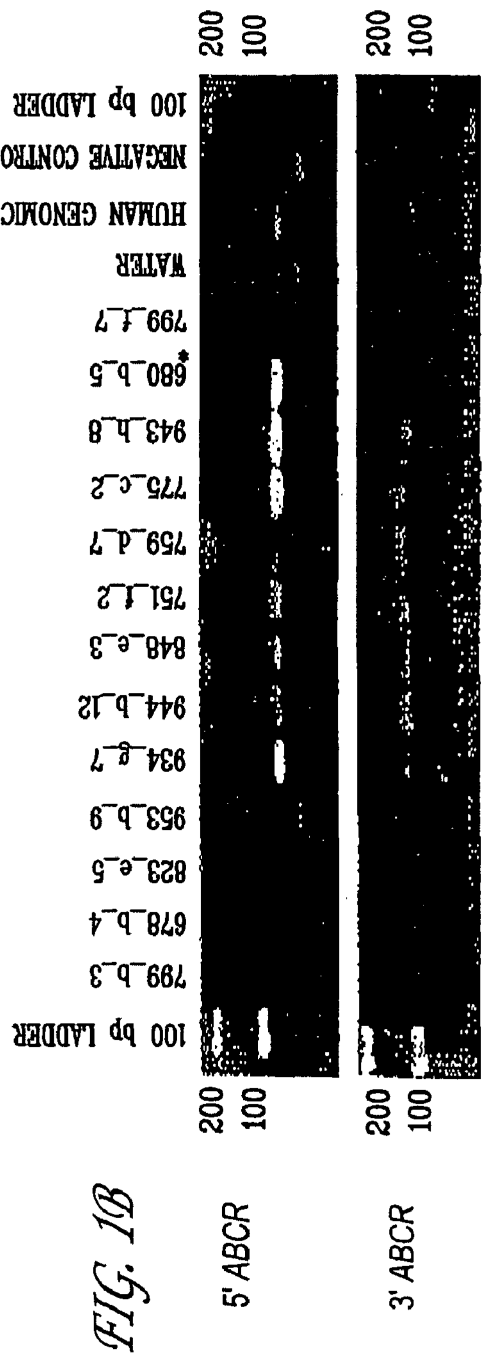

(FIG. 1). These YACs delineate a region containing the STGD gene between markers D1S3361 and D1S236 (Anderson et al., 1995).

Expression of the ABCR Gene

Additional support suggesting that ABCR is a candidate STGD gene came from expression studies and inspection of the EST databases.

Searches of the dbEST (Boguski et al., 1993) database were performed with BLAST on the NCBI file server (Altschul et al., 1990). Amino acid alignments were generated with PILEUP (Feng and Doolittle, 1987). Sequences were analyzed with programs of the Genetics Computer Group package (Devereaux et al., 1984) on a VAX computer.

Clones corresponding to the mouse ortholog of the human ABCR gene were isolated from the mouse retina cDNA library and end-sequenced. The chromosomal location of the mouse ABCR gene was determined on The Jackson Laboratory (Bar Harbor, Me.) interspecific backcross mapping panel (C57BL/6JEi×SPRET/Ei)F1×SPRET/Ei (Rowe et al., 1994) known as Jackson BSS. Mapping was performed by SSCP analysis with the primers MABCR1F 5'ATC CAT ACC CTT CCC ACT CC, SEQ ID NO:9, and MABCR1R 5'GCA GCA GAA GAT AAG CAC ACC, SEQ ID NO. 10. The allele pattern of the ABCR was compared to the 250 other loci mapped previously in the Jackson BSS cross (http://wwwjax-.org).

DNA fragments used as probes were purified on a 1% low-melting temperature agarose gel. The probe sequences are set forth within the genomic sequence of SEQ ID NO: 1 and FIG. 3. DNA was labeled directly in agarose with the Random Primed DNA Labeling Kit (Boehringer Mannheim, Indianapoils, Ind.) and hybridized to multiple tissue Northern blot and a Master blot (Clontech, Palo Alto, Calif.), according to the manufacturer's instructions. Each blot contained 2 μg of poly $A^+$ RNA from various human tissues. Total RNA was isolated from adult rat tissues using the guanidinium thiocyanate method (Chomczynski and Saachi, 1987 and resolved by agarose gel electrophoresis in the presence of formaldehyde (Sambrook et al., 1989). Hybridization with the mouse ABCR probe was performed in 50% formamide, 5×SSC at 42° C., and filters were washed in 0.1×SSC at 68° C.

Figure 2:
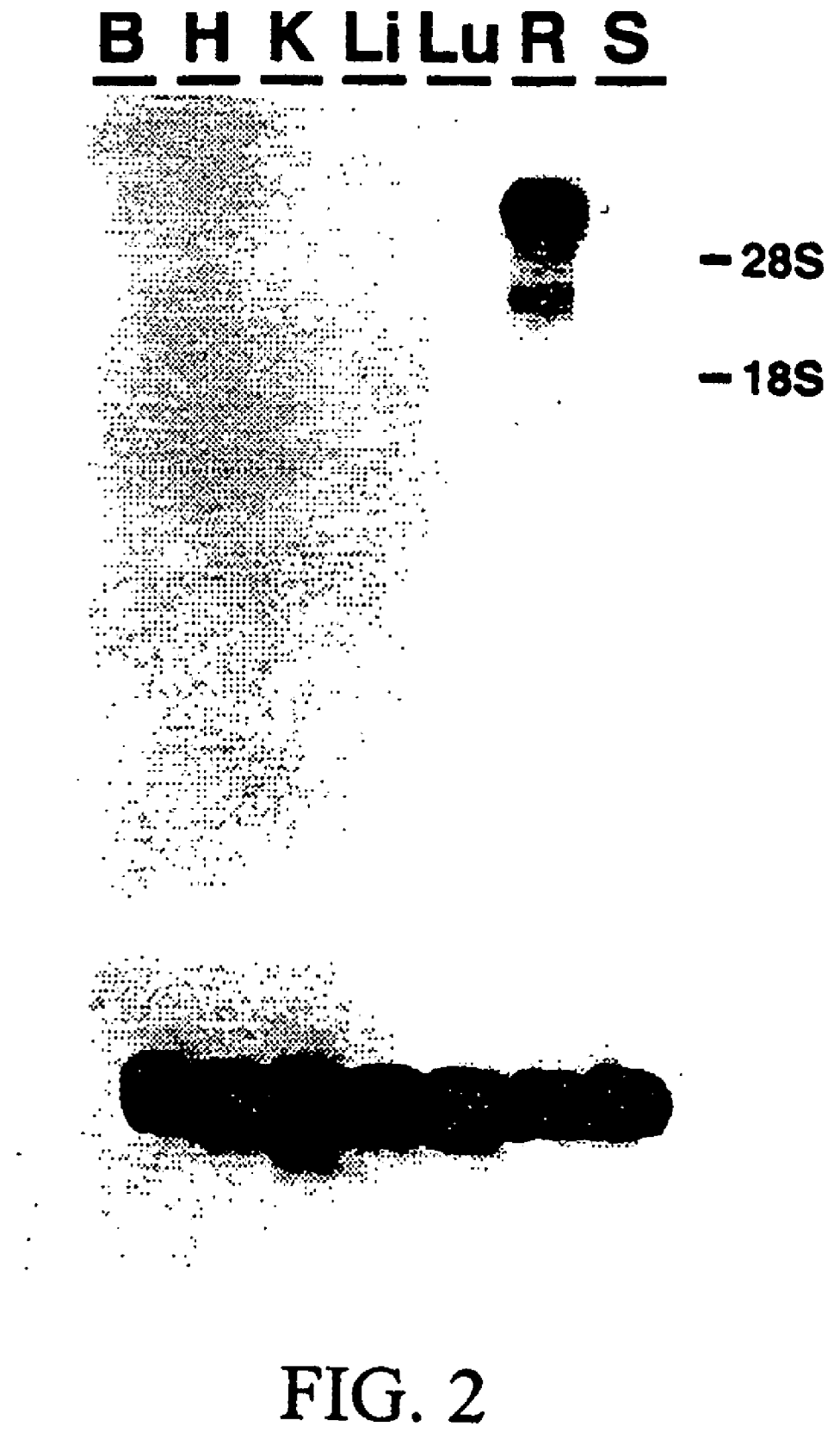

Hybridization of a 3'ABCR cDNA probe to a multiple tissue Northern blot and a MasterBlot (Clontech, Palo Alto, Calif.) indicated that the gene was not expressed detectably in any of the 50 non-retinal fetal and adult tissues examined, consistent with the observation that all 12 of the ABCR clones in the EST database originated from retinal cDNA libraries. Furthermore, screening cDNA libraries from both developing mouse eye and adult human retina with ABCR probes revealed an estimated at 0.1%-1% frequency of ABCR clones of all cDNA clones in the library. Hybridization of the ABCR probe to a Northern blot containing total RNA from rat retina and other tissues showed that the expression of this gene is uniquely retina-specific (FIG. 2). The transcript size is estimated to be 8 kb.

Sequence and Exon/Intron Structure of the ABCR cDNA

Several ESTs that were derived from retina cDNA libraries and had high similarity to the mouse Abc1 gene were used to facilitate the assembly of most of the ABCR cDNA sequence. Retina cDNA clones were linked by RT-PCR, and repetitive screening of a human retina cDNA library with 3' and 5' PCR probes together with 5' RACE were used to characterize the terminal sequences of the gene.

cDNA clones containing ABCR sequences were obtained from a human retina cDNA library (Nathans et al., 1986) and sequenced fully. Primers were designed from the sequences of cDNA clones from 5' and 3' regions of the gene and used to link the identified cDNA clones by RT-PCR with retina QUICK-Clone cDNA (Clontech, Palo Alto, Calif.) as a template. PCR products were cloned into pGEM®-T vector (Promega, Madison, Wis.). Mouse ABCR cDNA clones were obtained from screening a developing mouse eye cDNA library (H. Sun, A. Lanahan, and J. Nathans, unpublished). The pGEM®-T Vector is prepared by cutting pGEM®-5Zf (+) DNA with EcoR V and adding to a 3' terminal thymidine to both ends. These single 3'-T overhangs at the insertion site greatly improve the efficiency of ligation of PCR products because of the nontemplate-dependent addition of a single deoxyadenosine (A) to the 3'-ends of PCR products by many thermostable polymerases. The pGEM®5Zf(+) Vector contains the origin of replication of the filamentous phage f1 and can be used to produce ssDNA. The plasmid also contains T7 and SP6 RNA polymerase promoters flanking a multiple cloning region within the .alpha.-peptide coding region for the enzyme beta-galactosidase. Insertional inactivation of the alpha-peptide allows recombinant clones to be identified directly by color screening on indicator plates. cDNA clones from various regions of the ABCR gene were used as probes to screen a human genomic library in Lambda FIX II (#946203, Stratagene, LaJolla, Calif.). Overlapping phase clones were mapped by EcoRI and BamHI digestion. A total of 6.9 kb of the ABCR sequence was assembled, (FIG. 3) resulting in a 6540 bp (2180 amino acid) open reading frame.

Screening of a bacteriophage lambda human genomic library with cDNA probes yielded a contig that spans approximately 100 kb and contains the majority of the ABCR coding region. The exon/intron structure of all fifty one exons of the gene were characterized by direct sequencing of genomic and cDNA clones. Intron sizes were estimated from the sizes of PCR products using primers from adjacent exons with genomic phage clones as templates.

Primers for the cDNA sequences of the ABCR were designed with the PRIMER program (Lincoln et al., 1991). Both ABCR cDNA clones and genomic clones became templates for sequencing. Sequencing was performed with the Taq Dyedeoxy Terminator Cycle Sequencing kit (Appliedn Biosystems, Foster City, Calif.), according to the manufacturer's instructions. Sequencing reactions were resolved on an ABI 373A automated sequencer. Positions of introns were determined by comparison between genomic and cDNA sequences. Primers for amplification of individual exons were designed from adjacent intron sequences 20-50 bp from the splice site and are set forth in Table 1.

TABLE 1

Exon/intron Primers for ABCR

| PRIMER | SEQUENCE | SEQ ID NO |
|---|---|---|
| ABCR.EXON1:F | ACCCTCTGCTAAGCTCAGAG | 12 |
| ABCR.EXON1 R | ACCCCACACTTCCAACCTG | 13 |
| ABCR.EXON2:F | AAGTCCTACTGCACACATGG | 14 |
| ABCR.EXON2:R | ACACTCCCACCCCAAGATC | 15 |
| ABCR.EXON3:F | TTCCCAAAAAGGCCAACTC | 16 |
| ABCR.EXON3:R | CACGCACGTGTGCATTCAG | 17 |
| ABCR.EXON4:F | GCTATTTCCTTATTAATGAGGC | 18 |
| ABCR.EXON4:R | CCAACTCTCCCTGTTCTTTC | 19 |
| ABCR.EXON5:F | TGTTTCCAATCGACTCTGGC | 20 |
| ABCR.EXON5:R | TTCTTGCCTTTCTCAGGCTGG | 21 |
| ABCR.EXON6:F | GTATTCCCAGGTTCTGTGG | 22 |
| ABCR.EXON6:R | TACCCCAGGAATCACCTTG | 23 |

TABLE 1-continued

Exon/intron Primers for ABCR

| PRIMER | SEQUENCE | SEQ ID NO |
|---|---|---|
| ABCR.EXON7:F | AGCATATAGGAGATCAGACTG | 24 |
| ABCR.EXON7:R | TGACATAAGTGGGGTAAATGG | 25 |
| ABCR.EXON8:F | GAGCATTGGCCTCACAGCAG | 26 |
| ABCR.EXON8:R | CCCCAGGTTTGTTTCACC | 27 |
| ABCR.EXON9:F | AGACATGTGATGTGGATACAC | 28 |
| ABCR.EXON9:R | GTGGGAGGTCCAGGGTACAC | 29 |
| ABCR.EXON10:F | AGGGGCAGAAAAGACACAC | 30 |
| ABCR.EXON10:R | TAGCGATTAACTCTTTCCTGG | 31 |
| ABCR.EXON11:F | CTCTTCAGGGAGCCTTAGC | 32 |
| ABCR.EXON11:R | TTCAAGACCACTTGACTTGC | 33 |
| ABCR.EXON12:F | TGGGACAGCAGCCTTATC | 34 |
| ABCR.EXON12:R | CCAAATGTAATTTCCCACTGAC | 35 |
| ABCR.EXON13:F | AATGAGTTCCGAGTCACCCTG | 36 |
| ABCR.EXON13:R | CCCATTCGCGTGTCATGG | 37 |
| ABCR.EXON14:F | TCCATCTGGGCTTTGTTCTC | 38 |
| ABCR.EXON14:R | AATCCAGGCACATGAACAGG | 39 |
| ABCR.EXON15:F | AGGCTGGTGGGAGAGAGC | 40 |
| ABCR.EXON15:R | AGTGGACCCCCTCAGAGG | 41 |
| ABCR.EXON16:F | CTGTTGCATTGGATAAAAGGC | 42 |
| ABCR.EXON16:R | GATGAATGGAGAGGGCTGG | 43 |
| ABCR.EXON17:F | CTGCGGTAAGGTAGGATAGGG | 44 |
| ABCR.EXON17:R | CACACCGTTTACATAGAGGGC | 45 |
| ABCR.EXON18:F | CCTCTCCCCTCCTTTCCTG | 46 |
| ABCR.EXON18:R | GTCAGTTTCCGTAGGCTTC | 47 |
| ABCR.EXON19:F | TGGGGCCATGTAATTAGGC | 48 |
| ABCR.EXON19:R | TGGGAAAGAGTAGACAGCCG | 49 |
| ABCR.EXON20:F | ACTGAACCTGGTGTGGGG | 50 |
| ABCR.EXON20:R | TATCTCTGCCTGTGCCCAG | 51 |
| ABCR.EXON21:F | GTAAGATCAGCTGCTGGAAG | 52 |
| ABCR.EXON2I:R | GAAGCTCTCCTGCACCAAGC | 53 |
| ABCR.EXON22:F | AGGTACCCCCACAATGCC | 54 |
| ABCR.EXON22:R | TCATTGTGGTTCCAGTACTCAG | 55 |
| ABCR.EXON23:F | TTTTTGCAACTATATAGCCAGG | 56 |
| ABCR.EXON23:R | AGCCTGTGTGAGTAGCCATG | 57 |
| ABCR.EXON24:F | GCATCAGGGCGAGGCTGTC | 58 |
| ABCR.EXON24:R | CCCAGCAATACTGGGAGATG | 59 |
| ABCR.EXON25:F | GGTAACCTCACAGTCTTCC | 60 |
| ABCR.EXON25:R | GGGAACGATGGCTTTTTGC | 61 |
| ABCR.EXON26:F | TCCCATTATGAAGCAATACC | 62 |
| ABCR.EXON26:R | CCTTAGACTTTCGAGATGG | 63 |
| ABCR.EXON27:F | GCTACCAGCCTGGTATTTCATTG | 64 |
| ABCR.EXON27:R | GTTATAACCCATGCCTGAAG | 65 |
| ABCR.EXON28:F | TGCACGCGCACGTGTGAC | 66 |
| ABCR.EXON28:R | TGAAGGTCCCAGTGAAGTGGG | 67 |
| ABCR.EXON29:F | CAGCAGCTATCCAGTAAAGG | 68 |
| ABCR.EXON29:R | AACGCCTGCCATCTTGAAC | 69 |
| ABCR.EXON30:F | GTTGGGCACAATTCTTATGC | 70 |
| ABCR.EXON30:R | GTTGTTTGGAGGTCAGGTAC | 71 |
| ABCR.EXON31:F | AACATCACCCAGCTGTTCCAG | 72 |
| ABCR.EXON31:R | ACTCAGGAGATACCAGGGAC | 73 |
| ABCR.EXON32:F | GGAAGACAACAAGCAGTTTCAC | 74 |
| ABCR.EXON32:R | ATCTACTGCCCTGATCATAC | 75 |
| ABCR.EXON33:F | AAGACTGAGACTTCAGTCTTC | 76 |
| ABCR.EXON33:R | GGTGTGCCTTTTAAAAGTGTGC | 77 |
| ABCR.EXON34:F | TTCATGTTTCCCTACAAAACCC | 78 |
| ABCR.EXON34:R | CATGAGAGTTTCTCATTCATGG | 79 |
| ABCR.EXON35:F | TGTTTACATGGTTTTTAGGGCC | 80 |
| ABCR.EXON35:R | TTCAGCAGGAGGAGGGATG | 81 |
| ABCR.EXON36:F | CCTTTCCTTCACTGATTTCTGC | 82 |
| ABCR.EXON36:R | AATCAGCACTTCGCGGTG | 83 |
| ABCR.EXON37:F | TGTAAGGCCTTCCCAAAGC | 84 |
| ABCR.EXON37:R | TGGTCCTTCAGCGCACACAC | 85 |
| ABCR.EXON38:F | CATTTGCAGAGCTGGCAGC | 86 |
| ABCR.EXON38:R | CTTCTGTCAGGAGATGATCC | 87 |
| ABCR.EXON39:F | GGAGTGCATTATATCCAGACG | 88 |
| ABCR.EXON39:R | CCTGGCTCTGCTTGACCAAC | 89 |
| ABCR.EXON40:F | TGCTGTCCTGTGAGAGCATC | 90 |
| ABCR.EXON40:R | GTAACCCTCCCAGCTTTGG | 91 |
| ABCR.EXON41:F | CAGTTCCCACATAAGGCCTG | 92 |
| ABCR.EXON41:R | CAGTTCTGGATGCCCTGAG | 93 |
| ABCR.EXON42:F | GAAGAGAGGTCCCATGGAAAGG | 94 |
| ARCR.EXON42:R | GCTTGCATAAGCATATCAATTG | 95 |
| ABCR.EXON43:F | CTCCTAAACCATCCTTTGCTC | 96 |
| ABCR.EXON43:R | AGGCAGGCACAAGAGCTG | 97 |
| ABCR.EXON44:F | CTTACCCTGGGGCCTGAC | 98 |
| ABCR.EXON44:R | CTCAGAGCCACCCTACTATAG | 99 |
| ABCR.EXON45:F | GAAGCTTCTCCAGCCCTAGC | 100 |
| ABCR.EXON45:R | TGCACTCTCATGAAACAGGC | 101 |
| ABCR.EXON46:F | GTTTGGGGTGTTTGCTTGTC | 102 |
| ABCR.EXON46:R | ACCTCTTTCCCCAACCCAGAG | 103 |
| ABCR.EXON47:F | GAAGCAGTAATCAGAAGGGC | 104 |
| ABCR.EXON47:R | GCCTCACATTCTTCCATGCTG | 105 |
| ABCR.EXON48:F | TCACATCCCACAGGCAAGAG | 106 |
| ABCR.EXON48:R | TTCCAAGTGTCAATGGAGAAC | 107 |
| ABCR.EXON49:F | ATTACCTTAGGCCCAACCAC | 108 |
| ABCR.EXON49:R | ACACTGGGTGTTCTGGACC | 109 |
| ABCR.EXON50:F | GTGTAGGGTGGTGTTTTCC | 110 |
| ABCR.EXON50:R | AAGCCCAGTGAACCAGCTGG | 111 |
| ABCR.EXON51:F | TCAGCTGAGTGCCCTTCAG | 112 |
| ABCR.EXON51:R | AGGTGAGCAAGTCAGTTTCGG | 113 |

In Table 1, "F" indicates forward, i.e., 5' to 3', "R" indicates reverse, i.e., 3' to 5'. PCR conditions were 95° C. for 8 minutes; 5 cycles at 62° C. for 20 seconds, 72° C. for 30 seconds; 35 cycles at 60° C. for 20 seconds, 72° C. for 30 seconds; 72° C. for 5 minutes (except that a was performed at 94° C. for 5 minutes); 5 cycles at 94° C. for 40 seconds; 60° C. for 30 seconds; 72° C. for 20 seconds; 35 cycles at 94° C. for 40 seconds; 56° C. for 30 seconds; 72° C. for 20 seconds, and 72° C. for 5 minutes.

Amplification of exons was performed with AmpliTaq Gold polymerase in a 25 microliter volume in 1×PCR buffer supplied by the manufacturer (Perkin Elmer, Foster City, Calif.). Samples were heated to 95° C. for 10 minutes and amplified for 35-40 cycles at 96° C. for 20 seconds; 58° C. for 30 seconds; and 72° C. for 30 seconds. PCR products were analyzed on 1-1.5% agarose gels and in some cases digested with an appropriate restriction enzyme(s) to verify their sequence. Primer sequences and specific reaction conditions are set forth in Table 1. The sequence of the ABCR cDNA has been deposited with GenBank under accession #U88667.

Homology to ABC Superfamily Members

A BLAST search revealed that ABCR is most closely related to the previously characterized mouse Abc1 and Abc2 genes (Luciani et al., 1994) and to another human gene (ABCC) which maps to chromosome 16p13.3 (Klugbauer and Hofmann, 1996). These genes, together with ABCR and a gene from *C. elegans* (GenBank #Z29117), form a subfamily of genes specific to multicellular organisms and not represented in yeast (Michaelis and Berkower, 1995; Allikmets et al., 1996). Alignment of the cDNA sequence of ABCR with the Abc1, ABc2, and ABCC genes revealed, as expected, the highest degree of homology within the ATP-binding cassettes. The predicted amino acid identity of the ABCR gene to mouse Abc1 was 70% within the ATP-binding domains; even within hydrophobic membrane-spanning segments, homology ranged between 55 and 85% (FIG. 4). The putative ABCR initiator methionine shown in FIGS. 3 and 4 corresponds to a methionine codon at the 5' end of Abc1 (Luciani et al., 1994).

ABCR shows the composition of a typical full-length ABC transporter that consists of two transmembrane domains (TM), each with six membrane spanning hydrophobic segments, as predicted by a hydropathy plot (data not shown), and two highly conserved ATP-binding domains (FIGS. 3 and 4). In addition, the HH1 hydrophobic domain, located between the first ATP and second TM domain and specific to this subfamily (Luciani et al., 1994), showed a predicted 57% amino acid identity (24 of 42 amino acids) with the mouse Abc1 gene.

Figure 5:
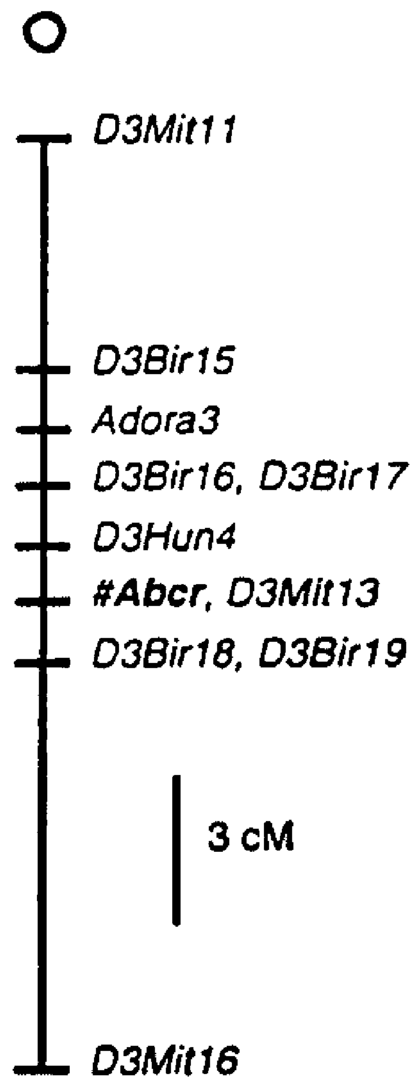
FIG. 5 exhibits the location of Abcr from a Jackson BSS Backcross showing a portion of mouse chromosome 3. The map is depicted with the centromere toward the top. A 3 cM scale bar is also shown. Loci mapping to the same position are listed in alphabetical order.

To characterize the mouse ortholog of ABCR, cDNA clones from a developing mouse eye library were isolated. A partial sequence of the mouse cDNA was utilized to design PCR primers to map the mouse ABCR gene in an interspecific backcross mapping panel (Jackson BSS). The allele pattern of ABCR was compared to 2450 other loci mapped previously in the Jackson BSS cross; linkage was found to the distal end of chromosome 3 (FIG. 5). No recombinants were observed between ABCR and D13Mit13. This region of the mouse genome is syntenic with human chromosome 1p13-p21. Thus far, no eye disease phenotype has been mapped to this region of mouse chromosome 3.

Compound Heterozygous and Homozygous Mutations in STGD Patients

One hundred forty-five North American and three Saudi Arabian families with STGD/FFM were examined. Among these, at least four were consanguineous families in which the parents were first cousins. Entry criteria for the characterization of the clinical and angiographic diagnosis of Stargardt disease, ascertainment of the families, and methodology for their collection, including the consanguineous families from Saudi Arabia, were as provided in Anderson et al., 1995; and Anderson, 1996.

Mutational analysis of the ABCR gene was pursued in the above identified one hundred forty-eight STGD families previously ascertained by strict definitional criteria and shown to be linked to chromosome 1 p (Anderson et al., 1995; Anderson, 1996). To date, all 51 exons have been used for mutation analysis.

Mutations were detected by a combined SSCP (Orita et al., 1989) and heteroduplex analysis (White et al., 1992) under optimized conditions (Glavac and Dean, 1993). Genomic DNA samples (50 ng) were amplified with AmpliTaq Gold polymerase in 1×PCR buffer supplied by the manufacturer (Perkin Elmer, Foster City, Calif.) containing [α-$^{32}$P] dCTP. Samples were heated to 95° C. for 10 minutes and amplified for 35-40 cycles at 96° C. for 20 seconds; 58° C. for 30 seconds; and 72° C. for 30 seconds. Products were diluted in 1:3 stop solution, denatured at 95° C. for 5 minutes, chilled in ice for 5 minutes, and loaded on gels. Gel formulations include 6% acrylamide:Bis (2.6% cross-linking), 10% glycerol at room temperature, 12W; and 10% acrylamide:Bis (1.5% cross-linking), at 4° C., 70 W. Gels were run for 2-16 hours (3000 Vh/100 bp), dried, and exposed to X-ray film for 2-12 hours. Some exons were analyzed by SSCP with MDE acrylamide (FMC Bioproducts, Rockland, Me.) with and without 10% glycerol for 18 hours, 4 watts at room temperature with .alpha α.-P$^{32}$-dCTP labeled DNA. Heteroduplexes were identified from the double-stranded DNA at the bottom of the gels, and SSCPs were identified from the single-stranded region. Samples showing variation were compared with other family members to assess segregation of the alleles and with at least 40 unrelated control samples, from either Caucasian or Saudi Arabian populations, to distinguish mutations from polymorphisms unrelated to STGD. PCR products with SSCP or heteroduplex variants were obtained in a 25 μl volume, separated on a 1% agarose gel, and isolated by a DNA purification kit (PGC Scientific, Frederick, Md.). Sequencing was performed on an ABI sequencer with both dye primer and dye terminator chemistry.

Some mutations were identified with a heteroduplex analysis protocol (Roa et al., 1993). Equimolar amounts of control and patient PCR products were mixed in 0.2 ml tubes. Two volumes of PCR products from a normal individual served as a negative control, and MPZ exon 3 from patient BAB731 as a positive control (Roa et al., 1996). Samples were denatured at 95° C. for 2 minutes and cooled to 35° C. at a rate of 1° C./minute. Samples were loaded onto 1.0 mm thick, 40 cm MDE gels (FMC Bioproducts, Rockland, Me.,), electrophoresed at 600-800 V for 15-20 hours, and visualized with ethidium bromide. Samples showing a variant band were reamplified with biotinylated forward and reverse primers and immobilized on streptavidin-conjugated beads (Warner et al., 1996). The resulting single strands were sequenced by the dideoxy-sequencing method with Sequenase 2.0 (Amersham, Arlington Heights, Ill.).

A total of seventy five mutations were identified, the majority representing missense mutations in conserved amino acid positions. However, several insertions and deletions representing frameshifts were also found (Table 2). Two missense alterations (D847H, R943Q) were found in at least one control individual, suggesting that they are neutral polymorphisms. The remaining mutations were found in patients having macular degeneration and were not found in at least 220 unrelated normal controls (440 chromosomes), consistent with the interpretation that these alterations represent disease-causing mutations, not polymorphisms. One of the mutations, 5892+1 G→T, occurs in family AR144 in which one of the affected children is recombinant for the flanking marker D1S236 (Anderson et al., 1995). This mutation, however, is present in the father as well as in both affected children. Therefore, the ABCR gene is non-recombinant with respect to the Stargardt disease locus.

Figure 6:
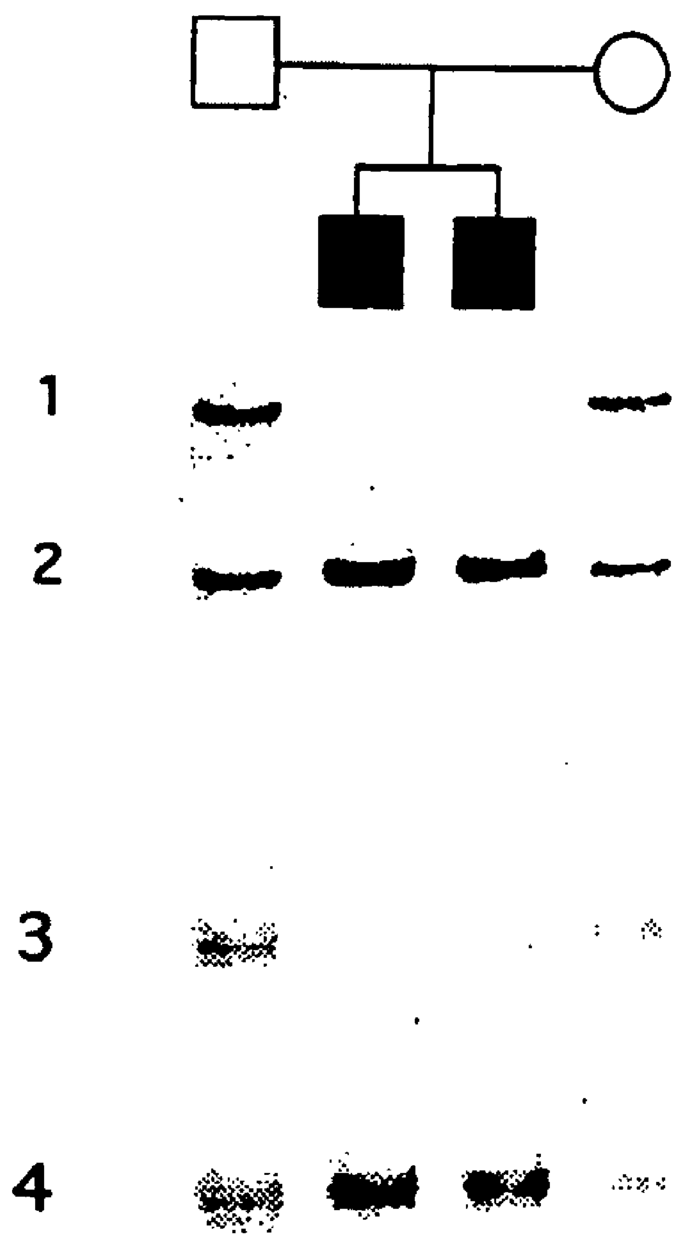
FIG. 6 shows the segregation of SSCP variants in exon 49 of the ABCR gene in kindred AR293. Sequence analysis of SSCP bands revealed the existence of wild-type sequence (bands 1 and 3) and mutant sequence (bands 2 and 4). DNA sequencing revealed a 15 base pair deletion, while the affected children (lanes 2 and 3) are homozygous. Haplotype analysis demonstrated homozygosity at the STGD locus in the two affected individuals.
Figure 7A:
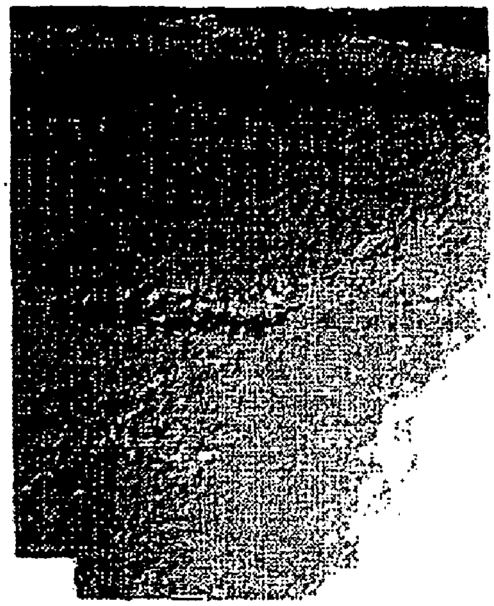
FIGS. 7A-H show the localization of ABCR transcripts to photoreceptor cells. In situ hybridization was performed with digoxygenin-labeled riboprobes and visualized using an alkaline phosphatase conjugated anti-digoxygenin antibody.
Figure 7B:
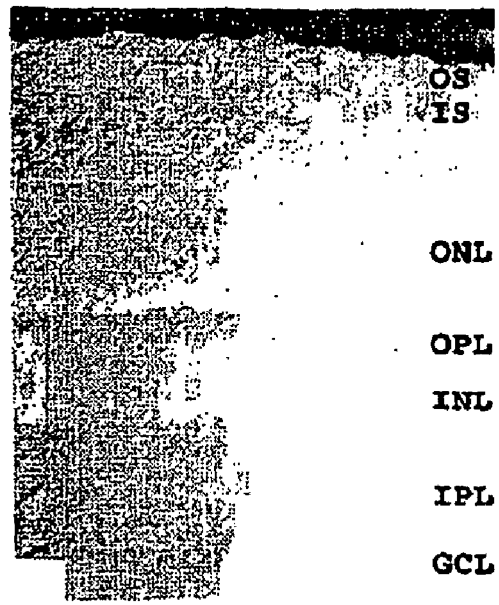
Figure 7C:
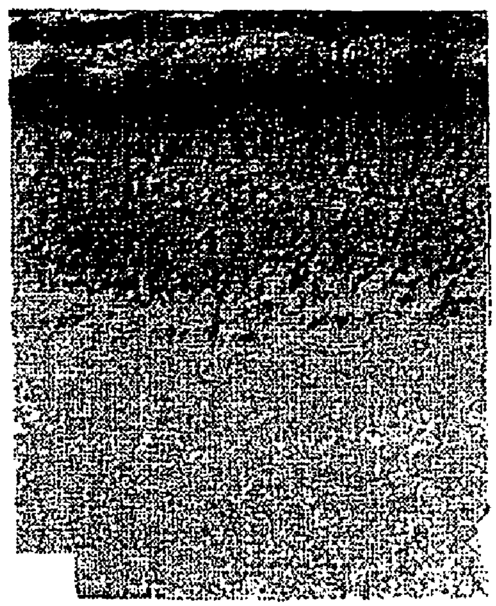
Figure 7D:
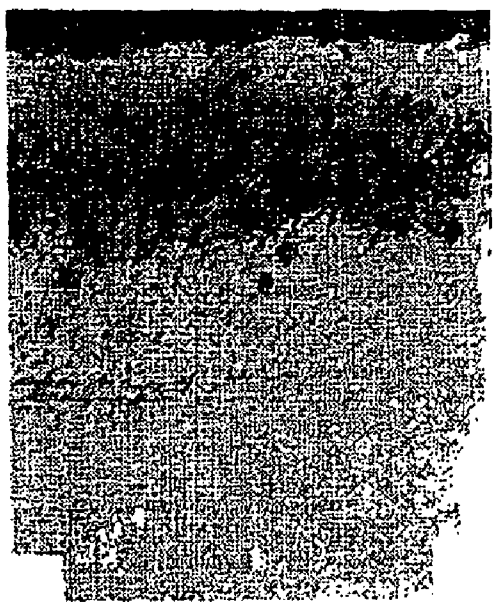
Figure 7E:
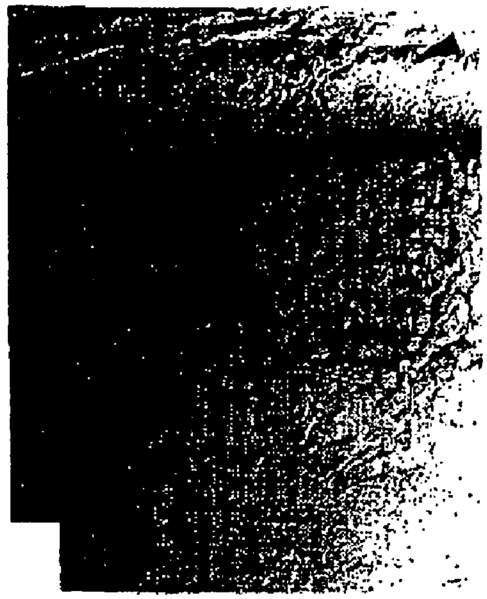
Figure 7F:
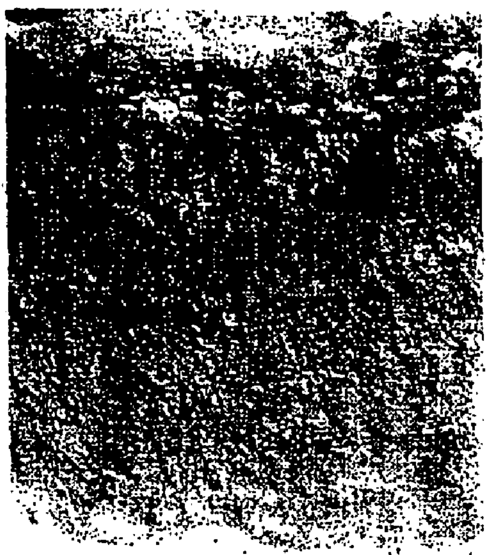
Figure 7G:
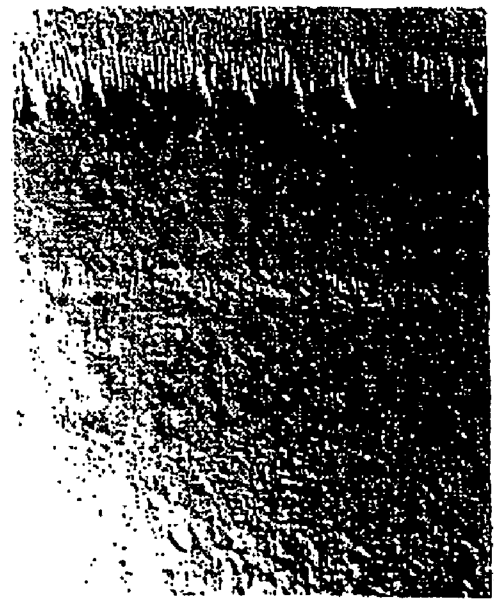
Figure 7H:
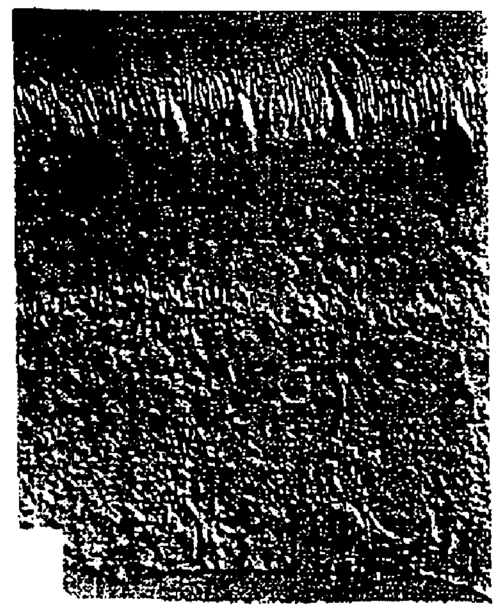
Figure 8:
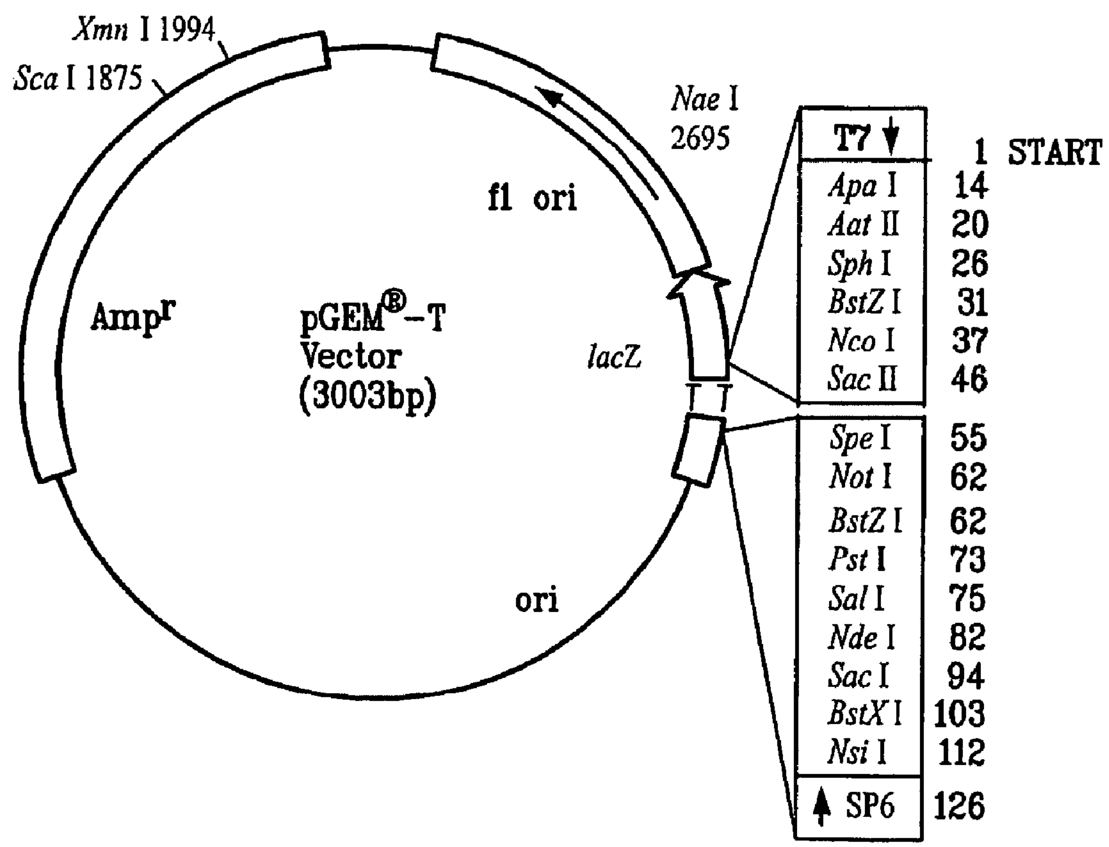
FIG. 8 provides a pGEM.®-T Vector map.

The mutations are scattered throughout the coding sequence of the ABCR gene (see Table 2 and FIG. 3), although clustering within the conserved regions of the ATP-binding domains is noticeable. Homozygous mutations were detected in three likely consanguineous families, two Saudi Arabian and one North American (Anderson et al., 1995), in each of which only the affected individuals inherited the identical disease allele (Table 2; FIG. 6). Forty two compound heterozygous families were identified in which the two disease alleles were transmitted from different parents to only the affected offspring (Table 2).

TABLE 2

Mutations in the ABCR gene in STGD Families

| Nucleotide | Amino Acid | #Families | Exon |
|---|---|---|---|
| 0223T->G | C75G | 1 | 3 |
| 0634C->T | R212C | 1 | 6 |
| 0664del13 | fs | 1 | 6 |
| 0746A->G | D249G | 1 | 6 |
| 1018T->G | Y340D | 2 | 8 |
| 1411 G->A | E471 K | 1 | 11 |
| 1569T->G | D523E | 1 | 12 |
| 1715G->A | R572Q | 2 | 12 |
| 1715G->C | R572P | 1 | 12 |
| 1804C->T | R602W | 1 | 13 |
| 1822T->A | F608I | 1 | 13 |
| 1917C->A | Y639X | 1 | 13 |
| 2453G->A | G818E | 1 | 16 |
| 2461T->A | W821R | 1 | 16 |
| 2536G->C | D846H | 1 | 16 |
| 2588G->C | G863A | 11 | 17 |
| 2791G->A | V931M | 1 | 19 |
| 2827C->T | R943W | 1 | 19 |
| 2884delC | fs | 1 | 19 |
| 2894A->G | N965S | 3 | 19 |
| 3083C->T | A1028V | 14 | 21 |
| 3211delGT | fs | 1 | 22 |
| 3212C->T | S1071L | 1 | 22 |
| 3215T->C | V1072A | 1 | 22 |
| 3259G->A | E1087K | 1 | 22 |
| 3322C->T | R1108C | 6 | 22 |
| 3364G->A | E1122K | 1 | 23 |
| 3385G->T | R1129C | 1 | 23 |
| 3386G->T | R1129L | 1 | 23 |
| 3602T->G | L1201R | 1 | 24 |
| 3610G->A | D1204N | 1 | 25 |
| 4139C->T | P1380L | 2 | 28 |
| 4195G->A | E1399K | 1 | 28 |
| 4222T->C | W1408R | 3 | 28 |
| 4232insTATG | fs | 1 | 28 |
| 4253+5G->T | splice | 1 | 28 |
| 4297G->A | V1433I | 1 | 29 |
| 4316G->A | G1439D | 1 | 29 |
| 4319T->C | F1440S | 1 | 29 |
| 4346G->A | W1449X | 1 | 29 |
| 4462T->C | C1488R | 1 | 30 |
| 4469G->A | C1490Y | 1 | 31 |
| 4577C->T | T1526M | 6 | 32 |
| 4594G->A | D1532N | 2 | 32 |
| 4947delC | fs | 1 | 36 |
| 5041 del15 | VVAIC1681del | 1 | 37 |
| 5196+2T->C | splice | 1 | 37 |
| 5281del9 | PAL1761del | 1 | 38 |
| 5459G->C | R1820P | 1 | 39 |
| 5512C->T | H1838Y | 1 | 40 |
| 5527C->T | R1843W | 1 | 40 |
| 5585+1G->A | splice | 1 | 41 |
| 5657G->A | G1886E | 1 | 41 |
| 5693G->A | R1898H | 4 | 41 |
| 5714+5G->A | splice | 8 | 41 |
| 5882G->A | G1961E | 16 | 43 |
| 5898+1G->A | splice | 3 | 43 |
| 5908C->T | L1970F | 1 | 44 |
| 5929G->A | G1977S | 1 | 44 |
| 6005+1 G->T | splice | 1 | 44 |
| 6079C->T | L2027F | 11 | 45 |
| 6088C->T | R2030X | 1 | 45 |
| 6089G->A | R2030Q | 1 | 45 |
| 6112C->T | R2038W | 1 | 45 |
| 6148G->C | V2050L | 2 | 46 |
| 6166A->T | K2056X | 1 | 46 |
| 6229C->T | R2077W | 1 | 46 |
| 6286G->A | E2096K | 1 | 47 |

TABLE 2-continued

Mutations in the ABCR gene in STGD Families

| Nucleotide | Amino Acid | #Families | Exon |
|---|---|---|---|
| 6316C->T | R2106C | 1 | 47 |
| 6391G->A | E2131K | 1 | 48 |
| 6415C->T | R2139W | 1 | 48 |
| 6445C->T | R2149X | 1 | 48 |
| 6543del36 | 1181del12 | 1 | 49 |
| 6709delG | fs | 1 | 49 |

Mutations are named according to standard nomenclature. The column headed "Exon" denotes which of the 51 exons of ABCR contain the mutation. The column headed "# Families" denotes the number of Stargardt families which displayed the mutation. The column headed "Nucleotide" gives the base number starting from the A in the initiator ATG, followed by the wild type sequence and an arrow indicating the base it is changed to: del indicates a deletion of selected bases at the given position in the ABCR gene; ins indicates an insertion of selected bases at the given position; splice donor site mutations are indicated by the number of the last base of the given exon, followed by a plus sign and the number of bases into the intron where the mutation occurs. The column headed "Amino Acid" denotes the amino acid change a given mutation causes; fs indicates a frameshift mutation leading to a truncated protein; splice indicates a splice donor site mutation; del indicates an in-frame deletion of the given amino acids.

Mutations are named according to standard nomenclature. Exon numbering according to the nucleotide position starting from the A in the initiator ATG.

In Situ Hybridization

STGD is characterized histologically by a massive accumulation of a lipofuscin-like substance in the retinal pigment epithelium (RPE). This characteristic has led to the suggestion that STGD represents an RPE storage disorder (Blacharski et al., 1988). It was therefore of interest that ABCR transcripts were found to be abundant in the retina. To identify the site(s) of ABCR gene expression at higher resolution and to determine whether the gene is also expressed in the RPE, the distribution of ABCR transcripts was visualized by in situ hybridization to mouse, rat, bovine, and macaque ocular tissues.

In situ hybridization with digoxigenin-labeled riboprobes was performed as described by Schaeren-Wiemers and Gerfin-Moser, 1993. For mouse and rat, unfixed whole eyes were frozen and sectioned; macaque retinas were obtained following cardiac perfusion with paraformaldehyde as described (Zhou et al., 1996). An extra incubation of 30 min in 1% Triton X-100, 1×PBS was applied to the fixed monkey retina sections immediately after the acetylation step. The templates for probe synthesis were: (1) a 1.6 kb fragment encompassing the 3' end of the mouse ABCR coding region, (2) a full length cDNA clone encoding the mouse blue cone pigment (Chiu et al., 1994), and (3) a macaque rhodopsin coding region segment encoding residues 133 to 254 (Nickells, R. W., Burgoyne, C. F., Quigley, H. A., and Zack, D. J. (1995)).

This analysis showed that ABCR transcripts are present exclusively within photoreceptor cells (FIG. 7). ABCR transcripts are localized principally to the rod inner segments, a distribution that closely matches that of rhodopsin gene transcripts. Interestingly, ABCR hybridization was not observed at detectable levels in cone photoreceptors, as judged by comparisons with the hybridization patterns obtained with a blue cone pigment probe (compare FIG. 7A and FIG. 7D, FIG. 7E with FIG. 7F and FIG. 7G with FIG. 7H). Because melanin granules might obscure a weak hybridization signal in the RPE of a pigmented animal, the distribution of ABCR transcripts was also examined in both albino rats and albino mice. In these experiments, the ABCR hybridization signal was seen in the photoreceptor inner segments and was unequivocally absent from the RPE (FIG. 7E). Given that ABCR transcripts in each of these mammals, including a primate, are photoreceptor-specific, it is highly likely that the distribution of ABCR transcripts conforms to this pattern as well in the human retina.

The disclosures of each patent, patent application and publication cited or described in this document are hereby incorporated herein by reference, in their entirety.

Various modifications of the invention in addition to those shown and described herein will be apparent to those skilled in the art from the foregoing description. Such modifications are also intended to fall within the scope of the appended claims.

REFERENCES

Allikmets, R., Singh, N., Sun, H., Shroyer, N. F., Hutchinson, A., Chidambaram, A., Gerrard, B., Baird, L., Stauffer, D., Peiffer, A., Rattner, A., Smallwood, P., Li, Y., Anderson, K. L., Lewis, R. A., Nathans, J., Leppert, M., Dean, M., Lupski, J. R., (1997) A photoreceptor cell-specific ATP-binding transporter gene (ABCR) is mutated in recessive Stargardt macular dystrophy. *Nature Genetics.* 15(3):23646.

Allikmets, R., Shroyer, N. F., Singh, N., Seddon, J. M., Lewis, R. A., Bernsteinm P. S., Peiffer, A., Zabriskie, N. A., Li, Y., Hutchinson, A., Dean, M., Lupski, J. R., Leppert, M., (1997) Mutation of the Stargardt disease gene (ABCR) in age-related macular degeneration. *Science.* 277(5333): 1805-7.

Allikmets, R., Gerrard B., Hutchinson, A., and Dean, M. (1996). Characterization of the human ABC superfamily: Isolation and mapping of 21 new genes using the Expressed Sequence Tag database. *Hum. Mol. Genet.* 5, 1649-1655.

Allikmets, R., Gerrard, B., Glavač, D., Ravnik-Glavač, M., Jenkins, N. A., Gilbert, D. J., Copeland, N. G., Modi, W., and Dean, M. (1995). Characterization and mapping of three new mammalian ATP-binding transporter genes from an EST database. *Mam. Genome* 6, 114-117.

Allikmets, R., Gerrard, B., Court, D. and Dean, M. (1993). Cloning and organization of the abc and mdl genes of *Escherichia coli*: relationship to eukaryotic multidrug resistance. *Gene* 136, 231-236.

Altschul, S. F., Gish, W., Miller, W., Myers, E. W., and Lipman, D. J. (1990). Basic local alignment search tool. *J. Mol. Biol.* 215, 403-410.

Anderson, K. L., Baird, L., Lewis, R. A., Chinault, A. C., Otterud, B., Leppert, M., and Lupski, J. R. (1995). A YAC contig encompassing the recessive Stargardt disease gene (STGD) on chromosome 1p. *Am. J. Hum. Genet.* 57, 1351-1363.

Anderson, K. L. (Jul. 30, 1996) Towards the Isolation of Genes for Recessively Inherited Ocular Disorders; Bardet-Biedl Syndrome, Leber Congenital Amaurosis, Primary Congenital Glaucoma, and Stargardt Disease. Ph.D. Thesis. Baylor College of Medicine.

Anderson, R. E. and Maude, M. B. (1971). Lipids of ocular tissues: the effects of essential fatty acid deficiency on the phospholipids of the photoreceptor membranes of rat retina. *Arch. Biochem. Biophys.* 151, 270-276.

Azarian, S. M., Travis, G. H., (1997) The photoreceptor rim protein is an ABC transporter encoded by the gene for recessive Stargardt's disease (ABCR). *FEBS Letters.* 409 (2):247-52.

Bellanne-Chantelot, C., et al. (1992). Mapping the Whole Human Genome by Fingerprinting Yeast Artificial Chromosomes. *Cell* 70, 1059-1068.

Bimbach, C. D., Järveläinen, M., Possin, D. E., and Milam, A. H. (1994). Histopathology and immunocytochemistry of the neurosensory retina in fundus flavimaculatus. *Opthalmology* 101, 1211-1219.

Blacharski, D. A. (1988). Fundus flavimaculatus. In Retinal Dystrophies and Degenerations, D. A. Newsome, ed. (New York: Raven Press), pp. 135-159.

Boguski, M. S., Lowe, T. M., and Tolstoshev, C. M. (1993). dbEST-database for "expressed sequence tags". *Nature Genet.* 4, 332-333.

Chen, Z.-Y., Battinelli, E. M., Hendricks, R. W., Powell, J. F., Middleton-Price, H., Sims, K. B., Breakfield, X. O., and Craig, I. W. (1993). Norrie disease gene: characterization of deletions and possible function. *Genomics* 16, 533-535.

Childs, S., and Ling, V. (1994). The MDR superfamily of genes and its biological implications. In Important Advances in Oncology, V. T. DeVita, S. Hellman and S. A. Rosenberg, eds. (Philadelphia, Pa.: Lippincott Company), pp. 21-36.

Chiu, M. I., Zack, D. J., Wang, Y., and Nathans, J. (1994). Murine and bovine blue cone pigment genes: cloning and characterization of two new members of the S family of visual pigments. *Genomics* 21, 440-443.

Chomczynski, P. and Sacchi, N. (1987). Single-step method of RNA isolation by acid guanidinium thiocyanate-phenol-chloroform extraction. *Anal. Biochem.* 162, 156-159.

Daemen, F. J. M. (1973). Vertebrate rod outer segment membranes. *Biochem. Biophys. Acta* 300, 255-288.

de la Salle, H., Hanau, D., Fricker, D., Urlacher, A., Kelly, A., Salamero, J., Powis, S. H., Donato, L., Bausinger, H., Laforet, M., Jeras, M., Spehner, D., Bieber, T., Falkenrodt, A., Cazenave, J.-P., Trowsdale, J., and Tongio, M.-M. (1994). Homozygous human TAP peptide transporter mutation in HLA class I deficiency. *Science* 265, 237-241.

Dean, M., and Allikmets, R. (1995). Evolution of ATP-binding cassette transporter genes. *Curr. Opin. Genet. Dev.* 5, 779-785.

Dean, M., Allikmets, R., Gerrard, B., Stewart, C., Kistler, A., Shafer, B., Michaelis, S., and Strathem, J. (1994). Mapping and sequencing of two yeast genes belonging to the ATP-binding cassette superfamily. *Yeast* 10, 377-383.

Devereaux, J., Haeberli, P., and Smithies, 0. (1984). A comprehensive set of sequence analysis programs for the VAX. Nucleic Acids Res. 12, 387-395.

Dowling, J. E. (1960). Chemistry of visual adaptation in the rat. *Nature* 188, 114-118.

Dryja, T. P. and Li, T. (1995). Molecular genetics of retinitis pigmentosa. *Hum. Mol. Genet.* 4, 1739-1743.

Eagle, R. C. Jr., Lucier, A. C., Bemadino, V. B. Jr., and Yanoff, M. (1980). Retinal pigment epithelial abnormalities in Fundus Flavimaculatus: A light and electron microscopic study. *Opthalmology* 87, 1189-1200.

Feeney, L. (1978). Lipofuscin and melanin of human retinal pigment epithelium. Fluorescence, enzyme cytochemical, and ultrastructural studies Invest. *Opthalmol. Vis. Sci.* 17, 583-600.

Feng, D.-F., and Doolittle, R. F. (1987). Progressive sequence alignment as a prerequisite to correct phyllogenetic trees. *J. Mol. Evol.* 25, 351-360.

Fishman, G. A. (1976). Fundus flavimaculatus: a clinical classification. *Arch. Opthalmol.* 94, 2061-2067.

Fong, S.-L., Liou, G. I., Landers, R. A., Alvarez, R. A., and Bridges, C. D. (1984). Purification and characterization of a retinol-binding glycoprotein synthesized and secreted by bovine neural retina. *J. Biol. Chem.* 259, 6534-6542.

Franceschetti, A. (1964). Uber tapeto-retinale Degenerationen im Kindesalter. In H. von Sautter, ed. Entwicklung und Fortschritt in der Augenheilkunde. (Stuttgart: Ferdinand Enke) pp. 107-120.

Gass, J. D. M. (1987). Stargardt's disease (Fundus Flavimaculatus) in Stereoscopic Atlas of Macular Diseases Diagnosis and Treatment, Volume 1, 3rd edition. pages 256-261. The C. V. Mosby Company, St. Louis, Mo.

Gerber, S., Rozet, J.-M., Bonneau, D., Souied, E., Camuzat, A., Dufier, J.-L., Amalric, P., Weissenbach, J., Munnich, A., and Kaplan, J. (1995). A gene for late-onset fundus flavimaculatus with macular dystrophy maps to chromosome 1p13. *Am. J. Hum. Genet.* 56, 396-399.

Glavac, D., and Dean, M. (1993). Optimization of the single-strand conformation polymorphism (SSCP) technique for detection of point mutations. *Hum. Mutat.* 2, 404-414.

Hayes, K. C. (1974). Retinal degeneration in monkeys induced by deficiencies of vitamin E or A. Invest, *Opthalmology* 13, 499-510.

Hettema, E. H., van Roermund, C. W. T., Distel, B., van den Berg, M., Vilela, C., Rodrigues-Pousada, C., Wanders, R. J. A., and Tabak, H. F. (1996). The ABC transporter proteins Pat1 and Pat2 are required for import of long-chain fatty acids into peroxisomes of *Saccharomyces cervisiae. EMBO J.* 15, 3813-3822.

Hoyng, C. B., Poppelaars, F., van de Pol, T. J. R., Kremer, H., Pinckers, A. J. L. G., Deutman, A. F., and Cremers, F. P. M. (1996). Genetic fine mapping of the gene for recessive Stargardt disease. *Hum. Genet.* 98, 500-504.

Hyde, S. C., Emsley, P., Hartshorn, M. J., Mimmack, M. M., Gileadi, U., Pearce, S. R., Gallagher, M. P., Gill, D. R., Hubbard, R. E., and Higgins, C. F. (1990). Structural model of ATP-binding proteins associated with cystic fibrosis, multidrug resistance and bacterial transport. *Nature* 346, 362-365.

Klein, B. A. and Krill, A. E. (1967). Fundus Flavimaculatus: clinical, functional, and histopathologic observations. *Am. J. Opthalmol.* 64, 3-23.

Klugbauer, N., and Hofmann, F. (1996). Primary structure of a novel ABC transporter with a chromosomal localization on the band encoding the multidrug resistance-associated protein. *FEBS Lett.* 391, 61-65.

Kuwano, Y., Nakanishi, O., Nabeshima, Y.-I., Tanaka, T., and Ogata, K. (1985). Molecular cloning and nucleotide sequence of DNA complementary to rat ribosomal protein S26 messenger RNA. *J. Biochem*. (Tokyo) 97:983-992.

Lennon, G., Auffray, C., Polymeropoulos, M. and Soares, M. B. (1996). The I.M.A.G.E. consortium: An integrated molecular analysis of genomes and their expression. *Genomics* 33, 151-152.

Lincoln, A. L., Daly, M., and Lander, E. (1991). PRIMER: a computer program for automatically selecting PCR primers. Whitehead Institute Technical Report.

Lopez, P. F., Maumenee, I. H., de la Cruz, Z., Green, W. R. (1990). Autosomal-dominant fundus flavimaculatus: clinicopathologic correlation. *Ophthalmology* 97, 798-809.

Luciani, M.-F., Denizot, F., Savary, S., Mattei, M. G., and Chimini, G. (1994). Cloning of two novel ABC transporters mapping on human chromosome 9. *Genomics* 21, 150-159.

Luciani, M.-F., and Chimini, G. (1996). The ATP binding cassette transporter ABC1, is required for the engulfment of corpses generated by apoptotic cell death. *EMBO J.* 15, 226-235.

McDonnell, P. J., Kivlin, J. D., Maumenee, I. H., and Green, W. R. (1986). Fundus flavimaculatus without maculopathy: a clinicopathologic study. *Ophthalmology* 93, 116-119.

Meindl, A., Berger, W., Meitinger, T., van de Pol, D., Achatz, H., Dorner, C., Hasseman, M., Hellebrand, H., Gal, A., Crèmers, F., and Ropers, H. H. (1992). Norrie disease is caused by mutations in an extracellular protein resembling c-terminal globular domain of mucins. *Nat. Genet.* 2, 139-143.

Meindl, A., Dry, K., Herrmann, K., Manson, F., Ciccodicola, A., Edgar, A., Carvalho, M. R. S., Achatz, H., Hellebrand, H., Lennon, A., Mibliaccio, C., Porter, K., Zrenner, E., Bird, A., Jay, M., Lorenz, B., Wittwer, B., D'urso, M., Meitinger, T., and Wright, A. (1996): A gene (RPGR) with homology to the RCC 1 guanine nucleotide exchange factor is mutated in X-linked retinitis pigmentosa (RP3). *Nat. Genet.* 13, 35-42.

Michaelis, S., and Berkower, C. (1995). Sequence comparison of yeast ATP binding cassette (ABC) proteins. In Cold Spring Harbor Symposium on Quantitative Biology, vol.LX: Protein Kinesis—The Dynamics of Protein Trafficking and Stability. (Cold Spring Harbor Laboratory Press, Cold Spring Harbor).

Mosser, J., Douar, A.-M., Sarde, C.-O., Kioschis, P., Feil, R., Moser, H., Poustka, A.-M., Mandel, J.-L., and Aubourg, P. (1993). Putative X-linked adrenoleukodystrophy gene shares unexpected homology with ABC transporters. *Nature* 361, 726-730.

Nathans, J., Thomas, D., and Hogness, D. S. (1986). Molecular genetics of human color vision: the genes encoding blue, green, and red pigments. *Science* 232, 193-202.

Nickells, R. W., Burgoyne, C. F., Quigley, H. A., and Zack, D. J. (1995). Cloning and characterization of rodopsin cDNA from the old world monkey, Macaca fasciclaris. *Investigative Opthalmology and Visual Science* 36:72-82.

Noble, K. G., and Carr, R. E. (1979). Stargardt's disease and fundus flavimaculatus. Arch. Opthalmol. 97, 1281-1285.

Orita, M., Suzuki, Y., Sekiya, T., and Hayashi, K. (1989). Rapid and sensitive detection of point mutations and DNA polymorphisms using the polymerase chain reaction. *Genomics* 5, 874-879.

Rando, R. R. (1990). The chemistry of vitamin A and vision. *Angew. Chem. Int. Ed. Engl.* 29, 461-480.

Riordan, J. R., Rommens, J. M., Kerem, B.-S., Alon, N., Rozmahel, R., Grzelczak, Z., Zielenski, J., Lok, S., Plavsic, N., Chou, J.-L., Drumm, M. L., Ianuzzi, M. C., Collins, F. S., and Tsui, L.-C. (1989). Identification of the cystic fibrosis gene: cloning and characterization of complementary DNA. *Science* 245, 1066-1073.

Roa, B. B., Garcia, C. A., Suter, U., Kulpa, D. A., Wise, C. A., Mueller, J., Welcher, A. A., Snipes, G. J., Shooter, E. M., Patel, P. I., and Lupski, J. R. (1993). Charcot-Marie-Tooth disease type 1A, association with a spontaneous point mutation in the PMP22 gene. *New Eng. J. Med.* 329, 96-101.

Roa, B. B., Warner, L. E., Garcia, C. A., Russo, D., Lovelace, R., Chance P. F., and Lupski, J. R. (1996). Myelin protein zero (MPZ) gene mutations in nonduplication type 1 Charcot-Marie-Tooth disease. *Hum. Mut.* 7, 36-45.

Rowe, L. B., Nadeau, J. H., Turner, R., Frankel, W. N., Letts, V. A., Eppig, J., Ko, M. S. H., Thurston, S. J., and Birkenmeier, E. H. (1994). Maps from two interspecific backcross DNA panels available as a community genetic mapping resource. *Mamm. Genome* 5, 253-274.

Sambrook, J., Fritsch, E. F., and Maniatis, T. (1989). Molecular Cloning. (Cold Spring Harbor, N.Y.: Cold Spring Harbor Laboratory).

Schaeren-Wiemers, N., and Gerfin-Moser, A. (1993). A single protocol to detect transcripts of various types and expression levels in neural tissue and culture cells: in situ hybridization using digoxigenin-labeled cRNA probes. *Histochemistry* 100, 431-440.

Seabra, M. C., Brown, M. S., and Goldstein, J. L. (1993). Retinal degeneration in choroideremia: deficiency of Rab geranylgeranyl transferase. *Science* 259, 377-381.

Shani, N. and Valle, D. (1996). A *Saccharomyces cerevisiae* homolog of the human adrenoleukodystrophy transporter is a heterodimer of two half ATP-binding cassette transporters. *Proc. Natl. Acad. Sci. USA* 93, 11901-11906.

Shimozawa, N., Tsukamoto, T., Suzuki, Y., Orii, T., Shirayoshi, Y., Mori, T., and Fujiki, Y. (1992). A human gene responsible for Zellweger syndrome that affects peroxisome assembly. *Science* 255, 1132-1134.

Smit, J. J. M., Schinkel, A. H., Oude Elferink, R. P. J., Groen, A. K., Wagenaar, E., van Deemter, L., Mol, C. A. A. M., Ottenhoff, R., van der Lugt, N. M. T., van Roon, M. A., van der Valk, M. A., Offerhaus, G. J. A., Bems, A. J. M., and Borst, P. (1993). Homozygous disruption of the murine mdr2 P-glycoprotein gene leads to a complete absence of phospholipid from bile and to liver disease. *Cell* 75, 451-462.

Stargardt, K. (1909). Uber familiare, progressive Degeneration in der Maculagegend des Auges. Albrecht von Graefes Arch. Klin. *Exp. Opthalmol.* 71, 534-550.

Steinmetz, R. L., Garner, A., Maguire, J. I., and Bird, A. C. (1991). Histopathology of incipient fundus flavimaculatus. *Opthalmology* 98, 953-956.

Stone, E. M., Nichols, B. E., Kimura, A. E., Weingeist, T. A., Drack, A., and Sheffield, V. C. (1994). Clinical features of a Stargardt-like dominant progressive macular dystrophy with genetic linkage to chromosome 6q. *Arch. Ophthalmol.* 112, 765-772.

Sun, H., Nathans, J., (1997) Stargardt's ABCR is localized to the disc membrane of retinal rod outer segments. *Nature Genetics.* 17(1):15-6.

Thomas, P. M., Cote, G. J., Wohllk, N., Haddad, B., Mathew, P. M., Rabl, W., Aguilar-Bryan, L., Gagel, R. F., and Bryan, J. (1995). Mutations in the sulfonylurea receptor gene in familial persistent hyperinsulinemic hypoglycemia of infancy. *Science* 268, 426-429.

Valle, D. and Simell, O. (1995). The hyperornithinemias. In the Metabolic and Molecular Basis of Inherited Disease, Scriver, C. R., Beaudet, A. L., Sly, W. S., and Valle, D., eds. (New York: McGraw Hill), pp. 1147-1185.

van Helvoort, A., Smith, A. J., Sprong, H., Fritzsche, I., Schinkel, A. H., Borst, P., and van Meer, G. (1996). MDR1P-glycoprotein is a lipid translocase of broad specificity, while MDR3P-glycoprotein specifically translocates phosphatidylcholine. *Cell* 87, 507-517.

Wang, Y., Macke, J. P., Abella, B. S., Andreasson, K., Worley, P., Gilbert, D. J., Copeland, N. G., Jenkins, N. A., and Nathans, J. (1996). A large family of putative transmembrane receptors homologous to the product of the Drosophilal tissue polarity gene frizzled. *J. Biol. Chem.* 271: 4468-4476.

Warner, L. E., Hilz, M. J., Appel, S. H., Killian, J. M., Kolodny, E. H., Karpati, G., Carpenter, S., Watters, G. V., Wheeler, C., Witt, D., Bodell, A., Nelis, E., Van Broeckhoven, C., and Lupski, J. R. (1996). Clinical phenotypes of different MPZ ($P_0$) mutations may include Charcot-Marie-Tooth type 1B, Dejerine-Sottas, and congenital hypomyelination. *Neuron* 17, 451-460.

Weber, B. H. F., Vogt, G.; Pruett, R. C., Stohr, H., and Felbor, U. (1994). Mutations in the tissue inhibitor of metalloproteinase-3 (TIMP3) in patients with Sorsby's fundus dystrophy. Nat. Genet. 8, 352-356.

Weiter, J. J., Delori, F. C., Wing, G. L., and Fitch, K. A. (1986). Retinal pigment epithelial lipofuscin and melanin and choroidal melanin in human eyes. *Invest. Opthalmol. Vis. Sci.* 27, 145-152.

White, M. B., Carvalho, M., Derse, D., O'Brien, S. J., and Dean, M. (1992). Detecting single base substitutions as heteroduplex polymorphisms. *Genomics* 12, 301-306.

Wing, G. L., Blanchard, G. C., and Weiter, J. J. (1978). The topography and age relationship of lipofuscin concentration in the retinal pigment epithelium. *Invest. Opthalmol. Vis. Sci.* 17, 601-607.

Zhang, K., Bither, P. P., Park, R., Donoso, L. A., Seidman, J. G., and Seidman, C. E. (1994). A dominant Stargardt's macular dystrophy locus maps to chromosome 13q34. *Arch. Opthalmol.* 112, 759-764.

Zhou, H., Yoshioka, T., and Nathans, J. (1996). Retina-derived POU-domain factor-1: a complex POU-domain gene implicated in the development of retinal ganglion and amacrine cells. *J. Neurosci.* 16, 2261-2274.

Zinn, K. M. and Marmor, M. F. (1979). The Retinal Pigment Epithelium. (Harvard University Press, Cambridge, Mass.) pp 521.

What is claimed is:

1. A method for expressing a wild-type ATP-binding cassette transporter (ABCR) in a patient having macular degeneration resulting from an ABCR deficiency comprising:

identifying a patient having macular degeneration resulting from an ABCR deficiency, and administering to said patient a vector comprising a polynucleotide encoding a wild-type ABCR wherein said polynucleotide is operably linked to expression control sequences, wherein said vector is introduced into the cells of the subretinal space of the eye of said patient, wherein allowing expression of said ABCR in said patient suppresses said macular degeneration.

2. The method of claim 1 wherein said polynucleotide encodes a wild-type ABCR having an amino acid sequence of SEQ ID NO:3 or SEQ ID NO:6.

3. The method of claim 1 wherein said polynucleotide comprises the nucleic acid sequence of SEQ ID NO:1, SEQ ID NO:2, or SEQ ID NO:5.

4. The method of claim 1 wherein said patient is a human.

5. The method of claim 1 wherein said macular degeneration is due to Stargardt Disease, Fundus Flavimaculatus, age-related macular degeneration, retinitis pigmentosa, combined rod and cone dystrophies, cone dystrophies, cone degeneration, pattern dystrophy, or bull's eye maculopathy.

6. The method of claim 1 wherein said macular degeneration is due to Stargardt Disease.

* * * * *